US011713469B2

(12) United States Patent
Uil

(10) Patent No.: US 11,713,469 B2
(45) Date of Patent: Aug. 1, 2023

(54) RECOMBINANT ADENOVIRAL VECTOR EXPRESSING ZIKA ANTIGEN WITH IMPROVED PRODUCTIVITY

(71) Applicant: Janssen Vaccines & Prevention B.V., Leiden (NL)

(72) Inventor: Taco Gilles Uil, Leiden (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 115 days.

(21) Appl. No.: 17/261,436

(22) PCT Filed: Jul. 19, 2019

(86) PCT No.: PCT/EP2019/069461
§ 371 (c)(1),
(2) Date: Jan. 19, 2021

(87) PCT Pub. No.: WO2020/016394
PCT Pub. Date: Jan. 23, 2020

(65) Prior Publication Data

US 2021/0317477 A1 Oct. 14, 2021

Related U.S. Application Data

(60) Provisional application No. 62/701,403, filed on Jul. 20, 2018.

(51) Int. Cl.

| | |
|---|---|
| ***C12N 15/86*** | (2006.01) |
| ***A61P 31/14*** | (2006.01) |
| ***A61K 39/12*** | (2006.01) |
| ***C07K 14/005*** | (2006.01) |

(52) U.S. Cl.
CPC .............. *C12N 15/86* (2013.01); *A61K 39/12* (2013.01); *A61P 31/14* (2018.01); *C07K 14/005* (2013.01); *C12N 2750/14143* (2013.01); *C12N 2750/14152* (2013.01); *C12N 2770/24122* (2013.01); *C12N 2830/006* (2013.01)

(58) Field of Classification Search
None
See application file for complete search history.

(56) References Cited

U.S. PATENT DOCUMENTS

| | | | |
|---|---|---|---|
| 6,083,716 | A | 7/2000 | Wilson |
| 7,270,811 | B2 | 9/2007 | Bout |

FOREIGN PATENT DOCUMENTS

| | | | |
|---|---|---|---|
| WO | 200070071 | A1 | 11/2000 |
| WO | 2003104467 | A1 | 12/2003 |
| WO | 2004001032 | A2 | 12/2003 |
| WO | 2005071093 | A2 | 8/2005 |
| WO | 2007073513 | A2 | 6/2007 |
| WO | 2007104792 | A2 | 9/2007 |
| WO | 2010085984 | A1 | 8/2010 |
| WO | 2010086189 | A2 | 8/2010 |
| WO | 2012082918 | A1 | 6/2012 |
| WO | 2016071306 | A1 | 5/2016 |
| WO | 2017132210 | A1 | 8/2017 |
| WO | 2017214596 | A1 | 12/2017 |
| WO | 20180146205 | | 8/2018 |

OTHER PUBLICATIONS

International Search Report and Written Opinion for App. No. PCT/EP2019/069461, dated Nov. 12, 2019, 13 pages.
Matthew Cottingham et al., Preventing Spontaneous Genetic Rearrangements in the Transgene Cassettes of Adenovirus Vectors, Biotechnology and Bioengineering, Mar. 2012, pp. 719-728, vol. 109, No. 3, Wiley Periodicals, Inc.
Abbink, P., et al., "Durability and correlates of vaccine protection against Zika virus in rhesus monkeys", Science Translational Medicine, US, vol. 9, No. 420, p. 4163 (2017).
Qiang Guo et al., "Immunization With a Novel Human Type 5 Adenovirus-Vectored Vaccine Expressing the Premembrane and Envelope Proteins of Zika Virus Provides Consistent and Sterilizing Protection in Multiple Immunocompetent and Immunocompromised Animal Models", Journal of Infectious Diseases. JID, vol. 218, No. 3, Jul. 2, 2018 (Jul. 2, 2018), pp. 365-377, XP055551632, US, ISSN: 0022-1899, DOI: 10.1093/infdis/jiy187.
Abbink Peter et al., "Zika virus vaccines", Nature Reviews. Microbiology, vol. 16, No. 10, pp. 594-600, (2018).
Abbink, P., et al., "Comparative seroprevalence and immunogenicity of six rare serotype recombinant adenovirus vaccine vectors from subgroups B and D", Journal of Virology, The American Society for Microbiology, vol. 81, No. 9, pp. 4654-4663, (2007).
Altschul et al. "Basic Local Alignment Search Tool" J. Mol. Biol., vol. 215, pp. 403-410, 1990.
Altschul et al., "Gapped BLAST and PSI-BLAST: A New Generation Of Protein Database Search Programs," Nucleic Acids Research, vol. 25, No. 17, pp. 3389-3402 (1997).
Bangari, D., et al., "Development of nonhuman adenoviruses as vaccine vectors," Vaccine, vol. 24, No. 7, pp. 849-862 (2006).
Cohen, C., et al., "Chimpanzee Adenovirus CV-68 Adapted as a Gene Delivery Vector Interacts with the Coxsackievirus and Adenovirus Receptor", J. Gen. Virol., vol. 83, pp. 151-155 (2002).
Farina , S. et al., "Replication-Defective Vector Based on a Chimpanzee Adenovirus", Journal of Virology, vol. 75, No. 23, pp. 11603-11613 (2001).

(Continued)

*Primary Examiner* — Stacy B Chen
(74) *Attorney, Agent, or Firm* — Ice Miller LLP

(57) ABSTRACT

Provided herein are adenoviral vectors comprising nucleotide sequences encoding a Zika virus M and Env antigen, wherein the nucleotide sequence encoding the Zika virus M and Env antigen is operably linked to a cytomegalovirus (CMV) promoter comprising at least one tetracycline operator (TetO) motif. Also provided herein are pharmaceutical compositions comprising the adenoviral vectors, methods of producing the adenoviral vectors, methods of preventing Zika virus or the progression of Zika virus in a subject in need thereof, and kits comprising the adenoviral vectors and host cells.

22 Claims, 6 Drawing Sheets

Specification includes a Sequence Listing.

(56) References Cited

OTHER PUBLICATIONS

Havenga, M., et al., "Novel Replication-Incompetent Adenoviral B-Group Vectors: High Vector Stability and Yield in PER. C6 Cells," J. Gen. Virol., vol. 87, pp. 2135-2143 (2006).
Henikoff et al., "Amino acid substitution matrices from protein blocks," Proceedings of the National Academy of Sciences of the United States of America, vol. 89, No. 22, pp. 10915-10919 (Nov. 1992).
Karlin et al., "Applications and statistics for multiple high-scoring segments in molecular sequences," Proceedings of the National Academy of Sciences of the United States of America, vol. 90, pp. 5873-5877 (Jun. 1993).
Kobinger, G., et al., "Chimpanzee adenovirus vaccine protects against Zaire Ebola virus," Virology, vol. 346, pp. 394-401 (2006).
Lasaro, M., et al., "New Insights on Adenovirus as Vaccine Vectors," Molecular Therapy, vol. 17, No. 8, pp. 1333-1339 (2009).
Needleman et al., "A General Method Applicable to the Search Similarities in the Amino Acid Sequence of Two Proteins," Journal of Molecular Biology, vol. 48, pp. 443-453 (1970).
Pearson et al., "Improved tools for biological sequence comparison," Proceedings of the National Academy of Sciences of the United States of America, vol. 85, pp. 2444-2448 (1988).
Smith et al., "Comparison of Biosequences," Advances in Applied Mathematics, vol. 2, pp. 482-489 (1981).
Tatsis, N., et al., "A CD46-binding Chimpanzee Adenovirus Vector as a Vaccine Carrier", Mol. Therapy, vol. 15, No. 3, pp. 608-617 (2007).
Vogels et al., "Replication-Deficient Human Adenovirus Type 35 Vectors for Gene Transfer and Vaccination: Efficient Human Cell Infection and Bypass of Preexisting Adenovirus Immunity," Journal of Virology, vol. 77, No. 15, pp. 8263-8271 (Aug. 2003).

SEQUENCE LISTING

```
<160> NUMBER OF SEQ ID NOS: 20

<210> SEQ ID NO 1
<211> LENGTH: 603
<212> TYPE: PRT
<213> ORGANISM: Artificial Sequence
<220> FEATURE:
<223> OTHER INFORMATION: Zika virus M and Env antigen

<400> SEQUENCE: 1

Met Gly Lys Arg Ser Ala Gly Ser Ile Met Trp Leu Ala Ser Leu Ala
1               5                   10                  15

Val Val Ile Ala Cys Ala Gly Ala Ala Val Thr Leu Pro Ser His Ser
            20                  25                  30

Thr Arg Lys Leu Gln Thr Arg Ser Gln Thr Trp Leu Glu Ser Arg Glu
        35                  40                  45

Tyr Thr Lys His Leu Ile Arg Val Glu Asn Trp Ile Phe Arg Asn Pro
    50                  55                  60

Gly Phe Ala Leu Ala Ala Ala Ala Ile Ala Trp Leu Leu Gly Ser Ser
65                  70                  75                  80

Thr Ser Gln Lys Val Ile Tyr Leu Val Met Ile Leu Leu Ile Ala Pro
                85                  90                  95

Ala Tyr Ser Ile Arg Cys Ile Gly Val Ser Asn Arg Asp Phe Val Glu
            100                 105                 110

Gly Met Ser Gly Gly Thr Trp Val Asp Val Val Leu Glu His Gly Gly
        115                 120                 125

Cys Val Thr Val Met Ala Gln Asp Lys Pro Thr Val Asp Ile Glu Leu
    130                 135                 140

Val Thr Thr Thr Val Ser Asn Met Ala Glu Val Arg Ser Tyr Cys Tyr
```

-continued

```
145                 150                 155                 160

Glu Ala Ser Ile Ser Asp Met Ala Ser Asp Ser Arg Cys Pro Thr Gln
                165                 170                 175

Gly Glu Ala Tyr Leu Asp Lys Gln Ser Asp Thr Gln Tyr Val Cys Lys
            180                 185                 190

Arg Thr Leu Val Asp Arg Gly Trp Gly Asn Gly Cys Gly Leu Phe Gly
        195                 200                 205

Lys Gly Ser Leu Val Thr Cys Ala Lys Phe Ala Cys Ser Lys Lys Met
    210                 215                 220

Thr Gly Lys Ser Ile Gln Pro Glu Asn Leu Glu Tyr Arg Ile Met Leu
225                 230                 235                 240

Ser Val His Gly Ser Gln His Ser Gly Met Ile Val Asn Asp Thr Gly
                245                 250                 255

His Glu Thr Asp Glu Asn Arg Ala Lys Val Glu Ile Thr Pro Asn Ser
            260                 265                 270

Pro Arg Ala Glu Ala Thr Leu Gly Gly Phe Gly Ser Leu Gly Leu Asp
        275                 280                 285

Cys Glu Pro Arg Thr Gly Leu Asp Phe Ser Asp Leu Tyr Tyr Leu Thr
    290                 295                 300

Met Asn Asn Lys His Trp Leu Val His Lys Glu Trp Phe His Asp Ile
305                 310                 315                 320

Pro Leu Pro Trp His Ala Gly Ala Asp Thr Gly Thr Pro His Trp Asn
                325                 330                 335

Asn Lys Glu Ala Leu Val Glu Phe Lys Asp Ala His Ala Lys Arg Gln
            340                 345                 350

Thr Val Val Val Leu Gly Ser Gln Glu Gly Ala Val His Thr Ala Leu
        355                 360                 365

Ala Gly Ala Leu Glu Ala Glu Met Asp Gly Ala Lys Gly Arg Leu Ser
    370                 375                 380

Ser Gly His Leu Lys Cys Arg Leu Lys Met Asp Lys Leu Arg Leu Lys
385                 390                 395                 400

Gly Val Ser Tyr Ser Leu Cys Thr Ala Ala Phe Thr Phe Thr Lys Ile
                405                 410                 415

Pro Ala Glu Thr Leu His Gly Thr Val Thr Val Glu Val Gln Tyr Ala
            420                 425                 430

Gly Thr Asp Gly Pro Cys Lys Val Pro Ala Gln Met Ala Val Asp Met
        435                 440                 445

Gln Thr Leu Thr Pro Val Gly Arg Leu Ile Thr Ala Asn Pro Val Ile
    450                 455                 460

Thr Glu Ser Thr Glu Asn Ser Lys Met Met Leu Glu Leu Asp Pro Pro
465                 470                 475                 480

Phe Gly Asp Ser Tyr Ile Val Ile Gly Val Gly Glu Lys Lys Ile Thr
                485                 490                 495

His His Trp His Arg Ser Gly Ser Thr Ile Gly Lys Ala Phe Glu Ala
            500                 505                 510

Thr Val Arg Gly Ala Lys Arg Met Ala Val Leu Gly Asp Thr Ala Trp
        515                 520                 525

Asp Phe Gly Ser Val Gly Gly Ala Leu Asn Ser Leu Gly Lys Gly Ile
    530                 535                 540

His Gln Ile Phe Gly Ala Ala Phe Lys Ser Leu Phe Gly Gly Met Ser
545                 550                 555                 560

Trp Phe Ser Gln Ile Leu Ile Gly Thr Leu Leu Met Trp Leu Gly Leu
                565                 570                 575
```

```
Asn Thr Lys Asn Gly Ser Ile Ser Leu Met Cys Leu Ala Leu Gly Gly
            580                 585                 590

Val Leu Ile Phe Leu Ser Thr Ala Val Ser Ala
        595                 600


<210> SEQ ID NO 2
<211> LENGTH: 1809
<212> TYPE: DNA
<213> ORGANISM: Artificial Sequence
<220> FEATURE:
<223> OTHER INFORMATION: Zika virus M and Env antigen

<400> SEQUENCE: 2

atgggcaaaa gatccgccgg cagcatcatg tggctggcca gtctggctgt cgtgatcgcc      60

tgtgctggcg ccgctgtgac actgcctagc cacagcaccc ggaagctgca gaccagaagc     120

cagacctggc tggaaagcag agagtacacc aagcacctga tccgggtgga aaactggatc     180

ttccggaacc ccggcttcgc cctggccgct gctgctattg cttggctgct gggcagcagc     240

accagccaga aagtgatcta cctcgtgatg atcctgctga tcgcccctgc ctacagcatc     300

cggtgtatcg gcgtgtccaa ccgggacttc gtggaaggca tgagcggcgg cacatgggtg     360

gacgtggtgc tggaacatgg cggctgcgtg acagtgatgg cccaggacaa gcccaccgtg     420

gacatcgagc tcgtgaccac caccgtgtcc aatatggccg aagtgcggag ctactgctac     480

gaggccagca tcagcgacat ggccagcgac agcagatgcc ctacacaggg cgaggcctac     540

ctggacaagc agtccgacac ccagtacgtg tgcaagcgga ccctggtgga tagaggctgg     600

ggcaatggct gcggcctgtt tggcaagggc agcctcgtga cctgcgccaa gttcgcctgc     660

agcaagaaga tgaccggcaa gagcatccag cccgagaacc tggaataccg gatcatgctg     720

agcgtgcacg gcagccagca ctccggcatg atcgtgaacg acaccggcca cgagacagac     780

gagaaccggg ccaaggtgga aatcaccccc aacagcccta gagccgaggc cacactgggc     840

ggctttggat ctctgggcct ggactgcgag cctagaaccg gcctggattt cagcgacctg     900

tactacctga ccatgaacaa caaacactgg ctggtgcaca aagagtggtt ccacgacatc     960

cccctgccct ggcatgccgg cgctgataca ggcacacccc actggaacaa caaagaggcc    1020

ctggtggagt tcaaggacgc ccacgccaag aggcagaccg tggtggtgct gggatctcag    1080

gaaggcgccg tgcatacagc tctggctggc gccctggaag ccgaaatgga tggcgctaag    1140

ggcagactgt ccagcggcca cctgaagtgc cggctgaaga tggacaagct gcggctgaag    1200

ggcgtgtcct acagcctgtg taccgccgcc ttcaccttca ccaagatccc cgccgagaca    1260

ctgcacggca ccgtgactgt ggaagtgcag tacgccggca ccgacggccc ttgtaaagtg    1320

cctgctcaga tggccgtgga tatgcagacc ctgacccctg tgggcaggct gatcaccgcc    1380

aaccctgtga tcaccgagag caccgagaac agcaagatga tgctggaact ggacccaccc    1440

ttcggcgaca gctacatcgt gatcggcgtg ggagagaaga agatcaccca ccactggcac    1500

agaagcggca gcaccatcgg caaggccttt gaggctacag tgcggggagc caagagaatg    1560

gccgtgctgg gagataccgc ctgggacttt ggctctgtgg gcggagccct gaactctctg    1620

ggcaagggaa tccaccagat cttcggcgct gccttcaaga gcctgttcgg cggcatgagc    1680

tggttcagcc agatcctgat cggcaccctg ctgatgtggc tgggcctgaa caccaagaac    1740

ggctccatca gcctgatgtg cctggctctg ggaggcgtgc tgatcttcct gagcacagcc    1800

gtgtccgcc                                                           1809
```

-continued

<210> SEQ ID NO 3
<211> LENGTH: 829
<212> TYPE: DNA
<213> ORGANISM: Artificial Sequence
<220> FEATURE:
<223> OTHER INFORMATION: CMVTetO2A1 promoter

<400> SEQUENCE: 3

```
tcaatattgg ccattagcca tattattcat tggttatata gcataaatca atattggcta     60

ttggccattg catacgttgt atccatatca taatatgtac atttatattg gctcatgtcc    120

aacattaccg ccatgttgac attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtacg ccccctattg acgtcaatga    420

cggtaaatgg cccgcctggc attatgccca gtacatgacc ttatgggact ttcctacttg    480

gcagtacatc tacgtattag tcatcgctat taccatggtg atgcggtttt ggcagtacat    540

caatgggcgt ggatagcggt ttgactcacg gggatttcca agtctccacc ccattgacgt    600

caatgggagt ttgttttggc accaaaatca acgggacttt ccaaaatgtc gtaacaactc    660

cgccccattg acgcaaatgg gcggtaggcg tgtacggtgg gaggtctata taagcagagc    720

tcgtttagtt ccctatcagt gatagagaag acgccatcca cgctgttttg acctccatag    780

aagacaccgg gaccgatcca gcctccgcgg ccgggaacgg tgcattgga                829
```

<210> SEQ ID NO 4
<211> LENGTH: 829
<212> TYPE: DNA
<213> ORGANISM: Artificial Sequence
<220> FEATURE:
<223> OTHER INFORMATION: CMVTetO2A2 promoter

<400> SEQUENCE: 4

```
tcaatattgg ccattagcca tattattcat tggttatata gcataaatca atattggcta     60

ttggccattg catacgttgt atccatatca taatatgtac atttatattg gctcatgtcc    120

aacattaccg ccatgttgac attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtacg ccccctattg acgtcaatga    420

cggtaaatgg cccgcctggc attatgccca gtacatgacc ttatgggact ttcctacttg    480

gcagtacatc tacgtattag tcatcgctat taccatggtg atgcggtttt ggcagtacat    540

caatgggcgt ggatagcggt ttgactcacg gggatttcca agtctccacc ccattgacgt    600

caatgggagt ttgttttggc accaaaatca acgggacttt ccaaaatgtc gtaacaactc    660

cgccccattg acgcaaatgg gcggtaggcg tgtacggtgg gaggtctata aaagcagagc    720

tcgtttagtt ccctatcagt gatagagaag acgccatcca cgctgttttg acctccatag    780

aagacaccgg gaccgatcca gcctccgcgg ccgggaacgg tgcattgga                829
```

<210> SEQ ID NO 5
<211> LENGTH: 829

-continued

<212> TYPE: DNA
<213> ORGANISM: Artificial Sequence
<220> FEATURE:
<223> OTHER INFORMATION: CMVTetO2B1 promoter

<400> SEQUENCE: 5
tcaatattgg ccattagcca tattattcat tggttatata gcataaatca atattggcta 60
ttggccattg catacgttgt atccatatca taatatgtac atttatattg gctcatgtcc 120
aacattaccg ccatgttgac attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtacg ccccctattg acgtcaatga 420
cggtaaatgg cccgcctggc attatgccca gtacatgacc ttatgggact ttcctacttg 480
gcagtacatc tacgtattag tcatcgctat taccatggtg atgcggtttt ggcagtacat 540
caatgggcgt ggatagcggt ttgactcacg gggatttcca agtctccacc ccattgacgt 600
caatgggagt ttgttttggc accaaaatca acgggacttt ccaaaatgtc gtaacaactc 660
cgccccattg acgcaaatgg gcggtaggcg tgtacggtgg gaggtctata taagcagagc 720
tcgtttagtt ctctatcact gatagggaag acgccatcca cgctgttttg acctccatag 780
aagacaccgg gaccgatcca gcctccgcgg ccgggaacgg tgcattgga 829

<210> SEQ ID NO 6
<211> LENGTH: 829
<212> TYPE: DNA
<213> ORGANISM: Artificial Sequence
<220> FEATURE:
<223> OTHER INFORMATION: CMVTetO3A promoter

<400> SEQUENCE: 6
tcaatattgg ccattagcca tattattcat tggttatata gcataaatca atattggcta 60
ttggccattg catacgttgt atccatatca taatatgtac atttatattg gctcatgtcc 120
aacattaccg ccatgttgac attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtacg ccccctattg acgtcaatga 420
cggtaaatgg cccgcctggc attatgccca gtacatgacc ttatgggact ttcctacttg 480
gcagtacatc tacgtattag tcatcgctat taccatggtg atgcggtttt ggcagtacat 540
caatgggcgt ggatagcggt ttgactcacg gggatttcca agtctccacc ccattgacgt 600
caatgggagt ttgttttggc accaaaatca acgggacttt ccaaaatgtc gtaacaactc 660
cgccccattg acgcaaatgg gcggtaggcg tgtacggtgg gaggtctata taagcagagc 720
tcgtttagtg aaccgtcaga tccctatcag tgatagagaa cgctgttttg acctccatag 780
aagacaccgg gaccgatcca gcctccgcgg ccgggaacgg tgcattgga 829

<210> SEQ ID NO 7
<211> LENGTH: 829
<212> TYPE: DNA
<213> ORGANISM: Artificial Sequence
<220> FEATURE:

<223> OTHER INFORMATION: CMVTetO3B promoter

<400> SEQUENCE: 7

```
tcaatattgg ccattagcca tattattcat tggttatata gcataaatca atattggcta     60
ttggccattg catacgttgt atccatatca taatatgtac atttatattg gctcatgtcc    120
aacattaccg ccatgttgac attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtacg ccccctattg acgtcaatga    420
cggtaaatgg cccgcctggc attatgccca gtacatgacc ttatgggact ttcctacttg    480
gcagtacatc tacgtattag tcatcgctat taccatggtg atgcggtttt ggcagtacat    540
caatgggcgt ggatagcggt ttgactcacg gggatttcca agtctccacc ccattgacgt    600
caatgggagt ttgttttggc accaaaatca acgggacttt ccaaaatgtc gtaacaactc    660
cgccccattg acgcaaatgg gcggtaggcg tgtacggtgg gaggtctata taagcagagc    720
tcgtttagtg aaccgtcaga tctctatcac tgatagggaa cgctgttttg acctccatag    780
aagacaccgg gaccgatcca gcctccgcgg ccgggaacgg tgcattgga                 829
```

<210> SEQ ID NO 8
<211> LENGTH: 883
<212> TYPE: DNA
<213> ORGANISM: Artificial Sequence
<220> FEATURE:
<223> OTHER INFORMATION: CMVTetO v1 promoter

<400> SEQUENCE: 8

```
tcaatattgg ccattagcca tattattcat tggttatata gcataaatca atattggcta     60
ttggccattg catacgttgt atccatatca taatatgtac atttatattg gctcatgtcc    120
aacattaccg ccatgttgac attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtacg ccccctattg acgtcaatga    420
cggtaaatgg cccgcctggc attatgccca gtacatgacc ttatgggact ttcctacttg    480
gcagtacatc tacgtattag tcatcgctat taccatggtg atgcggtttt ggcagtacat    540
caatgggcgt ggatagcggt ttgactcacg gggatttcca agtctccacc ccattgacgt    600
caatgggagt ttgttttggc accaaaatca acgggacttt ccaaaatgtc gtaacaactc    660
cgccccattg acgcaaatgg gcggtaggcg tgtacggtgg gaggtctata taagcagagc    720
tctccctatc agtgatagag atctccctat cagtgataga gatcgtcgac gagctcgttt    780
agtgaaccgt cagatcgcct ggagacgcca tccacgctgt tttgacctcc atagaagaca    840
ccgggaccga tccagcctcc gcggccggga acggtgcatt gga                      883
```

<210> SEQ ID NO 9
<211> LENGTH: 2655
<212> TYPE: DNA
<213> ORGANISM: Artificial Sequence
<220> FEATURE:
<223> OTHER INFORMATION: CMVTetO2A1 promoter operably linked to ME Zika antigen

<400> SEQUENCE: 9

```
tcaatattgg ccattagcca tattattcat tggttatata gcataaatca atattggcta     60
ttggccattg catacgttgt atccatatca taatatgtac atttatattg gctcatgtcc    120
aacattaccg ccatgttgac attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtacg ccccctattg acgtcaatga    420
cggtaaatgg cccgcctggc attatgccca gtacatgacc ttatgggact ttcctacttg    480
gcagtacatc tacgtattag tcatcgctat taccatggtg atgcggtttt ggcagtacat    540
caatgggcgt ggatagcggt ttgactcacg gggatttcca agtctccacc ccattgacgt    600
caatgggagt ttgttttggc accaaaatca acgggacttt ccaaaatgtc gtaacaactc    660
cgccccattg acgcaaatgg gcggtaggcg tgtacggtgg gaggtctata taagcagagc    720
tcgtttagtt ccctatcagt gatagagaag acgccatcca cgctgttttg acctccatag    780
aagacaccgg gaccgatcca gcctccgcgg ccgggaacgg tgcattggaa gcttggtacc    840
gccaccatgg gcaaaagatc cgccggcagc atcatgtggc tggccagtct ggctgtcgtg    900
atcgcctgtg ctggcgccgc tgtgacactg cctagccaca gcacccggaa gctgcagacc    960
agaagccaga cctggctgga aagcagagag tacaccaagc acctgatccg ggtggaaaac   1020
tggatcttcc ggaaccccgg cttcgccctg gccgctgctg ctattgcttg gctgctgggc   1080
agcagcacca gccagaaagt gatctacctc gtgatgatcc tgctgatcgc ccctgcctac   1140
agcatccggt gtatcggcgt gtccaaccgg gacttcgtgg aaggcatgag cggcggcaca   1200
tgggtggacg tggtgctgga acatggcggc tgcgtgacag tgatggccca ggacaagccc   1260
accgtggaca tcgagctcgt gaccaccacc gtgtccaata tggccgaagt gcggagctac   1320
tgctacgagg ccagcatcag cgacatggcc agcgacagca gatgccctac acagggcgag   1380
gcctacctgg acaagcagtc cgacacccag tacgtgtgca agcggaccct ggtggataga   1440
ggctggggca atggctgcgg cctgtttggc aagggcagcc tcgtgacctg cgccaagttc   1500
gcctgcagca agaagatgac cggcaagagc atccagcccg agaacctgga ataccggatc   1560
atgctgagcg tgcacggcag ccagcactcc ggcatgatcg tgaacgacac cggccacgag   1620
acagacgaga accgggccaa ggtggaaatc acccccaaca gccctagagc cgaggccaca   1680
ctgggcggct ttggatctct gggcctggac tgcgagccta gaaccggcct ggatttcagc   1740
gacctgtact acctgaccat gaacaacaaa cactggctgg tgcacaaaga gtggttccac   1800
gacatccccc tgccctggca tgccggcgct gatacaggca caccccactg gaacaacaaa   1860
gaggccctgg tggagttcaa ggacgcccac gccaagaggc agaccgtggt ggtgctggga   1920
tctcaggaag gcgccgtgca tacagctctg gctggcgccc tggaagccga aatggatggc   1980
gctaagggca gactgtccag cggccacctg aagtgccggc tgaagatgga caagctgcgg   2040
ctgaagggcg tgtcctacag cctgtgtacc gccgccttca ccttcaccaa gatccccgcc   2100
gagacactgc acggcaccgt gactgtggaa gtgcagtacg ccggcaccga cggcccttgt   2160
aaagtgcctg ctcagatggc cgtggatatg cagaccctga cccctgtggg caggctgatc   2220
accgccaacc ctgtgatcac cgagagcacc gagaacagca agatgatgct ggaactggac   2280
```

```
ccacccttcg gcgacagcta catcgtgatc ggcgtgggag agaagaagat cacccaccac   2340

tggcacagaa gcggcagcac catcggcaag gcctttgagg ctacagtgcg gggagccaag   2400

agaatggccg tgctgggaga taccgcctgg gactttggct ctgtgggcgg agccctgaac   2460

tctctgggca agggaatcca ccagatcttc ggcgctgcct tcaagagcct gttcggcggc   2520

atgagctggt tcagccagat cctgatcggc accctgctga tgtggctggg cctgaacacc   2580

aagaacggct ccatcagcct gatgtgcctg gctctgggag gcgtgctgat cttcctgagc   2640

acagccgtgt ccgcc                                                    2655
```

<210> SEQ ID NO 10
<211> LENGTH: 2655
<212> TYPE: DNA
<213> ORGANISM: Artificial Sequence
<220> FEATURE:
<223> OTHER INFORMATION: CMVTetO2A2 promoter operably linked to ME Zika antigen

<400> SEQUENCE: 10

```
tcaatattgg ccattagcca tattattcat tggttatata gcataaatca atattggcta     60

ttggccattg catacgttgt atccatatca taatatgtac atttatattg gctcatgtcc    120

aacattaccg ccatgttgac attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtacg ccccctattg acgtcaatga    420

cggtaaatgg cccgcctggc attatgccca gtacatgacc ttatgggact ttcctacttg    480

gcagtacatc tacgtattag tcatcgctat taccatggtg atgcggtttt ggcagtacat    540

caatgggcgt ggatagcggt ttgactcacg gggatttcca agtctccacc ccattgacgt    600

caatgggagt ttgttttggc accaaaatca acgggacttt ccaaaatgtc gtaacaactc    660

cgccccattg acgcaaatgg gcggtaggcg tgtacggtgg gaggtctata aaagcagagc    720

tcgtttagtt ccctatcagt gatagagaag acgccatcca cgctgttttg acctccatag    780

aagacaccgg gaccgatcca gcctccgcgg ccgggaacgg tgcattggaa gcttggtacc    840

gccaccatgg gcaaaagatc cgccggcagc atcatgtggc tggccagtct ggctgtcgtg    900

atcgcctgtg ctggcgccgc tgtgacactg cctagccaca gcacccggaa gctgcagacc    960

agaagccaga cctggctgga aagcagagag tacaccaagc acctgatccg ggtggaaaac   1020

tggatcttcc ggaaccccgg cttcgccctg gccgctgctg ctattgcttg gctgctgggc   1080

agcagcacca gccagaaagt gatctacctc gtgatgatcc tgctgatcgc ccctgcctac   1140

agcatccggt gtatcggcgt gtccaaccgg gacttcgtgg aaggcatgag cggcggcaca   1200

tgggtggacg tggtgctgga acatggcggc tgcgtgacag tgatggccca ggacaagccc   1260

accgtggaca tcgagctcgt gaccaccacc gtgtccaata tggccgaagt gcggagctac   1320

tgctacgagg ccagcatcag cgacatggcc agcgacagca gatgccctac acagggcgag   1380

gcctacctgg acaagcagtc cgacacccag tacgtgtgca agcggaccct ggtggataga   1440

ggctggggca atggctgcgg cctgtttggc aagggcagcc tcgtgacctg cgccaagttc   1500

gcctgcagca agaagatgac cggcaagagc atccagcccg agaacctgga ataccggatc   1560

atgctgagcg tgcacggcag ccagcactcc ggcatgatcg tgaacgacac cggccacgag   1620
```

acagacgaga accgggccaa ggtggaaatc acccccaaca gccctagagc cgaggccaca 1680
ctgggcggct ttggatctct gggcctggac tgcgagccta gaaccggcct ggatttcagc 1740
gacctgtact acctgaccat gaacaacaaa cactggctgg tgcacaaaga gtggttccac 1800
gacatccccc tgccctggca tgccggcgct gatacaggca caccccactg gaacaacaaa 1860
gaggccctgg tggagttcaa ggacgcccac gccaagaggc agaccgtggt ggtgctggga 1920
tctcaggaag gcgccgtgca tacagctctg gctggcgccc tggaagccga aatggatggc 1980
gctaagggca gactgtccag cggccacctg aagtgccggc tgaagatgga caagctgcgg 2040
ctgaagggcg tgtcctacag cctgtgtacc gccgccttca ccttcaccaa gatccccgcc 2100
gagacactgc acggcaccgt gactgtggaa gtgcagtacg ccggcaccga cggccccttgt 2160 aaagtgcctg ctcagatggc cgtggatatg cagaccctga cccctgtggg caggctgatc 2220
accgccaacc ctgtgatcac cgagagcacc gagaacagca agatgatgct ggaactggac 2280
ccacccttcg gcgacagcta catcgtgatc ggcgtgggag agaagaagat cacccaccac 2340
tggcacagaa gcggcagcac catcggcaag gcctttgagg ctacagtgcg gggagccaag 2400
agaatggccg tgctgggaga taccgcctgg gactttggct ctgtgggcgg agccctgaac 2460
tctctgggca agggaatcca ccagatcttc ggcgctgcct tcaagagcct gttcggcggc 2520
atgagctggt tcagccagat cctgatcggc accctgctga tgtggctggg cctgaacacc 2580
aagaacggct ccatcagcct gatgtgcctg gctctgggag gcgtgctgat cttcctgagc 2640
acagccgtgt ccgcc 2655

<210> SEQ ID NO 11
<211> LENGTH: 2655
<212> TYPE: DNA
<213> ORGANISM: Artificial Sequence
<220> FEATURE:
<223> OTHER INFORMATION: CMVTetO2B1 promoter operably linked to ME Zika antigen

<400> SEQUENCE: 11
tcaatattgg ccattagcca tattattcat tggttatata gcataaatca atattggcta 60
ttggccattg catacgttgt atccatatca taatatgtac atttatattg gctcatgtcc 120
aacattaccg ccatgttgac attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtacg ccccctattg acgtcaatga 420
cggtaaatgg cccgcctggc attatgccca gtacatgacc ttatgggact ttcctacttg 480
gcagtacatc tacgtattag tcatcgctat taccatggtg atgcggtttt ggcagtacat 540
caatgggcgt ggatagcggt ttgactcacg gggatttcca agtctccacc ccattgacgt 600
caatgggagt ttgttttggc accaaaatca acgggacttt ccaaaatgtc gtaacaactc 660
cgccccattg acgcaaatgg gcggtaggcg tgtacggtgg gaggtctata taagcagagc 720
tcgtttagtt ctctatcact gatagggaag acgccatcca cgctgttttg acctccatag 780
aagacaccgg gaccgatcca gcctccgcgg ccgggaacgg tgcattggaa gcttggtacc 840
gccaccatgg gcaaaagatc cgccggcagc atcatgtggc tggccagtct ggctgtcgtg 900
atcgcctgtg ctggcgccgc tgtgacactg cctagccaca gcacccggaa gctgcagacc 960
agaagccaga cctggctgga aagcagagag tacaccaagc acctgatccg ggtggaaaac 1020
tggatcttcc ggaaccccgg cttcgccctg gccgctgctg ctattgcttg gctgctgggc 1080
agcagcacca gccagaaagt gatctacctc gtgatgatcc tgctgatcgc ccctgcctac 1140
agcatccggt gtatcggcgt gtccaaccgg gacttcgtgg aaggcatgag cggcggcaca 1200
tgggtggacg tggtgctgga acatggcggc tgcgtgacag tgatggccca ggacaagccc 1260
accgtggaca tcgagctcgt gaccaccacc gtgtccaata tggccgaagt gcggagctac 1320
tgctacgagg ccagcatcag cgacatggcc agcgacagca gatgccctac acagggcgag 1380
gcctacctgg acaagcagtc cgacacccag tacgtgtgca agcggaccct ggtggataga 1440
ggctggggca atggctgcgg cctgtttggc aagggcagcc tcgtgacctg cgccaagttc 1500
gcctgcagca agaagatgac cggcaagagc atccagcccg agaacctgga ataccggatc 1560
atgctgagcg tgcacggcag ccagcactcc ggcatgatcg tgaacgacac cggccacgag 1620
acagacgaga accgggccaa ggtggaaatc acccccaaca gccctagagc cgaggccaca 1680
ctgggcggct ttggatctct gggcctggac tgcgagccta gaaccggcct ggatttcagc 1740
gacctgtact acctgaccat gaacaacaaa cactggctgg tgcacaaaga gtggttccac 1800
gacatccccc tgccctggca tgccggcgct gatacaggca caccccactg gaacaacaaa 1860
gaggccctgg tggagttcaa ggacgcccac gccaagaggc agaccgtggt ggtgctggga 1920
tctcaggaag gcgccgtgca tacagctctg gctggcgccc tggaagccga aatggatggc 1980
gctaagggca gactgtccag cggccacctg aagtgccggc tgaagatgga caagctgcgg 2040
ctgaagggcg tgtcctacag cctgtgtacc gccgccttca ccttcaccaa gatccccgcc 2100
gagacactgc acggcaccgt gactgtggaa gtgcagtacg ccggcaccga cggccccttgt 2160 aaagtgcctg ctcagatggc cgtggatatg cagaccctga cccctgtggg caggctgatc 2220
accgccaacc ctgtgatcac cgagagcacc gagaacagca agatgatgct ggaactggac 2280
ccacccttcg gcgacagcta catcgtgatc ggcgtgggag agaagaagat cacccaccac 2340
tggcacagaa gcggcagcac catcggcaag gcctttgagg ctacagtgcg gggagccaag 2400
agaatggccg tgctgggaga taccgcctgg gactttggct ctgtgggcgg agccctgaac 2460
tctctgggca agggaatcca ccagatcttc ggcgctgcct tcaagagcct gttcggcggc 2520
atgagctggt tcagccagat cctgatcggc accctgctga tgtggctggg cctgaacacc 2580
aagaacggct ccatcagcct gatgtgcctg gctctgggag gcgtgctgat cttcctgagc 2640
acagccgtgt ccgcc 2655

<210> SEQ ID NO 12
<211> LENGTH: 2655
<212> TYPE: DNA
<213> ORGANISM: Artificial Sequence
<220> FEATURE:
<223> OTHER INFORMATION: CMVTetO3A promoter operably linked to ME Zika antigen

<400> SEQUENCE: 12
tcaatattgg ccattagcca tattattcat tggttatata gcataaatca atattggcta 60
ttggccattg catacgttgt atccatatca taatatgtac atttatattg gctcatgtcc 120
aacattaccg ccatgttgac attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300

```
agtaacgcca atagggactt tccattgacg tcaatgggtg gagtatttac ggtaaactgc    360
ccacttggca gtacatcaag tgtatcatat gccaagtacg ccccctattg acgtcaatga    420
cggtaaatgg cccgcctggc attatgccca gtacatgacc ttatgggact ttcctacttg    480
gcagtacatc tacgtattag tcatcgctat taccatggtg atgcggtttt ggcagtacat    540
caatgggcgt ggatagcggt ttgactcacg gggatttcca agtctccacc ccattgacgt    600
caatgggagt ttgttttggc accaaaatca acgggacttt ccaaaatgtc gtaacaactc    660
cgccccattg acgcaaatgg gcggtaggcg tgtacggtgg gaggtctata taagcagagc    720
tcgtttagtg aaccgtcaga tccctatcag tgatagagaa cgctgttttg acctccatag    780
aagacaccgg gaccgatcca gcctccgcgg ccgggaacgg tgcattggaa gcttggtacc    840
gccaccatgg gcaaaagatc cgccggcagc atcatgtggc tggccagtct ggctgtcgtg    900
atcgcctgtg ctggcgccgc tgtgacactg cctagccaca gcacccggaa gctgcagacc    960
agaagccaga cctggctgga aagcagagag tacaccaagc acctgatccg ggtggaaaac   1020
tggatcttcc ggaaccccgg cttcgccctg gccgctgctg ctattgcttg gctgctgggc   1080
agcagcacca gccagaaagt gatctacctc gtgatgatcc tgctgatcgc ccctgcctac   1140
agcatccggt gtatcggcgt gtccaaccgg gacttcgtgg aaggcatgag cggcggcaca   1200
tgggtggacg tggtgctgga acatggcggc tgcgtgacag tgatggccca ggacaagccc   1260
accgtggaca tcgagctcgt gaccaccacc gtgtccaata tggccgaagt gcggagctac   1320
tgctacgagg ccagcatcag cgacatggcc agcgacagca gatgccctac acagggcgag   1380
gcctacctgg acaagcagtc cgacacccag tacgtgtgca agcggaccct ggtggataga   1440
ggctggggca atggctgcgg cctgtttggc aagggcagcc tcgtgacctg cgccaagttc   1500
gcctgcagca agaagatgac cggcaagagc atccagcccg agaacctgga ataccggatc   1560
atgctgagcg tgcacggcag ccagcactcc ggcatgatcg tgaacgacac cggccacgag   1620
acagacgaga accgggccaa ggtggaaatc acccccaaca gccctagagc cgaggccaca   1680
ctgggcggct ttggatctct gggcctggac tgcgagccta gaaccggcct ggatttcagc   1740
gacctgtact acctgaccat gaacaacaaa cactggctgg tgcacaaaga gtggttccac   1800
gacatccccc tgccctggca tgccggcgct gatacaggca caccccactg gaacaacaaa   1860
gaggccctgg tggagttcaa ggacgcccac gccaagaggc agaccgtggt ggtgctggga   1920
tctcaggaag gcgccgtgca tacagctctg gctggcgccc tggaagccga aatggatggc   1980
gctaagggca gactgtccag cggccacctg aagtgccggc tgaagatgga caagctgcgg   2040
ctgaagggcg tgtcctacag cctgtgtacc gccgccttca ccttcaccaa gatccccgcc   2100
gagacactgc acggcaccgt gactgtggaa gtgcagtacg ccggcaccga cggcccttgt   2160
aaagtgcctg ctcagatggc cgtggatatg cagaccctga cccctgtggg caggctgatc   2220
accgccaacc ctgtgatcac cgagagcacc gagaacagca agatgatgct ggaactggac   2280
ccacccttcg gcgacagcta catcgtgatc ggcgtgggag agaagaagat cacccaccac   2340
tggcacagaa gcggcagcac catcggcaag gcctttgagg ctacagtgcg gggagccaag   2400
agaatggccg tgctgggaga taccgcctgg gactttggct ctgtgggcgg agccctgaac   2460
tctctgggca agggaatcca ccagatcttc ggcgctgcct tcaagagcct gttcggcggc   2520
atgagctggt tcagccagat cctgatcggc accctgctga tgtggctggg cctgaacacc   2580
aagaacggct ccatcagcct gatgtgcctg gctctgggag gcgtgctgat cttcctgagc   2640
```

acagccgtgt ccgcc 2655

<210> SEQ ID NO 13
<211> LENGTH: 2655
<212> TYPE: DNA
<213> ORGANISM: Artificial Sequence
<220> FEATURE:
<223> OTHER INFORMATION: CMVTetO3B promoter operably linked to ME Zika antigen

<400> SEQUENCE: 13
tcaatattgg ccattagcca tattattcat tggttatata gcataaatca atattggcta 60
ttggccattg catacgttgt atccatatca taatatgtac atttatattg gctcatgtcc 120
aacattaccg ccatgttgac attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtacg ccccctattg acgtcaatga 420
cggtaaatgg cccgcctggc attatgccca gtacatgacc ttatgggact ttcctacttg 480
gcagtacatc tacgtattag tcatcgctat taccatggtg atgcggtttt ggcagtacat 540
caatgggcgt ggatagcggt ttgactcacg gggatttcca agtctccacc ccattgacgt 600
caatgggagt ttgttttggc accaaaatca acgggacttt ccaaaatgtc gtaacaactc 660
cgccccattg acgcaaatgg gcggtaggcg tgtacggtgg gaggtctata taagcagagc 720
tcgtttagtg aaccgtcaga tctctatcac tgatagggaa cgctgttttg acctccatag 780
aagacaccgg gaccgatcca gcctccgcgg ccgggaacgg tgcattggaa gcttggtacc 840
gccaccatgg gcaaaagatc cgccggcagc atcatgtggc tggccagtct ggctgtcgtg 900
atcgcctgtg ctggcgccgc tgtgacactg cctagccaca gcacccggaa gctgcagacc 960
agaagccaga cctggctgga aagcagagag tacaccaagc acctgatccg ggtggaaaac 1020
tggatcttcc ggaaccccgg cttcgccctg gccgctgctg ctattgcttg gctgctgggc 1080
agcagcacca gccagaaagt gatctacctc gtgatgatcc tgctgatcgc ccctgcctac 1140
agcatccggt gtatcggcgt gtccaaccgg gacttcgtgg aaggcatgag cggcggcaca 1200
tgggtggacg tggtgctgga acatggcggc tgcgtgacag tgatggccca ggacaagccc 1260
accgtggaca tcgagctcgt gaccaccacc gtgtccaata tggccgaagt gcggagctac 1320
tgctacgagg ccagcatcag cgacatggcc agcgacagca gatgccctac acagggcgag 1380
gcctacctgg acaagcagtc cgacacccag tacgtgtgca agcggaccct ggtggataga 1440
ggctggggca atggctgcgg cctgtttggc aagggcagcc tcgtgacctg cgccaagttc 1500
gcctgcagca agaagatgac cggcaagagc atccagcccg agaacctgga ataccggatc 1560
atgctgagcg tgcacggcag ccagcactcc ggcatgatcg tgaacgacac cggccacgag 1620
acagacgaga accgggccaa ggtggaaatc acccccaaca gccctagagc cgaggccaca 1680
ctgggcggct ttggatctct gggcctggac tgcgagccta gaaccggcct ggatttcagc 1740
gacctgtact acctgaccat gaacaacaaa cactggctgg tgcacaaaga gtggttccac 1800
gacatccccc tgccctggca tgccggcgct gatacaggca caccccactg gaacaacaaa 1860
gaggccctgg tggagttcaa ggacgcccac gccaagaggc agaccgtggt ggtgctggga 1920
tctcaggaag gcgccgtgca tacagctctg gctggcgccc tggaagccga aatggatggc 1980

-continued

```
gctaagggca gactgtccag cggccacctg aagtgccggc tgaagatgga caagctgcgg   2040

ctgaagggcg tgtcctacag cctgtgtacc gccgccttca ccttcaccaa gatccccgcc   2100

gagacactgc acggcaccgt gactgtggaa gtgcagtacg ccggcaccga cggcccttgt   2160

aaagtgcctg ctcagatggc cgtggatatg cagaccctga cccctgtggg caggctgatc   2220

accgccaacc ctgtgatcac cgagagcacc gagaacagca agatgatgct ggaactggac   2280

ccacccttcg gcgacagcta catcgtgatc ggcgtgggag agaagaagat cacccaccac   2340

tggcacagaa gcggcagcac catcggcaag gcctttgagg ctacagtgcg gggagccaag   2400

agaatggccg tgctgggaga taccgcctgg gactttggct ctgtgggcgg agccctgaac   2460

tctctgggca agggaatcca ccagatcttc ggcgctgcct tcaagagcct gttcggcggc   2520

atgagctggt tcagccagat cctgatcggc accctgctga tgtggctggg cctgaacacc   2580

aagaacggct ccatcagcct gatgtgcctg gctctgggag gcgtgctgat cttcctgagc   2640

acagccgtgt ccgcc                                                    2655
```

<210> SEQ ID NO 14
<211> LENGTH: 2709
<212> TYPE: DNA
<213> ORGANISM: Artificial Sequence
<220> FEATURE:
<223> OTHER INFORMATION: CMVTetO v1 promoter operably linked to ME Zika antigen

<400> SEQUENCE: 14

```
tcaatattgg ccattagcca tattattcat tggttatata gcataaatca atattggcta     60

ttggccattg catacgttgt atccatatca taatatgtac atttatattg gctcatgtcc    120

aacattaccg ccatgttgac attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtacg ccccctattg acgtcaatga    420

cggtaaatgg cccgcctggc attatgccca gtacatgacc ttatgggact ttcctacttg    480

gcagtacatc tacgtattag tcatcgctat taccatggtg atgcggtttt ggcagtacat    540

caatgggcgt ggatagcggt ttgactcacg gggatttcca agtctccacc ccattgacgt    600

caatgggagt ttgttttggc accaaaatca acgggacttt ccaaaatgtc gtaacaactc    660

cgccccattg acgcaaatgg gcggtaggcg tgtacggtgg gaggtctata taagcagagc    720

tctccctatc agtgatagag atctccctat cagtgataga gatcgtcgac gagctcgttt    780

agtgaaccgt cagatcgcct ggagacgcca tccacgctgt tttgacctcc atagaagaca    840

ccgggaccga tccagcctcc gcggccggga acggtgcatt ggaagcttgg taccgccacc    900

atgggcaaaa gatccgccgg cagcatcatg tggctggcca gtctggctgt cgtgatcgcc    960

tgtgctggcg ccgctgtgac actgcctagc cacagcaccc ggaagctgca gaccagaagc   1020

cagacctggc tggaaagcag agagtacacc aagcacctga tccgggtgga aaactggatc   1080

ttccggaacc ccggcttcgc cctggccgct gctgctattg cttggctgct gggcagcagc   1140

accagccaga aagtgatcta cctcgtgatg atcctgctga tcgcccctgc ctacagcatc   1200

cggtgtatcg gcgtgtccaa ccgggacttc gtggaaggca tgagcggcgg cacatgggtg   1260

gacgtggtgc tggaacatgg cggctgcgtg acagtgatgg cccaggacaa gcccaccgtg   1320
```

gacatcgagc tcgtgaccac caccgtgtcc aatatggccg aagtgcggag ctactgctac 1380
gaggccagca tcagcgacat ggccagcgac agcagatgcc ctacacaggg cgaggcctac 1440
ctggacaagc agtccgacac ccagtacgtg tgcaagcgga ccctggtgga tagaggctgg 1500
ggcaatggct gcggcctgtt tggcaagggc agcctcgtga cctgcgccaa gttcgcctgc 1560
agcaagaaga tgaccggcaa gagcatccag cccgagaacc tggaataccg gatcatgctg 1620
agcgtgcacg gcagccagca ctccggcatg atcgtgaacg acaccggcca cgagacagac 1680
gagaaccggg ccaaggtgga aatcaccccc aacagcccta gagccgaggc cacactgggc 1740
ggctttggat ctctgggcct ggactgcgag cctagaaccg gcctggattt cagcgacctg 1800
tactacctga ccatgaacaa caaacactgg ctggtgcaca aagagtggtt ccacgacatc 1860
cccctgccct ggcatgccgg cgctgataca ggcacacccc actggaacaa caaagaggcc 1920
ctggtggagt tcaaggacgc ccacgccaag aggcagaccg tggtggtgct gggatctcag 1980
gaaggcgccg tgcatacagc tctggctggc gccctggaag ccgaaatgga tggcgctaag 2040
ggcagactgt ccagcggcca cctgaagtgc cggctgaaga tggacaagct gcggctgaag 2100
ggcgtgtcct acagcctgtg taccgccgcc ttcaccttca ccaagatccc cgccgagaca 2160
ctgcacggca ccgtgactgt ggaagtgcag tacgccggca ccgacggccc ttgtaaagtg 2220
cctgctcaga tggccgtgga tatgcagacc ctgacccctg tgggcaggct gatcaccgcc 2280
aaccctgtga tcaccgagag caccgagaac agcaagatga tgctggaact ggacccaccc 2340
ttcggcgaca gctacatcgt gatcggcgtg ggagagaaga agatcaccca ccactggcac 2400
agaagcggca gcaccatcgg caaggccttt gaggctacag tgcggggagc caagagaatg 2460
gccgtgctgg gagataccgc ctgggacttt ggctctgtgg gcggagccct gaactctctg 2520
ggcaagggaa tccaccagat cttcggcgct gccttcaaga gcctgttcgg cggcatgagc 2580
tggttcagcc agatcctgat cggcaccctg ctgatgtggc tgggcctgaa caccaagaac 2640
ggctccatca gcctgatgtg cctggctctg ggaggcgtgc tgatcttcct gagcacagcc 2700
gtgtccgcc 2709

<210> SEQ ID NO 15
<211> LENGTH: 31171
<212> TYPE: DNA
<213> ORGANISM: Artificial Sequence
<220> FEATURE:
<223> OTHER INFORMATION: Ad26.ZIKV.002 adenoviral vector

<400> SEQUENCE: 15
catcatcaat aatatacccc acaaagtaaa caaaagttaa tatgcaaatg agcttttgaa 60
ttttaacggt tttggggcgg agccaacgct gattggacga gaaacggtga tgcaaatgac 120
gtcacgacgc acggctaacg gtcgccgcgg aggcgtggcc tagcccggaa gcaagtcgcg 180
gggctgatga cgtataaaaa agcggacttt agacccggaa acggccgatt ttcccgcggc 240
cacgcccgga tatgaggtaa ttctgggcgg atgcaagtga aattaggtca ttttggcgcg 300
aaaactgaat gaggaagtga aaagcgaaaa ataccggtcc ctcccagggc ggaatattta 360
ccgagggccg agagactttg accgattacg tgggggtttc gattgcggtg ttttttcgc 420 gaatttccgc gtccgtgtca aagtccggtg tttatgtcac agatcagctg acctaggtgg 480
tcaatattgg ccattagcca tattattcat tggttatata gcataaatca atattggcta 540
ttggccattg catacgttgt atccatatca taatatgtac atttatattg gctcatgtcc 600
aacattaccg ccatgttgac attgattatt gactagttat taatagtaat caattacggg 660

-continued

```
gtcattagtt catagcccat atatggagtt ccgcgttaca taacttacgg taaatggccc    720
gcctggctga ccgcccaacg acccccgccc attgacgtca ataatgacgt atgttcccat    780
agtaacgcca atagggactt tccattgacg tcaatgggtg gagtatttac ggtaaactgc    840
ccacttggca gtacatcaag tgtatcatat gccaagtacg ccccctattg acgtcaatga    900
cggtaaatgg cccgcctggc attatgccca gtacatgacc ttatgggact ttcctacttg    960
gcagtacatc tacgtattag tcatcgctat taccatggtg atgcggtttt ggcagtacat   1020
caatgggcgt ggatagcggt ttgactcacg gggatttcca agtctccacc ccattgacgt   1080
caatgggagt ttgttttggc accaaaatca acgggacttt ccaaaatgtc gtaacaactc   1140
cgccccattg acgcaaatgg gcggtaggcg tgtacggtgg gaggtctata taagcagagc   1200
tcgtttagtt ccctatcagt gatagagaag acgccatcca cgctgttttg acctccatag   1260
aagacaccgg gaccgatcca gcctccgcgg ccgggaacgg tgcattggaa gcttggtacc   1320
gccaccatgg gcaaaagatc cgccggcagc atcatgtggc tggccagtct ggctgtcgtg   1380
atcgcctgtg ctggcgccgc tgtgacactg cctagccaca gcacccggaa gctgcagacc   1440
agaagccaga cctggctgga aagcagagag tacaccaagc acctgatccg ggtggaaaac   1500
tggatcttcc ggaaccccgg cttcgccctg gccgctgctg ctattgcttg gctgctgggc   1560
agcagcacca gccagaaagt gatctacctc gtgatgatcc tgctgatcgc ccctgcctac   1620
agcatccggt gtatcggcgt gtccaaccgg gacttcgtgg aaggcatgag cggcggcaca   1680
tgggtggacg tggtgctgga acatggcggc tgcgtgacag tgatggccca ggacaagccc   1740
accgtggaca tcgagctcgt gaccaccacc gtgtccaata tggccgaagt gcggagctac   1800
tgctacgagg ccagcatcag cgacatggcc agcgacagca gatgccctac acagggcgag   1860
gcctacctgg acaagcagtc cgacacccag tacgtgtgca agcggaccct ggtggataga   1920
ggctggggca atggctgcgg cctgtttggc aagggcagcc tcgtgacctg cgccaagttc   1980
gcctgcagca agaagatgac cggcaagagc atccagcccg agaacctgga ataccggatc   2040
atgctgagcg tgcacggcag ccagcactcc ggcatgatcg tgaacgacac cggccacgag   2100
acagacgaga accgggccaa ggtggaaatc acccccaaca gccctagagc cgaggccaca   2160
ctgggcggct ttggatctct gggcctggac tgcgagccta gaaccggcct ggatttcagc   2220
gacctgtact acctgaccat gaacaacaaa cactggctgg tgcacaaaga gtggttccac   2280
gacatccccc tgccctggca tgccggcgct gatacaggca caccccactg gaacaacaaa   2340
gaggccctgg tggagttcaa ggacgcccac gccaagaggc agaccgtggt ggtgctggga   2400
tctcaggaag gcgccgtgca tacagctctg gctggcgccc tggaagccga aatggatggc   2460
gctaagggca gactgtccag cggccacctg aagtgccggc tgaagatgga caagctgcgg   2520
ctgaagggcg tgtcctacag cctgtgtacc gccgccttca ccttcaccaa gatccccgcc   2580
gagacactgc acggcaccgt gactgtggaa gtgcagtacg ccggcaccga cggcccttgt   2640
aaagtgcctg ctcagatggc cgtggatatg cagaccctga cccctgtggg caggctgatc   2700
accgccaacc ctgtgatcac cgagagcacc gagaacagca agatgatgct ggaactggac   2760
ccacccttcg gcgacagcta catcgtgatc ggcgtgggag agaagaagat cacccaccac   2820
tggcacagaa gcggcagcac catcggcaag gcctttgagg ctacagtgcg gggagccaag   2880
agaatggccg tgctgggaga taccgcctgg gactttggct ctgtgggcgg agccctgaac   2940
tctctgggca agggaatcca ccagatcttc ggcgctgcct tcaagagcct gttcggcggc   3000
```

-continued

```
atgagctggt tcagccagat cctgatcggc accctgctga tgtggctggg cctgaacacc   3060
aagaacggct ccatcagcct gatgtgcctg gctctgggag gcgtgctgat cttcctgagc   3120
acagccgtgt ccgcctgagc tagcgttaac ggatcctcta gacgagatcc gaacttgttt   3180
attgcagctt ataatggtta caaataaagc aatagcatca caaatttcac aaataaagca   3240
tttttttcac tgcattctag ttgtggtttg tccaaactca tcaatgtatc ttatcatgtc   3300
tagatccagg taggtttgag tagtgggcgt ggctaaggtg actataaagg cgggtgtctt   3360
acgagggtct tttgctttt ctgcagacat catgaacggg actggcgggg ccttcgaagg   3420
ggggcttttt agcccttatt tgacaacccg cctgccggga tgggccggag ttcgtcagaa   3480
tgtgatggga tcgacggtgg atgggcgccc agtgcttcca gcaaattcct cgaccatgac   3540
ctacgcgacc gtggggaact cgtcgctcga cagcaccgcc gcagccgcgg cagccgcagc   3600
cgccatgaca gcgacgagac tggcctcgag ctacatgccc agcagcggta gtagcccctc   3660
tgtgcccagt tccatcatcg ccgaggagaa actgctggcc ctgctggccg agctggaagc   3720
cctgagccgc cagctggccg ccctgaccca gcaggtgtcc gagctccgcg aacagcagca   3780
gcagcaaaat aaatgattca ataaacacag attctgattc aaacagcaaa gcatctttat   3840
tatttatttt ttcgcgcgcg gtaggccctg gtccacctct cccgatcatt gagagtgcgg   3900
tggatttttt ccaggacccg gtagaggtgg gattggatgt tgaggtacat gggcatgagc   3960
ccgtcccgtg ggtggaggta gcaccactgc atggcctcgt gctctggggt cgtgttgtag   4020
atgatccagt catagcaggg gcgctgggcg tggtgctgga tgatgtcctt gaggaggaga   4080
ctgatggcca cggggagccc cttggtgtag gtgttggcaa aacggttgag ctgggaggga   4140
tgcatgcggg gggagatgat gtgcagtttg gcctggatct tgaggttggc gatgttgcca   4200
cccagatccc gccgggggtt catgttgtgc aggaccacca gaacggtgta gcccgtgcac   4260
ttggggaact tgtcatgcaa cttggaaggg aatgcgtgga agaatttgga gacgcccttg   4320
tgcccgccca ggttttccat gcactcatcc atgatgatgg caatgggccc gtgggctgcg   4380
gctttggcaa agacgtttct ggggtcagag acatcgtaat tatgctcctg ggtgagatca   4440
tcataagaca ttttaatgaa tttggggcgg agggtgccag attgggggac gatggttccc   4500
tcgggccccg gggcgaagtt cccctcgcag atctgcatct cccaggcttt catctcggag   4560
ggggggatca tgtccacctg cggggcgatg aaaaaaacgg tttccggggc gggggtgatg   4620
agctgcgagg agagcaggtt tctcaacagc tgggacttgc cgcacccggt cgggccgtag   4680
atgaccccga tgacgggttg caggtggtag ttcaaggaca tgcagctgcc gtcgtcccgg   4740
aggagggggg ccacctcgtt gagcttgtct ctgacttgga ggttttcccg gacgagctcg   4800
ccgaggaggc ggtccccgcc cagcgagaga agctcttgca gggaagcaaa gtttttcagg   4860
ggcttgagcc cgtcggccat gggcatcttg gcgagggtct gcgagaggag ctccaggcgg   4920
tcccagagct cggtgacgtg ctctacggca tctcgatcca gcagacttcc tcgtttcggg   4980
ggttgggacg actgcgactg tagggcacga gacgatgggc gtccagcgcg gccagcgtca   5040
tgtccttcca gggtctcagg gtccgcgtga gggtggtctc cgtcacggtg aaggggtggg   5100
ccgcgggctg ggcgcttgca agggtgcgct tgagactcat cctgctggtg ctgaaacggg   5160
cacggtcttc gccctgcgcg tcggcgagat agcagttgac catgagctcg tagttgaggg   5220
cctcggcggc gtggcccttg gcgcggagct tgcccttgga agagcgcccg caggcgggac   5280
agaggaggga ttgcagggcg tagagcttgg gcgcgagaaa gacggactcg gggcgaaggg   5340
cgtccgctcc gcagtgggcg cagacggtct cgcactcgac tagccaggtg agctcgggct   5400
```

gctcggggtc aaaaaccagt tttcccccgt tctttttgat gcgcttctta cctcgcgtct 5460
ccatgagtct gtgtccgcgc tcggtgacaa acaggctgtc tgtgtccccg tagacggact 5520
tgatgggcct gtcctgcagg ggcgtcccgc ggtcctcctc gtagagaaac tcagaccact 5580
ctgagacgaa ggcgcgcgtc cacgccaaga caaaggaggc cacgtgcgag ggtagcggt 5640
cgttgtccac caggggggtcc acctttttcca cggtatgcag gcacatgtcc ccctcctccg 5700
catccaagaa ggtgattggc ttgtaggtgt aggccacgtg acctggggtt cccgacgggg 5760
gggtataaaa gggggcgggt ctgtgctcgt cctcactctc ttccgcgtcg ctgtccacga 5820
gcgccagctg ttggggtagg tattccctct caagagcggg catgacctcg gcactcaggt 5880
tgtcagtttc tagaaacgag gaggatttga tgtgggcctg ccctgccgcg atgcttttta 5940
ggagactttc atccatctgg tcagaaaaga ctattttttt attgtcaagc ttggtggcga 6000
aggagccata gagggcgttt gagagaagct tggcgatgga tctcatggtc tgatttttgt 6060
cacggtcggc gcgctccttg gccgcgatgt tgagctggac atattcgcgc gcgacacact 6120
tccattcggg gaagacggtg gtgcgctcgt cgggcacgat cctgacgcgc cagccgcggt 6180
tatgcagggt gaccaggtcc acgctggtgg ccacctcgcc gcgcaggggc tcgttggtcc 6240
agcagagtct gccgcccttg cgcgagcaga acgggggcag cacatcaagc agatgctcgt 6300
caggggggtc cgcatcgatg gtgaagatgc ccggacagag ttccttgtca aaataatcga 6360
tttttgagga tgcatcgtcc aaggccatct gccactcgcg ggcggccagc gctcgctcgt 6420
aggggttgag gggcggaccc caaggcatgg gatgcgtgag ggcggaggcg tacatgccgc 6480
agatgtcata gacatagatg ggctccgaga ggatgccgat gtaggtggga tagcagcgcc 6540
ccccgcggat gcttgcgcgc acgtagtcat acaactcgtg cgagggggcc aagaaggcgg 6600
ggccgagatt ggtgcgctgg ggctgctcgg cgcggaagac gatctggcga aagatggcgt 6660
gcgagttgga ggagatggtg ggccgttgga agatgttaaa gtgggcgtga ggcaggcgga 6720
ccgagtcgcg gatgaagtgc gcgtaggagt cttgcagctt ggcgacgagc tcggcggtga 6780
cgaggacgtc catggcgcag tagtccagcg tttcgcggat gatgtcataa ctcgcctctc 6840
ctttcttctc ccacagctcg cggttgaggg cgtattcctc gtcatccttc cagtactccc 6900
ggagcgggaa tcctcgatcg tccgcacggt aagagcccag catgtagaaa tggttcacgg 6960
ccttgtaggg acagcagccc ttctccacgg ggagggcgta agcttgagcg gccttgcgga 7020
gcgaggtgtg cgtcagggca aaggtgtccc tgaccatgac tttcaagaac tggtacttga 7080
agtccgagtc gtcgcagccg ccgtgctccc agagctcgaa atcggtgcgc ttcttcgaga 7140
gggggttagg cagagcgaaa gtgacgtcat tgaagagaat cttgcctgcc cgcggcatga 7200
aattgcgggt gatgcggaaa gggcccggga cggaggctcg gttgttgatg acctgggcgg 7260
cgaggacgat ctcgtcaaag ccgttgatgt tgtgcccgac gatgtagagt tccatgaatc 7320
gcgggcggcc tttgatgtgc ggcagctttt tgagctcctc gtaggtgagg tcctcggggc 7380
attgcaggcc gtgctgctcg agcgcccact cctggagatg tgggttggct tgcatgaagg 7440
aagcccagag ctcgcgggcc atgagggtct ggagctcgtc gcgaaagagg cggaactgct 7500
ggcccacggc catcttttct ggggtgacgc agtagaaggt gagggggtcc cgctcccagc 7560
gatcccagcg taaacgcacg gcgagatcgc gagcgagggc gaccagctct gggtccccgg 7620
agaatttcat gaccagcatg aaggggacga gctgcttgcc gaaggacccc atccaggtgt 7680
aggtttctac atcgtaggtg acaaagagcc gctccgtgcg aggatgagag ccgattggga 7740

-continued

```
agaactggat ttcctgccac cagttggacg agtggctgtt gatgtgatga aagtagaaat   7800
cccgccggcg aaccgagcac tcgtgctgat gcttgtaaaa gcgtccgcag tactcgcagc   7860
gctgcacggg ctgtacctca tccacgagat acacagcgcg tcccttgagg aggaacttca   7920
ggagtggcgg ccctggctgg tggttttcat gttcgcctgc gtgggactca ccctggggct   7980
cctcgaggac ggagaggctg acgagcccgc gcgggagcca ggtccagatc tcggcgcggc   8040
gggggcggag agcgaagacg agggcgcgca gttgggagct gtccatggtg tcgcggagat   8100
ccaggtccgg gggcagggtt ctgaggttga cctcgtagag gcgggtgagg gcgtgcttga   8160
gatgcagatg gtacttgatt tctacgggtg agttggtggt cgtgtccacg cattgcatga   8220
gcccgtagct gcgcggggcc acgaccgtgc cgcggtgcgc ttttagaagc ggtgtcgcgg   8280
acgcgctccc ggcggcagcg gcggttccgg ccccgcgggc aggggcggca gaggcacgtc   8340
ggcgtggcgc tcgggcaggt cccggtgctg cgccctgaga gcgctggcgt gcgcgacgac   8400
gcggcggttg acatcctgga tctgccgcct ctgcgtgaag accacgggcc ccgtgacttt   8460
gaacctgaaa gacagttcaa cagaatcaat ctctgcgtca ttgacggcgg cctgacgcag   8520
gatctcttgc acgtcgcccg agttgtcctg gtaggcgatc tcggacatga actgttcgat   8580
ctcctcctcc tggagatcgc cgcggcccgc gcgctccacg gtggcggcga ggtcattgga   8640
gatgcgaccc atgagctgcg agaaggcgcc caggccgctc tcgttccaga cgcggctgta   8700
gaccacgtcc ccgtcggcgt cgcgcgcgcg catgaccacc tgcgcgaggt tgagctccac   8760
gtgccgcgca aagacggcgt agttgcgcag gcgctggaag aggtagttga gggtggtggc   8820
gatgtgctcg gtgacgaaga agtacatgat ccagcggcgc aggggcatct cgctgatgtc   8880
gccgatggct tccagccttt ccatggcctc gtagaagtcc acggcgaagt tgaaaaactg   8940
ggcgttgcgg gccgagaccg tgagctcgtc ttccaggagc cggatgagtt cggcgatggt   9000
ggcgcgcacc tcgcgctcga aatccccggg ggcctcctcc tcttcctctt cttccatgac   9060
gacctcttct tctatttctt cctctggggg cggtggtggt ggcgggggcc gacgacgacg   9120
gcgacgcacc gggagacggt cgacgaagcg ctcgatcatc tccccgcggc ggcgacgcat   9180
ggtttcggtg acggcgcgac cccgttcgcg aggacgcagc gtgaagacgc cgccggtcat   9240
ctcccggtaa tggggcgggt ccccattggg cagcgatagg gcgctgacga tgcatcttat   9300
caattgcggt gtaggggacg tgagcgcgtc gagatcgacc ggatcggaga atctttcgag   9360
gaaagcgtct agccaatcgc agtcgcaagg taagctcaaa cacgtagcag ccctgcggac   9420
gctgttagaa ttgcggttgc tgatgatgta attgaagtag gcgtttttga ggcggcggat   9480
ggtggcgagg aggaccaggt ccttgggtcc agcttgctgg atgcggagcc gctcggccat   9540
gccccaggcc tggccctgac accggctcag gttcttgtag tagtcatgca tgagcctctc   9600
aatgtcatca ctggctgagg cggagtcttc catgcgggtg accccgacgc ccctgagcgg   9660
ctgcacgagc gccaggtcgg cgacgacgcg ctcggcgagg atggcctgtt gcacgcgggt   9720
gagggtgtcc tggaagtcgt ccatgtcgac gaagcggtga taggccccgg tgttgatggt   9780
gtaggtgcag ttggccatga gcgaccagtt gacggtctgc aggcctggct gcacgacctc   9840
ggagtacctg agccgcgaga aggcgcgcga gtcgaagacg tagtcgttgc aggtgcgcac   9900
gaggtactgg tatccgacta ggaagtgcgg cggcggctgg cggtagagcg gccagcgctg   9960
ggtggccggc gcgcccgggg ccaggtcctc gagcatgagg cggtggtagc cgtagaggta  10020
gcgggacatc caggtgatgc cggcggcggt ggtggaggcg cgcgggaact cgcggacgcg  10080
gttccagatg ttgcgcagcg gcaggaaata gtccatggtc ggcacggtct ggccggtgag  10140
```

-continued

```
acgcgcgcag tcattgacgc tctagaggca aaaacgaaag cggttgagcg ggctcttcct  10200
ccgtagcctg gcggaacgca aacgggttag gccgcgtgtg taccccggtt cgagtcccct  10260
cgaatcaggc tggagccgcg actaacgtgg tattggcact cccgtctcga cccgagcccg  10320
atagccgcca ggatacggcg gagagccctt tttgccggcc gagtggggtc gctagacttg  10380
aaagcgaccg aaaaccctgc cgggtagtgg ctcgcgcccg tagtctggag aagcatcgcc  10440
agggttgagt cgcggcagaa cccggttcga ggacggccgc ggcgagcggg acttggtcac  10500
cccgccgata taaagaccca cagccagccg acttctccag ttacgggagc gagcccccct  10560
ttttcttttt gccagatgca tcccgtcctg cgccaaatgc gtcccacccc cccggcgacc  10620
accgcgaccg cggccgtagc aggcgccggc gctagccagc caccacagac agagatggac  10680
ttggaagagg gcgaagggct ggcaagactg gggcgccgt ccccggagcg acatccccgc  10740
gtgcagctgc agaaggacgt gcgcccggcg tacgtgccta cgcagaacct gttcagggac  10800
cgcagcgggg aggagcccga ggagatgcgc gactgccggt ttcgggcggg cagggagctg  10860
cgcgagggcc tggaccgcca gcgcgtgctg cgcgacgagg atttcgagcc gaacgagcag  10920
acggggatca gccccgcacg cgcgcacgtg gcggcagcca acctggtgac ggcctacgag  10980
cagacggtga agcaggagcg caacttccaa aagagtttca acaaccacgt gcgcaccctg  11040
atcgcgcgcg aggaggtggc cctgggcctg atgcacctgt gggacctggc ggaggccatc  11100
gtgcagaacc cggacagcaa gcctctgacg gcgcagctgt tcctggtggt gcagcacagc  11160
agggacaacg aggcgttcag ggaggcgctg ctgaacatcg ccgagcccga gggtcgctgg  11220
ctgctggagc tgattaacat cttgcagagc atcgtagtgc aggagcgcag cctgagcctg  11280
gccgagaagg tggcggcgat caactactcg gtgctgagcc tgggcaagtt ttacgcgcgc  11340
aagatttaca agacgccgta cgtgcccata gacaaggagg tgaagataga cagcttttac  11400
atgcgcatgg cgctcaaggt gctgacgctg agcgacgacc tgggcgtgta ccgcaacgac  11460
cgcatccaca aggccgtgag cacgagccgg cggcgcgagc tgagcgaccg cgagctgatg  11520
ctgagtctgc gccgggcgct ggtagggggc gccgccggcg gcgaggagtc ctacttcgac  11580
atgggtgcgg acctgcattg gcagccgagc cggcgcgcct tggaggccgc ctacggttca  11640
gaggacttgg atgaggaaga ggaagaggag gaggatgcac ccgctgcggg gtactgacgc  11700
ctccgtgatg tgtttttaga tgtcccagca agccccggac cccgccataa gggcggcgct  11760
gcaaagccag ccgtccggtc tagcatcgga cgactgggag gccgcgatgc aacgcatcat  11820
ggccctgacg acccgcaacc ccgagtcctt tagacaacag ccgcaggcca acagactctc  11880
ggccattctg gaggcggtgg tcccctctcg gaccaacccc acgcacgaga aggtgctggc  11940
gatcgtgaac gcgctggcgg agaacaaggc catccgtccc gacgaggccg ggctggtgta  12000
caacgccctg ctggagcgcg tgggccgcta caacagcacg aacgtgcagt ccaacctgga  12060
tcggctggtg acggacgtgc gcgaggccgt ggcgcagcgc gagcggttca agaacgaggg  12120
cctgggctcg ctggtggcgc tgaacgcctt cctggcgacg cagccggcga acgtgccgcg  12180
cgggcaggac gattacacca actttatcag cgcgctgcgg ctgatggtga ccgaggtgcc  12240
ccagagcgag gtgtaccagt ctggcccgga ctactttttc cagacgagcc ggcagggctt  12300
gcagacggtg aacctgagcc aggctttcaa gaatctgcgc gggctgtggg gcgtgcaggc  12360
gcccgtgggc gaccggtcaa cggtgagcag cttgctgacg cccaactcgc ggctgctgct  12420
gctgctgatc gcgcccttca ccgacagcgg cagcgtgaac cgcaactcgt acctgggcca  12480
```

-continued

```
tctgctgacg ctgtaccgcg aggccatagg ccaggcgcag gtggacgagc agaccttcca  12540
ggagatcact agcgtgagcc gcgcgctggg gcagaacgac accgacagtc tgagggccac  12600
cctgaacttt ttgctgacca atagacagca gaagatcccg gcgcagtacg cactgtcggc  12660
cgaggaggaa aggattctga gatatgtgca gcagagcgta gggctgttcc tgatgcagga  12720
gggtgccacc cccagcgccg cgctggacat gaccgcgcgc aacatggaac ctagcatgta  12780
cgccgccaac cggccgttca tcaataagct gatggactac ttgcaccgcg cggcggccat  12840
gaacacggac tactttacca acgccatcct gaacccgcac tggctcccgc cgccggggtt  12900
ctacacgggc gagtacgaca tgcccgaccc caacgacggg ttcctgtggg acgacgtgga  12960
cagcgcggtg ttctcgccga cctttcaaaa gcgccaggag gcgccgccga gcgagggcgc  13020
ggtggggagg agcccctttc ctagcttagg gagtttgcat agcttgccgg gctcggtgaa  13080
cagcggcagg gtgagccggc cgcgcttgct gggcgaggac gagtacctga acgactcgct  13140
gctgcagccg ccgcgggcca agaacgccat ggccaataac gggatagaga gtctggtgga  13200
caaactgaac cgctggaaga cctacgctca ggaccatagg gacgcgcccg cgccgcggcg  13260
acagcgccac gaccggcagc ggggcctggt gtgggacgac gaggactcgg ccgacgatag  13320
cagcgtgttg gacttgggcg ggagcggtgg ggtcaacccg ttcgcgcatc tgcagcccaa  13380
actggggcga cggatgtttt gaatgaaata aaactcacca aggccatagc gtgcgttctc  13440
ttccttgtta gagatgaggc gcgcggtggt gtcttcctct cctcctccct cgtacgagag  13500
cgtgatggcg caggcgaccc tggaggttcc gtttgtgcct ccgcggtata tggctcctac  13560
ggagggcaga aacagcattc gttactcgga gctggctccg cagtacgaca ccactcgcgt  13620
gtacttggtg gacaacaagt cggcggacat cgcttccctg aactaccaaa acgaccacag  13680
caacttcctg accacggtgg tgcagaacaa cgatttcacc cccgccgagg ccagcacgca  13740
gacgataaat tttgacgagc ggtcgcggtg gggcggtgat ctgaagacca ttctgcacac  13800
taacatgccc aatgtgaacg agtacatgtt caccagcaag tttaaggcgc gggtgatggt  13860
gtctaggaag catccagagg gggtagttga aacagatttg agtcaggata agcttgaata  13920
tgagtggttt gagtttaccc tgcccgaggg aaacttttcc gagaccatga ccatagacct  13980
gatgaacaac gccatcttgg aaaactactt gcaagtgggg cggcagaatg gcgtgctgga  14040
gagcgatatc ggagtcaagt ttgacagcag aaatttcaag ctgggctggg acccggtgac  14100
caagctggtg atgccagggg tctacaccta cgaggccttc cacccggacg tggtgctgct  14160
gccgggctgc ggggtggact tcaccgagag ccgcctgagc aacctcctgg gcattcgcaa  14220
gaagcaacct ttccaagagg gcttcagaat catgtatgag gatctagaag gtggcaacat  14280
ccccgccctc cttgatgtgc ccaagtactt ggaaagcaag aagaaagttg aagacgaaac  14340
taaaaatgca gctgcggcca cagccgatac aaccactagg ggtgatacat ttgcaactcc  14400
agcgcaagag acagcagctg ataagaaggt agaagtcttg cccattgaaa aggatgagag  14460
tggtagaagt tacaacctga tccaggggac ccacgacacg ctgtaccgca gttggtacct  14520
gtcctatacc tacggggacc ccgagaaggg ggtgcagtcg tggacgctgc tcaccacccc  14580
ggacgttacc tgcggcgcgg agcaagtcta ctggtcactg ccggacctca tgcaagaccc  14640
cgtcaccttc cgctccaccc agcaagtcag caactacccc gtggtcggcg ccgagctcat  14700
gcccttccgc gccaagagct tttacaacga cctcgccgtc tactcccagc tcatccgcag  14760
ctacacctcc ctcacccacg tcttcaaccg cttccccgac aaccagatcc tctgccgccc  14820
gcccgcgccc accatcacca ccgtcagtga aaacgtgcct gctctcacag atcacgggac  14880
```

-continued

```
gctaccgctg cgcagcagta tccgcggagt ccagcgagtg accgtcactg acgcccgtcg  14940
ccgcacctgt ccctacgtct acaaggccct gggcatagtc gcgccgcgcg tgctttccag  15000
tcgcaccttc taaaaaaatg tctattctca tctcgcccag caataacacc ggctggggtc  15060
ttactagacc cagcaccatg tacggaggag ccaagaagcg ctcccagcag caccccgtcc  15120
gcgtccgcgg ccacttccgc gctccctggg gcgcatacaa gcgcgggcgg acttccaccg  15180
ccgccgtgcg caccaccgtc gacgacgtca tcgactcggt ggtcgccgac gcgcgcaact  15240
atacccccgc cccctccacc gtggacgcgg tcatcgacag cgtggtggcc gacgcgcgcg  15300
actatgccag acgcaagagc cggcggcgac ggatcgccag gcgccaccgg agcacgcccg  15360
ccatgcgcgc cgcccgggct ctgctgcgcc gcgccagacg cacgggccgc cgggccatga  15420
tgcgagccgc gcgccgcgct gccactgcac ccaccccgc aggcaggact cgcagacgag  15480
cggccgccgc cgccgctgcg gccatctcta gcatgaccag acccaggcgc ggaaacgtgt  15540
actgggtgcg cgactccgtc acgggcgtgc gcgtgcccgt gcgcacccgt cctcctcgtc  15600
cctgatctaa tgcttgtgtc ctcccccgca agcgacgatg tcaaagcgca aaatcaagga  15660
ggagatgctc caggtcgtcg ccccggagat ttacggacca ccccaggcgg accagaaacc  15720
ccgcaaaatc aagcgggtta aaaaaaagga tgaggtggac gagggggcag tagagtttgt  15780
gcgcgagttc gctccgcggc ggcgcgtaaa ttggaagggg cgcagggtgc agcgcgtgtt  15840
gcggcccggc acggcggtgg tgttcacgcc cggcgagcgg tcctcggtca ggagcaagcg  15900
tagctatgac gaggtgtacg gcgacgacga catcctggac caggcggcgg agcgggcggg  15960
cgagttcgcc tacgggaagc ggtcgcgcga agaggagctg atctcgctgc cgctggacga  16020
aagcaacccc acgccgagcc tgaagcccgt gaccctgcag caggtgctgc cccaggcggt  16080
gctgctgccg agccgcgggg tcaagcgcga gggcgagagc atgtacccga ccatgcagat  16140
catggtgccc aagcgccggc gcgtggagga cgtgctggac accgtgaaaa tggatgtgga  16200
gcccgaggtc aaggtgcgcc ccatcaagca ggtggcgccg ggcctgggcg tgcaaaccgt  16260
ggacattcag atccccaccg acatggatgt cgacaaaaaa ccctcgacca gcatcgaggt  16320
gcaaaccgac ccctggctcc cagcctccac cgctaccgtc tccacttcta ccgccgccac  16380
ggctaccgag cctcccagga ggcgaagatg gggcgccgcc agccggctga tgcccaacta  16440
cgtgttgcat ccttccatca tcccgacgcc gggctaccgc ggcacccggt actacgccag  16500
ccgccggcgc ccagccagca aacgccgccg ccgcaccgcc acccgccgcc gtctggcccc  16560
cgcccgcgtg cgccgcgtga ccacgcgccg gggccgctcg ctcgttctgc ccaccgtgcg  16620
ctaccacccc agcatccttt aatccgtgtg ctgtgatact gttgcagaga gatggctctc  16680
acttgccgcc tgcgcatccc cgtcccgaat taccgaggaa gatcccgccg caggagaggc  16740
atggcaggca gcggcctgaa ccgccgccgg cggcgggcca tgcgcaggcg cctgagtggc  16800
ggctttctgc ccgcgctcat ccccataatc gccgcggcca ttggcacgat cccgggcata  16860
gcttccgttg cgctgcaggc gtcgcagcgc cgttgatgtg cgaataaagc ctctttagac  16920
tctgacacac ctggtcctgt atatttttag aatggaagac atcaattttg cgtccctggc  16980
tccgcggcac ggcacgcggc cgttcatggg cacctggaac gagatcggca ccagccagct  17040
gaacgggggc gccttcaatt ggagcagtgt ctggagcggg cttaaaaatt tcggctcgac  17100
gctccggacc tatgggaaca aggcctggaa tagtagcacg gggcagttgt tgagggaaaa  17160
gctcaaagac cagaacttcc agcagaaggt ggtggacggg ctggcctcgg gcattaacgg  17220
```

-continued ggtggtggac atcgcgaacc aggccgtgca gcgcgagata aacagccgcc tggacccgcg 17280
accgcccacg gtggtggaga tggaagatgc aactcttccg ccgcccaagg gcgagaagcg 17340
gccgcggccc gacgcggagg agacgatcct gcaggtggac gagccgccct cgtacgagga 17400
ggccgtcaag gccggcatgc ccaccacgcg catcatcgcg ccgctggcca cgggtgtaat 17460
gaaacccgcc acccttgacc tgcctccacc acccgcgccc gctccaccga aggcaactcc 17520
ggttgtgcag gcccccccgg tggcgaccgc cgtgcgccgc gtccccgccc gccgccaggc 17580
ccagaactgg cagagcacgc tgcacagtat cgtgggcctg ggagtgaaaa gtctgaagcg 17640
ccgccgatgc tattgagaga gaggaaagag gacactaaag ggagagctta acttgtatgt 17700
gccttaccgc cagagaacgc gcgaagatgg ccaccccctc gatgatgccg cagtgggcgt 17760
acatgcacat cgccgggcag gacgcctcgg agtacctgag cccgggtctg gtgcagtttg 17820
cccgcgccac cgacacgtac ttcagcctgg gcaacaagtt taggaacccc acggtggccc 17880
cgacccacga tgtgaccacg gaccggtccc agcgtctgac gctgcgcttc gtgcccgtgg 17940
atcgcgagga caccacgtac tcgtacaagg cgcgcttcac tctggccgtg ggcgacaacc 18000
gggtgctaga catggccagc acttactttg acatccgcgg cgtcctggac cgcggtccca 18060
gcttcaaacc ctactcgggc acggcctaca acagcctggc tcccaagggt gcccccaatc 18120
ccagtcagtg ggaaacaaaa gaaaagcaag gaactactgg aggagtgcag caagaaaaag 18180
atgtcacaaa aacatttggt gtggctgcca ccggcggaat taatataaca aaccagggtc 18240
tgttactagg aactgacgaa accgctgaga atggcaaaaa agacatttat gcagacaaga 18300
ctttccagcc agaacctcaa gttggagaag aaaactggca ggaaaatgaa gccttctatg 18360
gaggaagggc tcttaaaaag gacactaaaa tgaaaccatg ctatggatct tttgctagac 18420
ctactaatga gaaaggaggt caggcaaagt tcaaaccagt taatgaagga gaacaaccta 18480
aagatctgga tatagatttt gcttactttg acgtccctgg cggaagtcct ccagcaggtg 18540
gtagtgggga agaatacaaa gcagatataa ttttgtacac tgaaaatgtt aatcttgaaa 18600
caccagacac tcatgtggtt tacaagccag gaacttcaga taacagttca gaaatcaatc 18660
tggttcagca gtccatgcca aacagaccca actacattgg ctttagggac aactttgtag 18720
gtctcatgta ttacaacagc accggaaata tgggtgtgct ggctggtcag gcttctcagt 18780
tgaacgctgt ggtcgacttg caagacagaa acaccgagtt atcttaccag ctattgctag 18840
attctctggg tgacagaacc agatacttta gcatgtggaa ctctgcggtg gacagttacg 18900
atccagatgt caggatcatt gaaaatcacg gtgtggaaga tgaacttcca aactattgct 18960
tcccattgaa tggcactgga accaattcca cttatcaagg tgtaaagatt acaaatggta 19020
atgatggtgc tgaagaaagt gagtgggaga aagacgatgc aatttctaga caaaaccaaa 19080
tctgcaaggg caatgtctac gccatggaga tcaacctgca ggccaacctg tggaagagtt 19140
ttctgtactc gaacgtggcc ctgtacctgc ccgactccta caagtacacg ccggccaacg 19200
tcaagctgcc cgccaacacc aacacctacg agtacatgaa cggccgcgtg gtagccccct 19260
cgctggtgga cgcctacatc aacatcggcg cccgctggtc gttggacccc atggacaacg 19320
tcaacccctt caaccaccac cgcaatgcgg gcctgcgcta ccgctccatg ctgctgggca 19380
acggccgcta cgtgcccttc cacatccaag tgccccaaaa gttctttgcc atcaagaacc 19440
tgctcctgct cccgggctcc tacacctacg agtggaactt ccgcaaggac gtcaacatga 19500
tcctgcagag ttccctcggc aacgacctgc gcgtcgacgg cgcctccgtc cgcttcgaca 19560
gcgtcaacct atacgccact ttcttcccca tggcgcacaa caccgcttca accttggaag 19620

-continued

```
ccatgctgcg caacgacacc aacgaccagt ccttcaacga ctacctctcg gccgccaaca  19680
tgctctaccc catcccggcc aaggccacca acgtgcccat ctccatccca tcgcgcaact  19740
gggccgcctt ccgcggctgg agtttcaccc ggctcaagac caaggaaact ccttccctcg  19800
gctcgggttt cgacccctac tttgtctact cgggctccat cccctacctc gacgggacct  19860
tctacctcaa ccacaccttc aagaaggtct ccatcatgtt cgactcctcg gtcagctggc  19920
ccggcaacga ccggctgctc acgccgaacg agttcgagat caagcgcagc gtcgacgggg  19980
agggctacaa cgtggcccaa tgcaacatga ccaaggactg gttcctcgtc cagatgctct  20040
cccactacaa catcggctac cagggcttcc acgtgcccga gggctacaag gaccgcatgt  20100
actccttctt ccgcaacttc cagcccatga gcaggcaggt ggtcgatgag atcaactaca  20160
aggactacaa ggccgtcacc ctgcccttcc agcacaataa ctcgggcttc accggctacc  20220
tcgcacccac catgcgccag gggcagccct accccgccaa cttcccctac ccgctcatcg  20280
gtcagacagc cgtgccctcc gtcacccaga aaaagttcct ctgcgacagg gtcatgtggc  20340
gcatcccctt ctccagcaac ttcatgtcca tgggcgccct caccgacctg ggtcagaaca  20400
tgctctacgc caactcggcc cacgcgctcg acatgacctt cgaggtggac cccatggatg  20460
agcccaccct cctctatctt ctcttcgaag ttttcgacgt ggtcagagta caccagccgc  20520
accgcggcgt catcgaggcc gtctacctgc gcacgccctt ctccgccggc aacgccacca  20580
cctaagcatg agcggctcca gcgaacgaga gctcgcggcc atcgtgcgcg acctgggctg  20640
cgggccctac tttttgggca cccacgacaa gcgcttcccg ggctttctcg ccggcgacaa  20700
gctggcctgc gccatcgtca acacggccgg ccgcgagacc ggaggcgtgc actggctcgc  20760
cttcggctgg aacccgcgct cgcgcacctg ctacatgttc gacccctttg ggttctcgga  20820
ccgccggctc aagcagattt acagcttcga gtacgaggcc atgctgcgcc gcagcgccct  20880
ggcctcctcg cccgaccgct gtctcagcct cgagcagtcc actcagaccg tgcaggggcc  20940
cgactccgcc gcctgcggac tcttctgttg catgttcttg catgccttcg tgcactggcc  21000
cgaccgaccc atggacggaa accccaccat gaacttgctg acgggggtgc ccaacggcat  21060
gctacaatcg ccacaggtgc tgcccaccct caggcgcaac caggaggaac tctaccgctt  21120
cctcgcgcgc cactcccctt actttcgctc ccaccgcgcc gccatcgaac acgccaccgc  21180
ttttgacaaa atgaaacaac tgcgtgtatc tcaataaaca gcacttttat tttacatgca  21240
ctggagtata tgcaagttat ttaaaagtcg aaggggttct cgcgctcgtc gttgtgcgcc  21300
gcgctgggga gggccacgtt gcggtactgg tacttgggct gccacttgaa ctcggggatc  21360
accagtttgg gcactggggt ctcggggaag gtctcgctcc acatgcgccg gctcatctgc  21420
agggcgccca gcatgtccgg ggcggagatc ttgaaatcgc agttggggcc ggtgctctgc  21480
gcgcgcgagt tgcggtacac ggggttgcag cactggaaca ccatcagact ggggtacttc  21540
acactagcca gcacgctctt gtcgctgatc tgatccttgt ccagatcctc ggcgttgctc  21600
aggccgaacg gggtcatctt gcacagctgg cgtcccagga agggcacgct ctgaggcttg  21660
tggttacact cgcagtgcac gggcatcagc atcatccccg cgccgcgctg catattcggg  21720
tagagggcct tgacaaaggc cgcgatctgc ttgaaagctt gctgggcctt ggccccctcg  21780
ctgaaaaaca ggccgcagct cttcccgctg aactggttat tcccacaccc ggcatcctgc  21840
acgcagcagc gcgcgtcatg gctggtcagt tgcaccacgc tccgtcccca gcggttctgg  21900
gtcaccttag ccttgctggg ctgctccttc aacgcgcgct gcccgttctc gctggtcaca  21960
```

```
tccatctcca ccacgtggtc cttgtggatc atcatcgtcc cgtgcagaca cttgagctgg  22020
ccttccacct cggtgcagcc gtgatcccac agggcgcaac cggtgcactc ccagttcttg  22080
tgcgcaatcc cgctgtggct gaagatgtaa ccttgcaaca tgcggcccat gatggtgcta  22140
aatgctttct gggtggtgaa ggtcagttgc atcccgcggg cctcctcgtt catccaggtc  22200
tggcacatct tctggaagat ctcggtctgc tcgggcatga gcttgtaagc atcgcgcagg  22260
ccgctgtcga cgcggtagcg ttccatcagc acgttcatgg tatccatgcc cttctcccag  22320
gacgagacca gaggcagact cagagggttg cgtacgttca ggacaccggg ggtcgcgggc  22380
tcgacgatgc gttttccgtc cttgccttcc ttcaatagaa ccggcggctg gctgaatccc  22440
actcccacga tcacggcatc ttcctggggc atctcttcgt cggggtctac cttggtcaca  22500
tgcttggtct ttctggcttg cttctttttt ggagggctgt ccacggggag cacgtcctcc  22560
tcggaagacc cggagcccac ccgctgatac tttcggcgct tggtgggcag aggaggtggc  22620
ggcgaggggc tcctctcctg ctccggcgga tagcgcgccg acccgtggcc ccggggcgga  22680
gtggcctctc ggcccatgaa ccggcgcacg tcctgactgc cgccggccat tgtttcctag  22740
gggaagatgg aggagcagcc gcgtaagcag gagcaggagg aggacttaac cacccacgag  22800
caacccaaaa tcgagcagga cctgggcttc gaagagccgg ctcgtctaga acccccacag  22860
gatgaacagg agcacgagca agacgcaggc caggaggaga ccgacgctgg gctcgagcat  22920
ggctacctgg gaggagagga ggatgtgctg ctgaaacacc tgcagcgcca gtccctcatc  22980
ctccgggacg ccctggccga ccggagcgaa acccccctca gcgtcgagga gctgtgtcgg  23040
gcctacgagc tcaacctctt ctcgccgcgc gtaccccccca aacgccagcc caacggcacc  23100
tgcgagccca acccgcgtct caacttctat cccgtctttg cggtccccga agccctcgcc  23160
acctatcaca tctttttcaa gaaccaaaag atccccgtct cctgccgcgc caaccgcacc  23220
agcgccgacg cgctcctcgc tttggggccc ggcgcgcgca tacctgatat cgcttccctg  23280
gaagaggtgc ccaagatctt cgaagggctc ggtcgggacg agacgcgcgc ggcgaacgct  23340
ctgaaagaaa cagcagagga agagggtcac actagcgccc tggtagagtt ggaaggcgac  23400
aacgccaggc tggccgtgct caagcgcagc gtcgagctta cccacttcgc ctaccccgcc  23460
gtcaacctcc cgcccaaggt catgcgtcgc atcatggatc agctcatcat gccccacatc  23520
gaggccctcg atgaaagtca ggagcagcgc cccgaggacg cccggcccgt ggtcagcgac  23580
gagatgctcg cgcgctggct cgggacccgc gacccccagg ctttggaaca gcggcgcaaa  23640
ctcatgctgg ccgtggtcct ggtcaccctt gagctcgaat gcatgcgccg ctttttcagc  23700
gaccccgaga ccctgcgcaa ggtcgaggag accctgcact acactttcag gcacggtttc  23760
gtcaggcagg cctgcaagat ctccaacgtg gagctgacca acctggtctc ctgcctgggg  23820
atcctgcacg agaaccgcct gggccagacc gtgctccact ctaccctgaa gggcgaggcg  23880
cggcgggact atgtccgcga ctgcgtcttt ctctttctct gccacacatg gcaagcggcc  23940
atgggcgtgt ggcagcagtg tctcgaggac gagaacctaa aggagctgga caagcttctt  24000
gctagaaacc ttaaaaagct gtggacgggc ttcgacgagc gcaccgtcgc ctcggacctg  24060
gccgagatcg tcttccccga gcgcctgaga cagacgctga aaggcgggct gcccgacttc  24120
atgagccaga gcatgttgca aaactaccgc actttcattc ttgagcgatc aggcatcctg  24180
cccgccacct gcaacgcctt cccctccgac tttgtaccgc tgagctaccg cgagtgtccc  24240
ccgccgctgt ggagccactg ctacctcttg cagctggcca actacatcgc ctaccactcg  24300
gacgtgatcg aggacgtgag cggcgagggg ctgctcgagt gccactgtcg ctgcaacctg  24360
```

```
tgctccccgc atcgctccct ggtctgcaac ccccagctcc tgagcgagac ccaggtcatc  24420
ggtaccttcg agctgcaagg tccgcaggag tccaccgctc cgctgaaact cacgccgggg  24480
ttgtggactt ccgcgtacct gcgcaaattt gtacccgaag actaccacgc ccatgagata  24540
aagttctttg aggaccaatc gcgtccgcag cacgcggatc tcacggcctg cgtcatcacc  24600
cagggcgcga tcctcgccca attgcacgcc atccaaaaat cccgccaaga gtttcttctg  24660
aaaaagggta gaggggtcta cctggacccc cagacgggcg aggtgctcaa cccgggtctc  24720
ccccagcatg ccgaggaaga agcaggagcc gctagtggag gagatggaag aagaatggga  24780
cagccaggca gaggaggacg aatgggagga ggagacagag gaggaagaat tggaagaggt  24840
ggaagaggag caggcaacag agcagcccgt cgccgcacca tccgcgccgg cagccccgcc  24900
ggtcacggat acaacctccg ctccggtcaa gcctcctcgt agatgggatc aagtgaaggg  24960
tgacggtaag cacgagcggc agggctaccg atcatggagg gcccacaaag ccgcgatcat  25020
cgcctgcttg caagactgcg gggggaacat cgctttcgcc cgccgctacc tgctcttcca  25080
ccgcggggtg aacatccccc gcaacgtgtt gcattactac cgtcaccttc acagctaaga  25140
aaaagcaagt caaaggagtc gccggaggag gaggaggagg cctgaggatc gcggcgaacg  25200
agcccttgac caccagggag ctgaggaacc ggatcttccc cactctttat gccatttttc  25260
agcagagtcg aggtcagcag caagagctca aagtaaaaaa ccggtctctg cgctcgctca  25320
cccgcagttg cttgtaccac aaaaacgaag atcagctgca gcgcactctc gaagacgccg  25380
aggctctgtt ccacaagtac tgcgcgctca ctcttaaaga ctaaggcgcg cccacccgga  25440
aaaaaggcgg gaattacctc atcgccacca tgagcaagga gattcccacc ccttacatgt  25500
ggagctatca gccccaaatg ggcctggccg cgggcgcctc ccaggactac tccacccgca  25560
tgaactggct cagtgccggc ccctcgatga tctcacgggt caacggggtc cgcagtcatc  25620
gaaaccagat attgttggag caggcggcgg tcacctccac gcccagggca aagctcaacc  25680
cgcgtaattg gccctccacc ctggtgtatc aggaaatccc cgggccgact accgtactac  25740
ttccgcgtga cgcactggcc gaagtccgca tgactaactc aggtgtccag ctggccggcg  25800
gcgcttcccg gtgcccgctc cgcccacaat cgggtataaa aaccctggtg atccgaggca  25860
gaggcacaca gctcaacgac gagttggtga gctcttcgat cggtctgcga ccggacggag  25920
tgttccaact agccggagcc gggagatcct ccttcactcc caaccaggcc tacctgacct  25980
tgcagagcag ctcttcggag cctcgctccg gaggcatcgg aaccctccag tttgtggagg  26040
agtttgtgcc ctcggtctac ttcaacccct tctcgggatc gccaggcctc tacccggacg  26100
agttcatacc gaacttcgac gcagtgagag aagcggtgga cggctacgac tgaatgtccc  26160
atggtgactc ggctgagctc gctcggttga ggcatctgga ccactgccgc cgcctgcgct  26220
gcttcgcccg ggagagctgc ggactcatct actttgagtt tcccgaggag caccccaacg  26280
gccctgcaca cggagtgcgg atcaccgtag agggcaccac cgagtctcac ctggtcaggt  26340
tcttcaccca gcaacccttc ctggtcgagc gggaccgggg cgccaccacc tacaccgtct  26400
actgcatctg tccaaccccg aagttgcatg agaatttttg ttgtactctt tgtggtgagt  26460
ttaataaaag ctaaactctt gcaatactct ggaccttgtc gtcgtcaact caacgagacc  26520
gtctacctca ccaaccagac tgaggtaaaa ctcacctgca gaccacacaa gacctatatc  26580
atctggttct tcgagaacac ctcatttgca gtctccaaca ctcactgcac tagtccatga  26640
actgatgttg attaaaagcc caaaaaccaa tcagcccctt cccccatttc cccatccccc  26700
```

-continued

```
aattactcat aaaaaataaa tcattggaat taatcattca ataaagatca cttacttgaa  26760
atctgaaagt atgtctctgg tgtagttgtt cagcagcacc tcggtaccct cctcccagct  26820
ctggtactcc agtccccggc gggcggcgaa cttcctccac accttgaaag ggatgtcaaa  26880
ttcctggtcc acaattttca ttgtcttccc tctcagatgg caaagaggct ccgggtggaa  26940
gatgacttca accccgtcta cccctatggc tacgcgcgga atcagaatat ccccttcctc  27000
actccccccct ttgtctcctc cgatggattc aaaaacttcc cccctggggt cctgtcactt  27060
aaactggctg atccaatcac catcaacaat ggggatgtct cacttaaggt gggaggggga  27120
cttgctgtag agcaacagac tggtaaccta agcgtaaacc ctgatgcacc cttgcaagtt  27180
gcaagtgata agctacagct tgctctggct cctccattcg aggtcagaga tggaaagctt  27240
gctttaaagg caggtaatgg attaaaagta ctagataatt ccattactgg attgactgga  27300
ttattgaata cacttgtggt attaactgga aggggaatag gaacggagga attaaaaaat  27360
gacgatggtg taacaaacaa aggagtcggc ttgcgtgtaa gacttggaga tgacggcggg  27420
ctgacatttg ataaaaaggg tgatttagta gcctggaata aaaaagatga caggcgcacc  27480
ctgtggacaa cccctgacac atctccaaat tgcaaaatga gtacagaaaa ggattctaaa  27540
cttacgttga cacttacaaa gtgtggaagt caggttctgg gaaatgtatc tttacttgca  27600
gttacaggtg aatatcatca aatgactgct actacaaaga aggatgtaaa aatatcttta  27660
ctatttgatg agaatggaat tctattacca tcttcgtccc ttagcaaaga ttattggaat  27720
tacagaagtg atgattctat tgtatctcaa aaatataata atgcagttcc attcatgcca  27780
aacctgacag cttatccaaa accaagcgct caaaatgcaa aaaactattc aagaactaaa  27840
atcataagta atgtctactt aggtgctctt acctaccaac ctgtaattat cactattgca  27900
tttaatcagg aaactgaaaa tggatgtgct tattctataa catttacctt cacttggcaa  27960
aaagactatt ctgcccaaca gtttgatgtt acatctttta ccttctcata tcttacccaa  28020
gagaacaaag acaaagacta ataaaatgtt ttgaactgaa tttatgaatc tttatttatt  28080
tttacaccag cacgggtagt cagtttccca ccaccagccc atttcacagt gtaaacagtc  28140
ctttctcccc ggctggcctt aaaaagcatc atatcatggg taacagacat attcttaggt  28200
gttatattcc acacggtttc ctgtcgagcc aaacgctcat cagtgatatt aataaactcc  28260
ccgggcagct cacttaagtt catgtcgctg tccagctgct gagccacagg ctgctgtcca  28320
acttgcggtt gcttaacggg cggcgaagga gaagtccacg cctacatggg ggtagagtca  28380
taatcgtgca tcaggatagg gcggtggtgc tgcagcagcg cgcgaataaa ctgctgccgc  28440
cgccgctccg tcctgcagga atacaacatg gcagtggtct cctcagcgat gattcgcacc  28500
gcccgcagca taaggcgcct tgtcctccgg gcacagcagc gcaccctgat ctcacttaaa  28560
tcagcacagt aactgcagca cagcaccaca atattgttca aaatcccaca gtgcaaggcg  28620
ctgtatccaa agctcatggc ggggaccaca gaacccacgt ggccatcata ccacaagcgc  28680
aggtagatta agtggcgacc cctcataaac acgctggaca taaacattac ctcttttggc  28740
atgttgtaat tcaccacctc ccggtaccat ataaacctct gattaaacat ggcgccatcc  28800
accaccatcc taaaccagct ggccaaaacc tgcccgccgg ctatacactg cagggaaccg  28860
ggactggaac aatgacagtg gagagcccag gactcgtaac catggatcat catgctcgtc  28920
atgatatcaa tgttggcaca acacaggcac acgtgcatac acttcctcag gattacaagc  28980
tcctcccgcg ttagaaccat atcccaggga acaacccatt cctgaatcag cgtaaatccc  29040
acactgcagg gaagacctcg cacgtaactc acgttgtgca ttgtcaaagt gttacattcg  29100
```

-continued

```
ggcagcagcg gatgatcctc cagtatggta gcgcgggttt ctgtctcaaa aggaggtaga  29160
cgatccctac tgtacggagt gcgccgagac aaccgagatc gtgttggtcg tagtgtcatg  29220
ccaaatggaa cgccggacgt agtcattgaa atggattctc ttgcgtacct tgtcgtactt  29280
ctgccagcag aaagtggctc gggaacagca gataccttc ctcctgctgt ccttccgctg  29340
ctgacgctca gtcatccaac tgaagtacag ccattcccgc aggttctcca gcagctcctg  29400
tgcatctgat gaaacaaaag tcccgtcgat gcggattccc cttaaaacat cagccaggac  29460
attgtaggcc atcccaatcc agttaatgca tcctgatcta tcatgaagag gaggtggggg  29520
aagaactgga agaaccattt ttattccaag cggtctcgaa ggacgataaa gtgcaagtca  29580
cgcaggtgac agcgttcccc gccgctgtgc tggtggaaac agacagccag gtcaaaaccc  29640
actctatttt caaggtgctc gactgtggct tcgagcagtg gctctacgcg tacatccagc  29700
ataagaatca cattaaaggc tggacctcca tcgatttcat caatcatcag gttacactca  29760
ttcaccatcc ccaggtaatt ctcatttttc cagccttgga ttatttctac aaattgttgg  29820
tgtaagtcca ctccgcacat gtggaaaagt tcccacagcg ccccctccac tttcataatc  29880
aggcagacct tcatattaga aacagatcct gctgctccac cacctgcagc gtgttcaaaa  29940
caacaagatt caatgaggtt ctgccctctg ccctcagctc acgtctcagc gtcagctgca  30000
aaaagtcact caagtcctca gccactacag ctgacaattc agagccaggg ctaagcgtgg  30060
gactggcaag cgtgagtgag tactttaatg ctccaaagct agcacccaaa aactgcatgc  30120
tggaataagc tctctttgtg tcaccggtga tgccttccaa taggtgagtg ataaagcgag  30180
gtagtttttc tttaatcatt tgagtaatag aaaagtcctc taaataagtc actaggaccc  30240
caggaaccac aatgtggtag ctgacagcgt gtcgctcaag catggttagt agagatgaga  30300
gtctgaaaaa cagaaagcat gcactaaacc agagttgcca gtctcactga aggaaaaatc  30360
actctctcca gcagcaaagt gcccactggg tggccctctc ggacatacaa aaatcgatcc  30420
gtgtggttaa agagcagcac agttagctcc tgtcttctcc cagcaaagat cacatcggac  30480
tgggttagta tgcccctgga atggtagtca ttcaaggcca taaatctgcc ttggtagcca  30540
ttaggaatca gcacgctcac tctcaagtga accaaaacca ccccatgcgg aggaatgtgg  30600
aaagattctg ggcaaaaaaa ggtatatcta ttgctagtcc cttcctggac gggagcaatc  30660
cctccagggc tatctatgaa agcatacaga gattcagcca tagctcagcc cgcttaccag  30720
tagacagaga gcacagcagt acaagcgcca acagcagcga ctgactaccc actgacccag  30780
ctccctattt aaaggcacct tacactgacg taatgaccaa aggtctaaaa accccgccaa  30840
aaaaacacac acgccctggg tgtttttcgc gaaaacactt ccgcgttctc acttcctcgt  30900
atcgatttcg tgactcaact tccgggttcc cacgttacgt cacttctgcc cttacatgta  30960
actcagccgt agggcgccat cttgcccacg tccaaaatgg cttccatgtc cggccacgcc  31020
tccgcggcga ccgttagccg tgcgtcgtga cgtcatttgc atcaccgttt ctcgtccaat  31080
cagcgttggc tccgccccaa aaccgttaaa attcaaaagc tcatttgcat attaactttt  31140
gtttactttg tggggtatat tattgatgat g                                 31171
```

<210> SEQ ID NO 16
<211> LENGTH: 7973
<212> TYPE: DNA
<213> ORGANISM: Artificial Sequence
<220> FEATURE:
<223> OTHER INFORMATION: pAdApt26.CMVTO2A1.prM-Env vector

<400> SEQUENCE: 16

```
catcatcaat aatatacccc acaaagtaaa caaaagttaa tatgcaaatg agcttttgaa     60
ttttaacggt tttggggcgg agccaacgct gattggacga gaaacggtga tgcaaatgac    120
gtcacgacgc acggctaacg gtcgccgcgg aggcgtggcc tagcccggaa gcaagtcgcg    180
gggctgatga cgtataaaaa agcggacttt agacccggaa acggccgatt ttcccgcggc    240
cacgcccgga tatgaggtaa ttctgggcgg atgcaagtga aattaggtca ttttggcgcg    300
aaaactgaat gaggaagtga aaagcgaaaa ataccggtcc ctcccagggc ggaatattta    360
ccgagggccg agagactttg accgattacg tgggggtttc gattgcggtg tttttttcgc    420
gaatttccgc gtccgtgtca aagtccggtg tttatgtcac agatcagctg acctaggtgg    480
tcaatattgg ccattagcca tattattcat tggttatata gcataaatca atattggcta    540
ttggccattg catacgttgt atccatatca taatatgtac atttatattg gctcatgtcc    600
aacattaccg ccatgttgac attgattatt gactagttat taatagtaat caattacggg    660
gtcattagtt catagcccat atatggagtt ccgcgttaca taacttacgg taaatggccc    720
gcctggctga ccgcccaacg acccccgccc attgacgtca ataatgacgt atgttcccat    780
agtaacgcca atagggactt tccattgacg tcaatgggtg gagtatttac ggtaaactgc    840
ccacttggca gtacatcaag tgtatcatat gccaagtacg ccccctattg acgtcaatga    900
cggtaaatgg cccgcctggc attatgccca gtacatgacc ttatgggact ttcctacttg    960
gcagtacatc tacgtattag tcatcgctat taccatggtg atgcggtttt ggcagtacat   1020
caatgggcgt ggatagcggt ttgactcacg gggatttcca agtctccacc ccattgacgt   1080
caatgggagt ttgttttggc accaaaatca acgggacttt ccaaaatgtc gtaacaactc   1140
cgccccattg acgcaaatgg gcggtaggcg tgtacggtgg gaggtctata taagcagagc   1200
tcgtttagtt ccctatcagt gatagagaag acgccatcca cgctgttttg acctccatag   1260
aagacaccgg gaccgatcca gcctccgcgg ccgggaacgg tgcattggaa gcttggtacc   1320
gccaccatgg gcaaaagatc cgccggcagc atcatgtggc tggccagtct ggctgtcgtg   1380
atcgcctgtg ctggcgccgc tgtgacactg cctagccaca gcacccggaa gctgcagacc   1440
agaagccaga cctggctgga aagcagagag tacaccaagc acctgatccg ggtggaaaac   1500
tggatcttcc ggaaccccgg cttcgccctg gccgctgctg ctattgcttg gctgctgggc   1560
agcagcacca gccagaaagt gatctacctc gtgatgatcc tgctgatcgc ccctgcctac   1620
agcatccggt gtatcggcgt gtccaaccgg gacttcgtgg aaggcatgag cggcggcaca   1680
tgggtggacg tggtgctgga acatggcggc tgcgtgacag tgatggccca ggacaagccc   1740
accgtggaca tcgagctcgt gaccaccacc gtgtccaata tggccgaagt gcggagctac   1800
tgctacgagg ccagcatcag cgacatggcc agcgacagca gatgccctac acagggcgag   1860
gcctacctgg acaagcagtc cgacacccag tacgtgtgca agcggaccct ggtggataga   1920
ggctggggca atggctgcgg cctgtttggc aagggcagcc tcgtgacctg cgccaagttc   1980
gcctgcagca agaagatgac cggcaagagc atccagcccg agaacctgga ataccggatc   2040
atgctgagcg tgcacggcag ccagcactcc ggcatgatcg tgaacgacac cggccacgag   2100
acagacgaga accgggccaa ggtggaaatc acccccaaca gccctagagc cgaggccaca   2160
ctgggcggct ttggatctct gggcctggac tgcgagccta gaaccggcct ggatttcagc   2220
gacctgtact acctgaccat gaacaacaaa cactggctgg tgcacaaaga gtggttccac   2280
gacatccccc tgccctggca tgccggcgct gatacaggca caccccactg gaacaacaaa   2340
```

-continued gaggccctgg tggagttcaa ggacgcccac gccaagaggc agaccgtggt ggtgctggga 2400
tctcaggaag gcgccgtgca tacagctctg gctggcgccc tggaagccga aatggatggc 2460
gctaagggca gactgtccag cggccacctg aagtgccggc tgaagatgga caagctgcgg 2520
ctgaagggcg tgtcctacag cctgtgtacc gccgccttca ccttcaccaa gatccccgcc 2580
gagacactgc acggcaccgt gactgtggaa gtgcagtacg ccggcaccga cggcccttgt 2640
aaagtgcctg ctcagatggc cgtggatatg cagaccctga cccctgtggg caggctgatc 2700
accgccaacc ctgtgatcac cgagagcacc gagaacagca agatgatgct ggaactggac 2760
ccacccttcg gcgacagcta catcgtgatc ggcgtgggag agaagaagat cacccaccac 2820
tggcacagaa gcggcagcac catcggcaag gcctttgagg ctacagtgcg gggagccaag 2880
agaatggccg tgctgggaga taccgcctgg gactttggct ctgtgggcgg agccctgaac 2940
tctctgggca agggaatcca ccagatcttc ggcgctgcct tcaagagcct gttcggcggc 3000
atgagctggt tcagccagat cctgatcggc accctgctga tgtggctggg cctgaacacc 3060
aagaacggct ccatcagcct gatgtgcctg gctctgggag gcgtgctgat cttcctgagc 3120
acagccgtgt ccgcctgagc tagcgttaac ggatcctcta gacgagatcc gaacttgttt 3180
attgcagctt ataatggtta caaataaagc aatagcatca caaatttcac aaataaagca 3240
ttttttcac tgcattctag ttgtggtttg tccaaactca tcaatgtatc ttatcatgtc 3300
tagatccagg taggtttgag tagtgggcgt ggctaaggtg actataaagg cgggtgtctt 3360
acgagggtct tttgcttttt ctgcagacat catgaacggg actggcgggg ccttcgaagg 3420
ggggcttttt agcccttatt tgacaacccg cctgccggga tgggccggag ttcgtcagaa 3480
tgtgatggga tcgacggtgg atgggcgccc agtgcttcca gcaaattcct cgaccatgac 3540
ctacgcgacc gtggggaact cgtcgctcga cagcaccgcc gcagccgcgg cagccgcagc 3600
cgccatgaca gcgacgagac tggcctcgag ctacatgccc agcagcggta gtagcccctc 3660
tgtgcccagt tccatcatcg ccgaggagaa actgctggcc ctgctggccg agctggaagc 3720
cctgagccgc cagctggccg ccctgaccca gcaggtgtcc gagctccgcg aacagcagca 3780
gcagcaaaat aaatgattca ataaacacag attctgattc aaacagcaaa gcatctttat 3840
tatttatttt ttcgcgcgcg gtaggccctg gtccacctct cccgatcatt gagagtgcgg 3900
tggatttttt ccaggacccg gtagaggtgg gattggatgt tgaggtacat gggcatgagc 3960
ccgtcccgtg ggtggaggta gcaccactgc atggcctcgt gctctggggt cgtgttgtag 4020
atgatccagt catagcaggg gcgctgggcg tggtgctgga tgatgtcctt gaggaggaga 4080
ctgatggcca cggggagccc cttggtgtag gtgttggcaa aacggttgag ctgggaggga 4140
tgcatgcggg gggagatgat gtgcagtttg gcctggatct tgaggttggc gatgttgcca 4200
cccagatccc gccgggggtt catgttgtgc aggaccacca gaacggtgta gcccgtgcac 4260
ttggggaact tgtcatgcaa cttggaaggg aatgcgtgga agaatttgga gacgcccttg 4320
tgcccgccca ggttttccat gcactcatcc atgatgatgg caatgggccc gtgggctgcg 4380
gctttggcaa agacgtttct ggggtcagag acatcgtaat tatgctcctg ggtgagatca 4440
tcataagaca ttttaatgaa tttggggcgg agggtgccag attgggggac gatggttccc 4500
tcgggccccg ggcgaagtt cccctcgcag atctgcatct cccaggcttt catctcggag 4560
ggggggatca tgtccacctg cggggcgatg aaaaaaacgg tttccggggc gggggtgatg 4620
agctgcgagg agagcaggtt tctcaacagc tgggacttgc cgcacccggt cgggccgtag 4680

-continued atgaccccga tgacgggttg caggtggtag ttcaaggaca tgcagctgcc gtcgtcccgg 4740
aggagggggg ccacctcgtt gagcttgtct ctgacttgga ggttttcccg gacgagctcg 4800
ccgaggaggc ggtccccgcc cagcgagaga agctcttgca gggaagcaaa gtttttcagg 4860
ggcttgagcc cgtcggccat gggcatcttg gcgagggtct gcgagaggag ctccaggcgg 4920
tcccagagct cggtgacgtg ctctacggca tctcgatcca gcagacttcc tcgtttcggg 4980
ggttgggacg actgcgactg tagggcacga gacgatgggc gtccagcgcg gccagcgtca 5040
tgtccttcca gggtctcagg gtccgcgtga gggtggtctc cgtcacggtg aaggggtggg 5100
ccgcgggctg ggcgcttgca agggtgcgct tgagactcat cctgctggtg ctgaaacggg 5160
cacggtcttc gccctgcgcg tcggcgagat agcagttgac catgagctcg tagttgaggg 5220
cctcggcggc gtggcccttg gcgcggagct tgcccttgga agagcgcccg caggcgggac 5280
agaggaggga ttgcagggcg tagagcttgg gcgcgagaaa gacggactcg ggggcgaagg 5340
cgtccgctcc gcagtgggcg cagacggtct cgcactcgac tagccaggtg agctcgggct 5400
gctcggggtc aaaaaccagt tttcccccgt tctttttgat gcgcttctta cctcgcgtct 5460
ccatgagtct gtgtccgcgc tcggtgacaa acaggctgtc tgtgtccccg tagacggact 5520
tgatgggcct gtcctgcagg ggcgtcccgc ggtcctcctc gtagagaaac tcagaccact 5580
ctgagacgaa ggcgcgcgtc cacgccaaga caaaggaggc cacgtgcgag ggtagcggt 5640 cgttgtccac caggggggtcc acctttttcca cggtatgcag gcacatgtcc ccctcctccg 5700
catccaagaa ggtgattggc ttgtaggtgt aggccacgtg acctggggtt cccgacgggg 5760
gggtataaaa gggggcgggt ctgtgctcgt cctcactctc ttccgcgtcg ctgtccacga 5820
gcgccagctg ttggggtagg tattccctct caagattaat taattcgaac ccataatacc 5880
cataatagct gtttgccatc gacgcgaggc tggatggcct tccccattat gattcttctc 5940
gcttccggcg gcatcgggat gcccgcgttg caggccatgc tgtccaggca ggtagatgac 6000
gaccatcagg gacagcttca aggatcgctc gcggctctta ccagcccagc aaaaggccag 6060
gaaccgtaaa aaggccgcgt tgctggcgtt tttccatagg ctccgccccc ctgacgagca 6120
tcacaaaaat cgacgctcaa gtcagaggtg gcgaaacccg acaggactat aaagatacca 6180
ggcgtttccc cctggaagct ccctcgtgcg ctctcctgtt ccgaccctgc cgcttaccgg 6240
atacctgtcc gcctttctcc cttcgggaag cgtggcgctt tctcatagct cacgctgtag 6300
gtatctcagt tcggtgtagg tcgttcgctc caagctgggc tgtgtgcacg aaccccccgt 6360
tcagcccgac cgctgcgcct tatccggtaa ctatcgtctt gagtccaacc cggtaagaca 6420
cgacttatcg ccactggcag cagccactgg taacaggatt agcagagcga ggtatgtagg 6480
cggtgctaca gagttcttga agtggtggcc taactacggc tacactagaa ggacagtatt 6540
tggtatctgc gctctgctga agccagttac cttcggaaaa agagttggta gctcttgatc 6600
cggcaaacaa accaccgctg gtagcggtgg tttttttgtt tgcaagcagc agattacgcg 6660
cagaaaaaaa ggatctcaag aagatccttt gatcttttct acggggtctg acgctcagtg 6720
gaacgaaaac tcacgttaag ggattttggt catgagatta tcaaaaagga tcttcaccta 6780
gatcctttta aattaaaaat gaagttttaa atcaatctaa agtatatatg agtaaacttg 6840
gtctgacagt taccaatgct taatcagtga ggcacctatc tcagcgatct gtctatttcg 6900
ttcatccata gttgcctgac tccccgtcgt gtagataact acgatacggg agggcttacc 6960
atctggcccc agtgctgcaa tgataccgcg agacccacgc tcaccggctc cagatttatc 7020
agcaataaac cagccagccg gaagggccga gcgcagaagt ggtcctgcaa ctttatccgc 7080
ctccatccag tctattaatt gttgccggga agctagagta agtagttcgc cagttaatag 7140
tttgcgcaac gttgttgcca ttgctgcagg catcgtggtg tcacgctcgt cgtttggtat 7200
ggcttcattc agctccggtt cccaacgatc aaggcgagtt acatgatccc ccatgttgtg 7260
caaaaaagcg gttagctcct tcggtcctcc gatcgttgtc agaagtaagt tggccgcagt 7320
gttatcactc atggttatgg cagcactgca taattctctt actgtcatgc catccgtaag 7380
atgcttttct gtgactggtg agtactcaac caagtcattc tgagaatagt gtatgcggcg 7440
accgagttgc tcttgcccgg cgtcaacacg ggataatacc gcgccacata gcagaacttt 7500
aaaagtgctc atcattggaa aacgttcttc ggggcgaaaa ctctcaagga tcttaccgct 7560
gttgagatcc agttcgatgt aacccactcg tgcacccaac tgatcttcag catcttttac 7620
tttcaccagc gtttctgggt gagcaaaaac aggaaggcaa aatgccgcaa aaaagggaat 7680
aagggcgaca cggaaatgtt gaatactcat actcttcctt tttcaatatt attgaagcat 7740
ttatcagggt tattgtctca tgagcggata catatttgaa tgtatttaga aaaataaaca 7800
aataggggtt ccgcgcacat ttccccgaaa agtgccacct gacgtctaag aaaccattat 7860
tatcatgaca ttaacctata aaaataggcg tatcacgagg ccctttcgtc ttcaagaatt 7920
ggtcgatggc aaacagctat tatgggtatt atgggttcga attaattaat cga 7973

<210> SEQ ID NO 17
<211> LENGTH: 7973
<212> TYPE: DNA
<213> ORGANISM: Artificial Sequence
<220> FEATURE:
<223> OTHER INFORMATION: pAdApt26.ZIKV.001 vector

<400> SEQUENCE: 17
catcatcaat aatatacccc acaaagtaaa caaaagttaa tatgcaaatg agcttttgaa 60
ttttaacggt tttggggcgg agccaacgct gattggacga gaaacggtga tgcaaatgac 120
gtcacgacgc acggctaacg gtcgccgcgg aggcgtggcc tagcccggaa gcaagtcgcg 180
gggctgatga cgtataaaaa agcggacttt agacccggaa acggccgatt ttcccgcggc 240
cacgcccgga tatgaggtaa ttctgggcgg atgcaagtga aattaggtca ttttggcgcg 300
aaaactgaat gaggaagtga aaagcgaaaa ataccggtcc ctcccagggc ggaatattta 360
ccgagggccg agagactttg accgattacg tgggggtttc gattgcggtg tttttttcgc 420
gaatttccgc gtccgtgtca aagtccggtg tttatgtcac agatcagctg acctaggtgg 480
tcaatattgg ccattagcca tattattcat tggttatata gcataaatca atattggcta 540
ttggccattg catacgttgt atccatatca taatatgtac atttatattg gctcatgtcc 600
aacattaccg ccatgttgac attgattatt gactagttat taatagtaat caattacggg 660
gtcattagtt catagcccat atatggagtt ccgcgttaca taacttacgg taaatggccc 720
gcctggctga ccgcccaacg acccccgccc attgacgtca ataatgacgt atgttcccat 780
agtaacgcca atagggactt tccattgacg tcaatgggtg gagtatttac ggtaaactgc 840
ccacttggca gtacatcaag tgtatcatat gccaagtacg ccccctattg acgtcaatga 900
cggtaaatgg cccgcctggc attatgccca gtacatgacc ttatgggact ttcctacttg 960
gcagtacatc tacgtattag tcatcgctat taccatggtg atgcggtttt ggcagtacat 1020
caatgggcgt ggatagcggt ttgactcacg gggatttcca agtctccacc ccattgacgt 1080
caatgggagt ttgttttggc accaaaatca acgggacttt ccaaaatgtc gtaacaactc 1140

-continued

```
cgccccattg acgcaaatgg gcggtaggcg tgtacggtgg gaggtctata taagcagagc   1200
tcgtttagtg aaccgtcaga tcgcctggag acgccatcca cgctgttttg acctccatag   1260
aagacaccgg gaccgatcca gcctccgcgg ccgggaacgg tgcattggaa gcttggtacc   1320
gccaccatgg gcaaaagatc cgccggcagc atcatgtggc tggccagtct ggctgtcgtg   1380
atcgcctgtg ctggcgccgc tgtgacactg cctagccaca gcacccggaa gctgcagacc   1440
agaagccaga cctggctgga aagcagagag tacaccaagc acctgatccg ggtggaaaac   1500
tggatcttcc ggaaccccgg cttcgccctg gccgctgctg ctattgcttg gctgctgggc   1560
agcagcacca gccagaaagt gatctacctc gtgatgatcc tgctgatcgc ccctgcctac   1620
agcatccggt gtatcggcgt gtccaaccgg gacttcgtgg aaggcatgag cggcggcaca   1680
tgggtggacg tggtgctgga acatggcggc tgcgtgacag tgatggccca ggacaagccc   1740
accgtggaca tcgagctcgt gaccaccacc gtgtccaata tggccgaagt gcggagctac   1800
tgctacgagg ccagcatcag cgacatggcc agcgacagca gatgccctac acagggcgag   1860
gcctacctgg acaagcagtc cgacacccag tacgtgtgca agcggaccct ggtggataga   1920
ggctggggca atggctgcgg cctgtttggc aagggcagcc tcgtgacctg cgccaagttc   1980
gcctgcagca agaagatgac cggcaagagc atccagcccg agaacctgga ataccggatc   2040
atgctgagcg tgcacggcag ccagcactcc ggcatgatcg tgaacgacac cggccacgag   2100
acagacgaga accgggccaa ggtggaaatc accccccaaca gccctagagc cgaggccaca   2160
ctgggcggct ttggatctct gggcctggac tgcgagccta gaaccggcct ggatttcagc   2220
gacctgtact acctgaccat gaacaacaaa cactggctgg tgcacaaaga gtggttccac   2280
gacatccccc tgccctggca tgccggcgct gatacaggca caccccactg gaacaacaaa   2340
gaggccctgg tggagttcaa ggacgcccac gccaagaggc agaccgtggt ggtgctggga   2400
tctcaggaag gcgccgtgca tacagctctg gctggcgccc tggaagccga aatggatggc   2460
gctaagggca gactgtccag cggccacctg aagtgccggc tgaagatgga caagctgcgg   2520
ctgaagggcg tgtcctacag cctgtgtacc gccgccttca ccttcaccaa gatccccgcc   2580
gagacactgc acggcaccgt gactgtggaa gtgcagtacg ccggcaccga cggccccttgt   2640
aaagtgcctg ctcagatggc cgtggatatg cagaccctga cccctgtggg caggctgatc   2700
accgccaacc ctgtgatcac cgagagcacc gagaacagca agatgatgct ggaactggac   2760
ccacccttcg gcgacagcta catcgtgatc ggcgtgggag agaagaagat cacccaccac   2820
tggcacagaa gcggcagcac catcggcaag gcctttgagg ctacagtgcg gggagccaag   2880
agaatggccg tgctgggaga taccgcctgg gactttggct ctgtgggcgg agccctgaac   2940
tctctgggca agggaatcca ccagatcttc ggcgctgcct tcaagagcct gttcggcggc   3000
atgagctggt tcagccagat cctgatcggc accctgctga tgtggctggg cctgaacacc   3060
aagaacggct ccatcagcct gatgtgcctg gctctgggag gcgtgctgat cttcctgagc   3120
acagccgtgt ccgcctgagc tagcgttaac ggatcctcta gacgagatcc gaacttgttt   3180
attgcagctt ataatggtta caaataaagc aatagcatca caaatttcac aaataaagca   3240
tttttttcac tgcattctag ttgtggtttg tccaaactca tcaatgtatc ttatcatgtc   3300
tagatccagg taggtttgag tagtgggcgt ggctaaggtg actataaagg cgggtgtctt   3360
acgagggtct tttgcttttt ctgcagacat catgaacggg actggcgggg ccttcgaagg   3420
ggggcttttt agcccttatt tgacaacccg cctgccggga tgggccggag ttcgtcagaa   3480
tgtgatggga tcgacggtgg atgggcgccc agtgcttcca gcaaattcct cgaccatgac   3540
```

-continued

```
ctacgcgacc gtggggaact cgtcgctcga cagcaccgcc gcagccgcgg cagccgcagc   3600
cgccatgaca gcgacgagac tggcctcgag ctacatgccc agcagcggta gtagcccctc   3660
tgtgcccagt tccatcatcg ccgaggagaa actgctggcc ctgctggccg agctggaagc   3720
cctgagccgc cagctggccg ccctgaccca gcaggtgtcc gagctccgcg aacagcagca   3780
gcagcaaaat aaatgattca ataaacacag attctgattc aaacagcaaa gcatctttat   3840
tatttatttt ttcgcgcgcg gtaggccctg gtccacctct cccgatcatt gagagtgcgg   3900
tggatttttt ccaggacccg gtagaggtgg gattggatgt tgaggtacat gggcatgagc   3960
ccgtcccgtg ggtggaggta gcaccactgc atggcctcgt gctctggggt cgtgttgtag   4020
atgatccagt catagcaggg gcgctgggcg tggtgctgga tgatgtcctt gaggaggaga   4080
ctgatggcca cggggagccc cttggtgtag gtgttggcaa aacggttgag ctgggaggga   4140
tgcatgcggg gggagatgat gtgcagtttg gcctggatct tgaggttggc gatgttgcca   4200
cccagatccc gccgggggtt catgttgtgc aggaccacca gaacggtgta gcccgtgcac   4260
ttggggaact tgtcatgcaa cttggaaggg aatgcgtgga agaatttgga gacgcccttg   4320
tgcccgccca ggttttccat gcactcatcc atgatgatgg caatgggccc gtgggctgcg   4380
gctttggcaa agacgtttct ggggtcagag acatcgtaat tatgctcctg ggtgagatca   4440
tcataagaca ttttaatgaa tttggggcgg agggtgccag attgggggac gatggttccc   4500
tcgggccccg gggcgaagtt cccctcgcag atctgcatct cccaggcttt catctcggag   4560
ggggggatca tgtccacctg cggggcgatg aaaaaaacgg tttccggggc gggggtgatg   4620
agctgcgagg agagcaggtt tctcaacagc tgggacttgc cgcacccggt cgggccgtag   4680
atgaccccga tgacgggttg caggtggtag ttcaaggaca tgcagctgcc gtcgtcccgg   4740
aggagggggg ccacctcgtt gagcttgtct ctgacttgga ggttttcccg gacgagctcg   4800
ccgaggaggc ggtccccgcc cagcgagaga agctcttgca gggaagcaaa gtttttcagg   4860
ggcttgagcc cgtcggccat gggcatcttg gcgagggtct gcgagaggag ctccaggcgg   4920
tcccagagct cggtgacgtg ctctacggca tctcgatcca gcagacttcc tcgtttcggg   4980
ggttgggacg actgcgactg tagggcacga gacgatgggc gtccagcgcg gccagcgtca   5040
tgtccttcca gggtctcagg gtccgcgtga gggtggtctc cgtcacggtg aaggggtggg   5100
ccgcgggctg ggcgcttgca agggtgcgct tgagactcat cctgctggtg ctgaaacggg   5160
cacggtcttc gccctgcgcg tcggcgagat agcagttgac catgagctcg tagttgaggg   5220
cctcggcggc gtggcccttg gcgcggagct tgcccttgga agagcgcccg caggcgggac   5280
agaggaggga ttgcagggcg tagagcttgg gcgcgagaaa gacggactcg ggggcgaagg   5340
cgtccgctcc gcagtgggcg cagacggtct cgcactcgac tagccaggtg agctcgggct   5400
gctcggggtc aaaaaccagt ttcccccgt tctttttgat gcgcttctta cctcgcgtct   5460
ccatgagtct gtgtccgcgc tcggtgacaa acaggctgtc tgtgtccccg tagacggact   5520
tgatgggcct gtcctgcagg ggcgtcccgc ggtcctcctc gtagagaaac tcagaccact   5580
ctgagacgaa ggcgcgcgtc cacgccaaga caaaggaggc cacgtgcgag ggtagcggt   5640
cgttgtccac cagggggtcc accttttcca cggtatgcag gcacatgtcc ccctcctccg   5700
catccaagaa ggtgattggc ttgtaggtgt aggccacgtg acctggggtt cccgacgggg   5760
gggtataaaa gggggcgggt ctgtgctcgt cctcactctc ttccgcgtcg ctgtccacga   5820
gcgccagctg ttggggtagg tattccctct caagattaat taattcgaac ccataatacc   5880
```

```
cataatagct gtttgccatc gacgcgaggc tggatggcct tccccattat gattcttctc   5940

gcttccggcg gcatcgggat gcccgcgttg caggccatgc tgtccaggca ggtagatgac   6000

gaccatcagg gacagcttca aggatcgctc gcggctctta ccagcccagc aaaaggccag   6060

gaaccgtaaa aaggccgcgt tgctggcgtt tttccatagg ctccgccccc ctgacgagca   6120

tcacaaaaat cgacgctcaa gtcagaggtg gcgaaacccg acaggactat aaagatacca   6180

ggcgtttccc cctggaagct ccctcgtgcg ctctcctgtt ccgaccctgc cgcttaccgg   6240

atacctgtcc gcctttctcc cttcgggaag cgtggcgctt tctcatagct cacgctgtag   6300

gtatctcagt tcggtgtagg tcgttcgctc caagctgggc tgtgtgcacg aaccccccgt   6360

tcagcccgac cgctgcgcct tatccggtaa ctatcgtctt gagtccaacc cggtaagaca   6420

cgacttatcg ccactggcag cagccactgg taacaggatt agcagagcga ggtatgtagg   6480

cggtgctaca gagttcttga agtggtggcc taactacggc tacactagaa ggacagtatt   6540

tggtatctgc gctctgctga agccagttac cttcggaaaa agagttggta gctcttgatc   6600

cggcaaacaa accaccgctg gtagcggtgg tttttttgtt tgcaagcagc agattacgcg   6660

cagaaaaaaa ggatctcaag aagatccttt gatcttttct acggggtctg acgctcagtg   6720

gaacgaaaac tcacgttaag ggattttggt catgagatta tcaaaaagga tcttcaccta   6780

gatcctttta aattaaaaat gaagttttaa atcaatctaa agtatatatg agtaaacttg   6840

gtctgacagt taccaatgct taatcagtga ggcacctatc tcagcgatct gtctatttcg   6900

ttcatccata gttgcctgac tccccgtcgt gtagataact acgatacggg agggcttacc   6960

atctggcccc agtgctgcaa tgataccgcg agacccacgc tcaccggctc cagatttatc   7020

agcaataaac cagccagccg gaagggccga gcgcagaagt ggtcctgcaa ctttatccgc   7080

ctccatccag tctattaatt gttgccggga agctagagta agtagttcgc cagttaatag   7140

tttgcgcaac gttgttgcca ttgctgcagg catcgtggtg tcacgctcgt cgtttggtat   7200

ggcttcattc agctccggtt cccaacgatc aaggcgagtt acatgatccc ccatgttgtg   7260

caaaaaagcg gttagctcct tcggtcctcc gatcgttgtc agaagtaagt tggccgcagt   7320

gttatcactc atggttatgg cagcactgca taattctctt actgtcatgc catccgtaag   7380

atgcttttct gtgactggtg agtactcaac caagtcattc tgagaatagt gtatgcggcg   7440

accgagttgc tcttgcccgg cgtcaacacg ggataatacc gcgccacata gcagaacttt   7500

aaaagtgctc atcattggaa aacgttcttc ggggcgaaaa ctctcaagga tcttaccgct   7560

gttgagatcc agttcgatgt aacccactcg tgcacccaac tgatcttcag catcttttac   7620

tttcaccagc gtttctgggt gagcaaaaac aggaaggcaa aatgccgcaa aaaagggaat   7680

aagggcgaca cggaaatgtt gaatactcat actcttcctt tttcaatatt attgaagcat   7740

ttatcagggt tattgtctca tgagcggata catatttgaa tgtatttaga aaaataaaca   7800

aataggggtt ccgcgcacat ttccccgaaa agtgccacct gacgtctaag aaaccattat   7860

tatcatgaca ttaacctata aaaataggcg tatcacgagg ccctttcgtc ttcaagaatt   7920

ggtcgatggc aaacagctat tatgggtatt atgggttcga attaattaat cga          7973
```

<210> SEQ ID NO 18
<211> LENGTH: 6535
<212> TYPE: DNA
<213> ORGANISM: Artificial Sequence
<220> FEATURE:
<223> OTHER INFORMATION: pMK.RQ.CMVTO2A1_GL_AO_RFL vector

<400> SEQUENCE: 18

-continued

```
ctaaattgta agcgttaata ttttgttaaa attcgcgtta aatttttgtt aaatcagctc     60
atttttaac caataggccg aaatcggcaa aatcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattgaagg aaggccgtca    360
aggccgcata ccggtgaccc gcgtccgtgt caaagtccgg tgtttatgtc acagatcagc    420
tgagcgatct cgagtcaata ttggccatta gccatattat tcattggtta tatagcataa    480
atcaatattg gctattggcc attgcatacg ttgtatccat atcataatat gtacatttat    540
attggctcat gtccaacatt accgccatgt tgacattgat tattgactag ttattaatag    600
taatcaatta cggggtcatt agttcatagc ccatatatgg agttccgcgt tacataactt    660
acggtaaatg gcccgcctgg ctgaccgccc aacgaccccc gcccattgac gtcaataatg    720
acgtatgttc ccatagtaac gccaataggg actttccatt gacgtcaatg ggtggagtat    780
ttacggtaaa ctgcccactt ggcagtacat caagtgtatc atatgccaag tacgccccct    840
attgacgtca atgacggtaa atggcccgcc tggcattatg cccagtacat gaccttatgg    900
gactttccta cttggcagta catctacgta ttagtcatcg ctattaccat ggtgatgcgg    960
ttttggcagt acatcaatgg gcgtggatag cggtttgact cacggggatt tccaagtctc   1020
caccccattg acgtcaatgg gagtttgttt tggcaccaaa atcaacggga ctttccaaaa   1080
tgtcgtaaca actccgcccc attgacgcaa atgggcggta ggcgtgtacg gtgggaggtc   1140
tatataagca gagctcgttt agttccctat cagtgataga gaagacgcca tccacgctgt   1200
tttgacctcc atagaagaca ccgggaccga tccagcctcc gcggccggga acggtgcatt   1260
ggagcgatcg caagcttgcc accatgggcg tgaaggtgct gttcgccctg atctgtatcg   1320
ccgtggccga ggccaagccc accgagaaca acgaggactt caacatcgtg gccgtggcct   1380
ccaacttcgc caccaccgat ctggacgccg acagaggcaa gctgcccggc aagaaactgc   1440
ccctggaagt gctgaaagag atggaagcca acgcccggaa ggccggctgt accagaggct   1500
gtctgatctg cctgagccac attaagtgca cccccaagat gaagaagttc atccccggca   1560
gatgccacac ctacgagggc gacaaagagt ctgcccaggg cggaatcgga gaggccatcg   1620
tggacatccc tgagatcccc ggcttcaagg acctggaacc catggaacag tttatcgccc   1680
aggtggacct gtgcgtggac tgcacaacag gctgcctgaa gggcctggcc aacgtgcagt   1740
gtagcgacct gctgaagaag tggctgcccc agagatgcgc caccttcgcc tctaagatcc   1800
agggacaggt ggacaagatc aagggcgctg gcggcgactg agtctagagc gatcgcatcc   1860
gaacttgttt attgcagctt ataatggtta caaataaagc aatagcatca caaatttcac   1920
aaataaagca tttttttcac tgcattctag ttgtggtttg tccaaactca tcaatgtatc   1980
ttatcatgtc tgctagcatc gcaggtaggt ttgagtagtg ggcgtggcta aggtgactat   2040
aaaggcgggt gtcttacgag ggtctttttg cttttctgca gacatcagtc ccaatgcatt   2100
ggcacgtgac tcaacttccg ggttcccacg ttacgtcact tctgccctta catgttaatg   2160
gtaccataga gcccaccgca tccccagcat gcctgctatt gtcttcccaa tcctccccct   2220
tgctgtcctg ccccaccccc accccccagaa tagaatgaca cctactcaga caatgcgatg   2280
caatttcctc attttattag gaaaggacag tgggagtggc accttccagg gtcaaggaag   2340
```

-continued

```
gcacggggga ggggcaaaca acagatggct ggcaactaga aggcacagtt aattaaggaa   2400
ttcacatctt ggccacgggt ttcttcagga tctctctgat ggctctgcca tcgatcttgc   2460
cggtcaggcc ctttggcacc tcgtccacga atctgacgcc gcctctcagt ctcttggcgt   2520
tggacacctg agaggccacg tagtccatca cttctttctc ggtcatgttc ttgccgcttt   2580
ccagcaccac cacagcgcct ggcagttcgc cagccacagg atctggcacg cctgccacgc   2640
cagcgtcgaa gatgctggga tgctgcagca gcacagattc cagctcggca gggggcacct   2700
gatagccctt gtacttgatc agagacttca gccggtccac gatgaagaag tgcttttcct   2760
catcgtagta gccgatgtcg ccggtgtgca gccagccctc ttcgtcgatc agctctttgg   2820
tggcctcggg gttgttcacg tagcccttca tcagcatggg gcccttcacg cacacttcgc   2880
cccgtctgtt agggcccagg gacttcttgg tatccaggtc aatcactttg gccttgaaca   2940
ggggcaccac ctttccagag gcgccaggct tatcgtcgcc ctcgggggtg atgatgatgg   3000
cgctggttgt ttctgtcagg ccgtagccct gccgcacgcc aggcagattg aaccgtctgg   3060
ccacggcctc tcccacttct ttgctcagag gggcgcctcc gctggcgatt tccaccaggt   3120
tgctcaggtc gtatttgttc agcagttcgc tcttgttcag gatggcgaac agggtgggca   3180
ccaggatcac ataggtgcac ttgtagtcct gcagggtttt caggaaggtt tcctcgtcga   3240
acttggtcag catcacgacc cggaagccgc agatcaggta gcccagggtg gtgaacatgc   3300
cgaagccgtg gtgaaaaggc accacggtca gcacggcggt gccaggggac acctggtttc   3360
cgtagatggg gtcccgggcg tggctgaacc gtgtcacggt gttctcgtgg gtcagctgca   3420
cgcctttggg cagtccggtg ctgccgctgc tgttcatgat cagggccacc tgttctttcc   3480
ggtccacttc cacggtcttg aagctggagg cctggaagcc tggggggtg ttccgcttga   3540
tgaaggtgtc caggcactgg tagccccggt agtccacctt gctgtccagg atcacgatgg   3600
tcttgatggt ggtcacggtt ttctgcacgg tgatcacttt gtccaggcct ttcttgctgc   3660
tgaacacgat ggtgggcttg ctgatgccca ggctgtgcac cagttcccgc agggtgtaga   3720
tctcgttggt gggggccact cccactccga tgaacaggcc ggcgatcacg gggatgaaga   3780
actcttcgca gttctcgctg cacagggcga ttctgccgtc caccaccagg ccatagttct   3840
gcagggcctt gcccaggcag cagctctttt ccaggtactc ggcgtagctg tagtccacgc   3900
cggtcacggc attggtgaag gcgatagcgc ccagcttggc gtatctttcc atgtacttcc   3960
gcagctgggt gccggcagag ccttcctcga tggggtagaa gggcttgggg cccacgacga   4020
tgttctcgtc gttttccatg ttctccatgg tggcgcgcct taattaacca gtgaagggtc   4080
cccggctagg ctaggccgct cggtcccggt ggctggtccg gagaacgtgg gtccctcacg   4140
ctgtcttgaa ggcgaatggc ggtctgctaa ccgggctctg cttatatacc ctaggacagc   4200
ccatggtccg cccacgaacc gcccagtaac gcccataact ccgcccggga acgcccatgg   4260
tcactccccg ttacgcccct ttccactgac gtcaatggaa agtccccgcg gttttggtgc   4320
caagaacatt gactaatatg gaatttcccc acccaccatt gccggtaatg gtgggaaagg   4380
ggaactggcc ccgttcccat tgacgtcact ggctattggc caaggacatt gactaataat   4440
agaaatcccc ctttttggtg ccaaatgagg cggtgggctt atggaaagtc cccatttaac   4500
ccctattctg gtgccaggac ggatgtatat gcttgccaag tcattgattt ggatccatta   4560
actcagccgt agggcgccat cttgcccacg tccaaaatgg cttccatgtc cggccacgtg   4620
acgcgtctgg gcctcatggg ccttcctttc actgcccgct ttccagtcgg gaaacctgtc   4680
gtgccagctg cattaacatg gtcatagctg tttccttgcg tattgggcgc tctccgcttc   4740
```

```
ctcgctcact gactcgctgc gctcggtcgt tcgggtaaag cctggggtgc ctaatgagca   4800

aaaggccagc aaaaggccag gaaccgtaaa aaggccgcgt tgctggcgtt tttccatagg   4860

ctccgccccc ctgacgagca tcacaaaaat cgacgctcaa gtcagaggtg gcgaaacccg   4920

acaggactat aaagatacca ggcgtttccc cctggaagct ccctcgtgcg ctctcctgtt   4980

ccgaccctgc cgcttaccgg atacctgtcc gcctttctcc cttcgggaag cgtggcgctt   5040

tctcatagct cacgctgtag gtatctcagt tcggtgtagg tcgttcgctc caagctgggc   5100

tgtgtgcacg aaccccccgt tcagcccgac cgctgcgcct tatccggtaa ctatcgtctt   5160

gagtccaacc cggtaagaca cgacttatcg ccactggcag cagccactgg taacaggatt   5220

agcagagcga ggtatgtagg cggtgctaca gagttcttga agtggtggcc taactacggc   5280

tacactagaa gaacagtatt tggtatctgc gctctgctga agccagttac cttcggaaaa   5340

agagttggta gctcttgatc cggcaaacaa accaccgctg gtagcggtgg tttttttgtt   5400

tgcaagcagc agattacgcg cagaaaaaaa ggatctcaag aagatccttt gatcttttct   5460

acggggtctg acgctcagtg gaacgaaaac tcacgttaag ggattttggt catgagatta   5520

tcaaaaagga tcttcaccta gatcctttta aattaaaaat gaagttttaa atcaatctaa   5580

agtatatatg agtaaacttg gtctgacagt tattagaaaa attcatccag cagacgataa   5640

aacgcaatac gctggctatc cggtgccgca atgccataca gcaccagaaa acgatccgcc   5700

cattcgccgc ccagttcttc cgcaatatca cgggtggcca gcgcaatatc ctgataacga   5760

tccgccacgc ccagacggcc gcaatcaata aagccgctaa aacggccatt ttccaccata   5820

atgttcggca ggcacgcatc accatgggtc accaccagat cttcgccatc cggcatgctc   5880

gctttcagac gcgcaaacag ctctgccggt gccaggccct gatgttcttc atccagatca   5940

tcctgatcca ccaggcccgc ttccatacgg gtacgcgcac gttcaatacg atgtttcgcc   6000

tgatgatcaa acggacaggt cgccgggtcc agggtatgca gacgacgcat ggcatccgcc   6060

ataatgctca ctttttctgc cggcgccaga tggctagaca gcagatcctg acccggcact   6120

tcgcccagca gcagccaatc acggcccgct tcggtcacca catccagcac cgccgcacac   6180

ggaacaccgg tggtggccag ccagctcaga cgcgccgctt catcctgcag ctcgttcagc   6240

gcaccgctca gatcggtttt cacaaacagc accggacgac cctgcgcgct cagacgaaac   6300

accgccgcat cagagcagcc aatggtctgc tgcgcccaat catagccaaa cagacgttcc   6360

acccacgctg ccgggctacc cgcatgcagg ccatcctgtt caatcatact cttccttttt   6420

caatattatt gaagcattta tcagggttat tgtctcatga gcggatacat atttgaatgt   6480

atttagaaaa ataaacaaat aggggttccg cgcacatttc cccgaaaagt gccac        6535
```

<210> SEQ ID NO 19
<211> LENGTH: 35606
<212> TYPE: DNA
<213> ORGANISM: Artificial Sequence
<220> FEATURE:
<223> OTHER INFORMATION: pWe.Ad26.dE3.5orf6 cosmid

<400> SEQUENCE: 19

```
ttaattaatg ctggccctgc tggccgagct ggaagccctg agccgccagc tggccgccct     60

gacccagcag gtgtccgagc tccgcgaaca gcagcagcag caaaataaat gattcaataa    120

acacagattc tgattcaaac agcaaagcat ctttattatt tattttttcg cgcgcggtag    180

gccctggtcc acctctcccg atcattgaga gtgcggtgga ttttttccag gacccggtag    240
```

```
aggtgggatt ggatgttgag gtacatgggc atgagcccgt cccgtgggtg gaggtagcac    300
cactgcatgg cctcgtgctc tggggtcgtg ttgtagatga tccagtcata gcaggggcgc    360
tgggcgtggt gctggatgat gtccttgagg aggagactga tggccacggg gagccccttg    420
gtgtaggtgt tggcaaaacg gttgagctgg gagggatgca tgcgggggga gatgatgtgc    480
agtttggcct ggatcttgag gttggcgatg ttgccaccca gatcccgccg gggttcatg     540
ttgtgcagga ccaccagaac ggtgtagccc gtgcacttgg ggaacttgtc atgcaacttg    600
gaagggaatg cgtggaagaa tttggagacg cccttgtgcc cgcccaggtt ttccatgcac    660
tcatccatga tgatggcaat gggcccgtgg gctgcggctt tggcaaagac gtttctgggg    720
tcagagacat cgtaattatg ctcctgggtg agatcatcat aagacatttt aatgaatttg    780
gggcggaggg tgccagattg ggggacgatg gttccctcgg gccccggggc gaagttcccc    840
tcgcagatct gcatctccca ggctttcatc tcggaggggg ggatcatgtc cacctgcggg    900
gcgatgaaaa aaacggtttc cggggcgggg gtgatgagct gcgaggagag caggtttctc    960
aacagctggg acttgccgca cccggtcggg ccgtagatga ccccgatgac gggttgcagg   1020
tggtagttca aggacatgca gctgccgtcg tcccggagga ggggggccac ctcgttgagc   1080
ttgtctctga cttggaggtt ttcccggacg agctcgccga ggaggcggtc cccgcccagc   1140
gagagaagct cttgcaggga agcaaagttt ttcaggggct tgagcccgtc ggccatgggc   1200
atcttggcga gggtctgcga gaggagctcc aggcggtccc agagctcggt gacgtgctct   1260
acggcatctc gatccagcag acttcctcgt ttcgggggtt gggacgactg cgactgtagg   1320
gcacgagacg atgggcgtcc agcgcggcca gcgtcatgtc cttccagggt ctcagggtcc   1380
gcgtgagggt ggtctccgtc acggtgaagg ggtgggccgc gggctgggcg cttgcaaggg   1440
tgcgcttgag actcatcctg ctggtgctga aacgggcacg gtcttcgccc tgcgcgtcgg   1500
cgagatagca gttgaccatg agctcgtagt tgagggcctc ggcggcgtgg cccttggcgc   1560
ggagcttgcc cttggaagag cgcccgcagg cgggacagag gagggattgc agggcgtaga   1620
gcttgggcgc gagaaagacg gactcggggg cgaaggcgtc cgctccgcag tgggcgcaga   1680
cggtctcgca ctcgactagc caggtgagct cgggctgctc ggggtcaaaa accagttttc   1740
ccccgttctt tttgatgcgc ttcttacctc gcgtctccat gagtctgtgt ccgcgctcgg   1800
tgacaaacag gctgtctgtg tccccgtaga cggacttgat gggcctgtcc tgcaggggcg   1860
tcccgcggtc ctcctcgtag agaaactcag accactctga gacgaaggcg cgcgtccacg   1920
ccaagacaaa ggaggccacg tgcgaggggt agcggtcgtt gtccaccagg gggtccacct   1980
tttccacggt atgcaggcac atgtccccct cctccgcatc caagaaggtg attggcttgt   2040
aggtgtaggc cacgtgacct ggggttcccg acgggggggt ataaaagggg gcgggtctgt   2100
gctcgtcctc actctcttcc gcgtcgctgt ccacgagcgc cagctgttgg ggtaggtatt   2160
ccctctcaag agcgggcatg acctcggcac tcaggttgtc agtttctaga aacgaggagg   2220
atttgatgtg ggcctgccct gccgcgatgc tttttaggag actttcatcc atctggtcag   2280
aaaagactat ttttttattg tcaagcttgg tggcgaagga gccatagagg gcgtttgaga   2340
gaagcttggc gatggatctc atggtctgat tttgtcacgg tcggcgcgc tccttggccg    2400
cgatgttgag ctggacatat tcgcgcgcga cacacttcca ttcggggaag acggtggtgc   2460
gctcgtcggg cacgatcctg acgcgccagc cgcggttatg cagggtgacc aggtccacgc   2520
tggtggccac ctcgccgcgc aggggctcgt tggtccagca gagtctgccg cccttgcgcg   2580
agcagaacgg gggcagcaca tcaagcagat gctcgtcagg ggggtccgca tcgatggtga   2640
```

```
agatgcccgg acagagttcc ttgtcaaaat aatcgatttt tgaggatgca tcgtccaagg   2700
ccatctgcca ctcgcgggcg gccagcgctc gctcgtaggg gttgaggggc ggaccccaag   2760
gcatgggatg cgtgagggcg gaggcgtaca tgccgcagat gtcatagaca tagatgggct   2820
ccgagaggat gccgatgtag gtgggatagc agcgcccccc gcggatgctt gcgcgcacgt   2880
agtcatacaa ctcgtgcgag gggggccaaga aggcggggcc gagattggtg cgctggggct   2940
gctcggcgcg gaagacgatc tggcgaaaga tggcgtgcga gttggaggag atggtgggcc   3000
gttggaagat gttaaagtgg gcgtgaggca ggcggaccga gtcgcggatg aagtgcgcgt   3060
aggagtcttg cagcttggcg acgagctcgg cggtgacgag gacgtccatg gcgcagtagt   3120
ccagcgtttc gcggatgatg tcataactcg cctctccttt cttctcccac agctcgcggt   3180
tgagggcgta ttcctcgtca tccttccagt actcccggag cgggaatcct cgatcgtccg   3240
cacggtaaga gcccagcatg tagaaatggt tcacggcctt gtagggacag cagcccttct   3300
ccacggggag ggcgtaagct tgagcggcct tgcggagcga ggtgtgcgtc agggcaaagg   3360
tgtccctgac catgactttc aagaactggt acttgaagtc cgagtcgtcg cagccgccgt   3420
gctcccagag ctcgaaatcg gtgcgcttct tcgagagggg gttaggcaga gcgaaagtga   3480
cgtcattgaa gagaatcttg cctgcccgcg gcatgaaatt gcgggtgatg cggaaagggc   3540
ccgggacgga ggctcggttg ttgatgacct gggcggcgag gacgatctcg tcaaagccgt   3600
tgatgttgtg cccgacgatg tagagttcca tgaatcgcgg gcggcctttg atgtgcggca   3660
gctttttgag ctcctcgtag gtgaggtcct cggggcattg caggccgtgc tgctcgagcg   3720
cccactcctg gagatgtggg ttggcttgca tgaaggaagc ccagagctcg cgggccatga   3780
gggtctggag ctcgtcgcga aagaggcgga actgctggcc cacggccatc ttttctgggg   3840
tgacgcagta gaaggtgagg gggtcccgct cccagcgatc ccagcgtaaa cgcacggcga   3900
gatcgcgagc gagggcgacc agctctgggt ccccggagaa tttcatgacc agcatgaagg   3960
ggacgagctg cttgccgaag gaccccatcc aggtgtaggt ttctacatcg taggtgacaa   4020
agagccgctc cgtgcgagga tgagagccga ttgggaagaa ctggatttcc tgccaccagt   4080
tggacgagtg gctgttgatg tgatgaaagt agaaatcccg ccggcgaacc gagcactcgt   4140
gctgatgctt gtaaaagcgt ccgcagtact cgcagcgctg cacgggctgt acctcatcca   4200
cgagatacac agcgcgtccc ttgaggagga acttcaggag tggcggccct ggctggtggt   4260
tttcatgttc gcctgcgtgg gactcaccct ggggctcctc gaggacggag aggctgacga   4320
gcccgcgcgg gagccaggtc cagatctcgg cgcggcgggg gcggagagcg aagacgaggg   4380
cgcgcagttg ggagctgtcc atggtgtcgc ggagatccag gtccgggggc agggttctga   4440
ggttgacctc gtagaggcgg gtgagggcgt gcttgagatg cagatggtac ttgatttcta   4500
cgggtgagtt ggtggtcgtg tccacgcatt gcatgagccc gtagctgcgc ggggccacga   4560
ccgtgccgcg gtgcgctttt agaagcggtg tcgcggacgc gctcccggcg gcagcggcgg   4620
ttccggcccc gcgggcaggg gcggcagagg cacgtcggcg tggcgctcgg gcaggtcccg   4680
gtgctgcgcc ctgagagcgc tggcgtgcgc gacgacgcgg cggttgacat cctggatctg   4740
ccgcctctgc gtgaagacca cgggccccgt gactttgaac ctgaaagaca gttcaacaga   4800
atcaatctct gcgtcattga cggcggcctg acgcaggatc tcttgcacgt cgcccgagtt   4860
gtcctggtag gcgatctcgg acatgaactg ttcgatctcc tcctcctgga gatcgccgcg   4920
gcccgcgcgc tccacggtgg cggcgaggtc attggagatg cgacccatga gctgcgagaa   4980
```

-continued

```
ggcgcccagg ccgctctcgt tccagacgcg gctgtagacc acgtccccgt cggcgtcgcg   5040
cgcgcgcatg accacctgcg cgaggttgag ctccacgtgc cgcgcaaaga cggcgtagtt   5100
gcgcaggcgc tggaagaggt agttgagggt ggtggcgatg tgctcggtga cgaagaagta   5160
catgatccag cggcgcaggg gcatctcgct gatgtcgccg atggcttcca gcctttccat   5220
ggcctcgtag aagtccacgg cgaagttgaa aaactgggcg ttgcgggccg agaccgtgag   5280
ctcgtcttcc aggagccgga tgagttcggc gatggtggcg cgcacctcgc gctcgaaatc   5340
cccgggggcc tcctcctctt cctcttcttc catgacgacc tcttcttcta tttcttcctc   5400
tgggggcggt ggtggtggcg gggggccgacg acgacggcga cgcaccggga gacggtcgac   5460
gaagcgctcg atcatctccc cgcggcggcg acgcatggtt tcggtgacgg cgcgaccccg   5520
ttcgcgagga cgcagcgtga agacgccgcc ggtcatctcc cggtaatggg gcgggtcccc   5580
attgggcagc gatagggcgc tgacgatgca tcttatcaat tgcggtgtag ggacgtgag    5640
cgcgtcgaga tcgaccggat cggagaatct ttcgaggaaa gcgtctagcc aatcgcagtc   5700
gcaaggtaag ctcaaacacg tagcagccct gcggacgctg ttagaattgc ggttgctgat   5760
gatgtaattg aagtaggcgt ttttgaggcg gcggatggtg gcgaggagga ccaggtcctt   5820
gggtccagct tgctggatgc ggagccgctc ggccatgccc caggcctggc cctgacaccg   5880
gctcaggttc ttgtagtagt catgcatgag cctctcaatg tcatcactgg ctgaggcgga   5940
gtcttccatg cgggtgaccc cgacgcccct gagcggctgc acgagcgcca ggtcggcgac   6000
gacgcgctcg gcgaggatgg cctgttgcac gcgggtgagg gtgtcctgga agtcgtccat   6060
gtcgacgaag cggtgatagg ccccggtgtt gatggtgtag gtgcagttgg ccatgagcga   6120
ccagttgacg gtctgcaggc ctggctgcac gacctcggag tacctgagcc gcgagaaggc   6180
gcgcgagtcg aagacgtagt cgttgcaggt gcgcacgagg tactggtatc cgactaggaa   6240
gtgcggcggc ggctggcggt agagcggcca gcgctgggtg gccggcgcgc ccggggccag   6300
gtcctcgagc atgaggcggt ggtagccgta gaggtagcgg gacatccagg tgatgccggc   6360
ggcggtggtg gaggcgcgcg ggaactcgcg gacgcggttc cagatgttgc gcagcggcag   6420
gaaatagtcc atggtcggca cggtctggcc ggtgagacgc gcgcagtcat tgacgctcta   6480
gaggcaaaaa cgaaagcggt tgagcgggct cttcctccgt agcctggcgg aacgcaaacg   6540
ggttaggccg cgtgtgtacc ccggttcgag tcccctcgaa tcaggctgga gccgcgacta   6600
acgtggtatt ggcactcccg tctcgacccg agcccgatag ccgccaggat acggcggaga   6660
gccctttttg ccggccgagt ggggtcgcta gacttgaaag cgaccgaaaa ccctgccggg   6720
tagtggctcg cgcccgtagt ctggagaagc atcgccaggg ttgagtcgcg gcagaacccg   6780
gttcgaggac ggccgcggcg agcgggactt ggtcaccccg ccgatataaa gacccacagc   6840
cagccgactt ctccagttac gggagcgagc ccccttttt ctttttgcca gatgcatccc    6900
gtcctgcgcc aaatgcgtcc caccccccg gcgaccaccg cgaccgcggc cgtagcaggc    6960
gccggcgcta gccagccacc acagacagag atggacttgg aagagggcga agggctggca   7020
agactggggg cgccgtcccc ggagcgacat ccccgcgtgc agctgcagaa ggacgtgcgc   7080
ccggcgtacg tgcctacgca gaacctgttc agggaccgca gcggggagga gcccgaggag   7140
atgcgcgact gccggtttcg ggcgggcagg gagctgcgcg agggcctgga ccgccagcgc   7200
gtgctgcgcg acgaggattt cgagccgaac gagcagacgg ggatcagccc cgcacgcgcg   7260
cacgtggcgg cagccaacct ggtgacggcc tacgagcaga cggtgaagca ggagcgcaac   7320
ttccaaaaga gtttcaacaa ccacgtgcgc accctgatcg cgcgcgagga ggtggccctg   7380
```

```
ggcctgatgc acctgtggga cctggcggag gccatcgtgc agaacccgga cagcaagcct   7440
ctgacggcgc agctgttcct ggtggtgcag cacagcaggg acaacgaggc gttcagggag   7500
gcgctgctga acatcgccga gcccgagggt cgctggctgc tggagctgat taacatcttg   7560
cagagcatcg tagtgcagga gcgcagcctg agcctggccg agaaggtggc ggcgatcaac   7620
tactcggtgc tgagcctggg caagttttac gcgcgcaaga tttacaagac gccgtacgtg   7680
cccatagaca aggaggtgaa gatagacagc ttttacatgc gcatggcgct caaggtgctg   7740
acgctgagcg acgacctggg cgtgtaccgc aacgaccgca tccacaaggc cgtgagcacg   7800
agccggcggc gcgagctgag cgaccgcgag ctgatgctga gtctgcgccg ggcgctggta   7860
gggggcgccg ccggcggcga ggagtcctac ttcgacatgg gtgcggacct gcattggcag   7920
ccgagccggc gcgccttgga ggccgcctac ggttcagagg acttggatga ggaagaggaa   7980
gaggaggagg atgcacccgc tgcggggtac tgacgcctcc gtgatgtgtt tttagatgtc   8040
ccagcaagcc ccggaccccg ccataagggc ggcgctgcaa agccagccgt ccggtctagc   8100
atcggacgac tgggaggccg cgatgcaacg catcatggcc ctgacgaccc gcaaccccga   8160
gtcctttaga caacagccgc aggccaacag actctcggcc attctggagg cggtggtccc   8220
ctctcggacc aaccccacgc acgagaaggt gctggcgatc gtgaacgcgc tggcggagaa   8280
caaggccatc cgtcccgacg aggccgggct ggtgtacaac gccctgctgg agcgcgtggg   8340
ccgctacaac agcacgaacg tgcagtccaa cctggatcgg ctggtgacgg acgtgcgcga   8400
ggccgtggcg cagcgcgagc ggttcaagaa cgagggcctg ggctcgctgg tggcgctgaa   8460
cgccttcctg gcgacgcagc cggcgaacgt gccgcgcggg caggacgatt acaccaactt   8520
tatcagcgcg ctgcggctga tggtgaccga ggtgccccag agcgaggtgt accagtctgg   8580
cccggactac tttttccaga cgagccggca gggcttgcag acggtgaacc tgagccaggc   8640
tttcaagaat ctgcgcgggc tgtggggcgt gcaggcgccc gtgggcgacc ggtcaacggt   8700
gagcagcttg ctgacgccca actcgcggct gctgctgctg ctgatcgcgc ccttcaccga   8760
cagcggcagc gtgaaccgca actcgtacct gggccatctg ctgacgctgt accgcgaggc   8820
cataggccag gcgcaggtgg acgagcagac cttccaggag atcactagcg tgagccgcgc   8880
gctggggcag aacgacaccg acagtctgag ggccaccctg aactttttgc tgaccaatag   8940
acagcagaag atcccggcgc agtacgcact gtcggccgag gaggaaagga ttctgagata   9000
tgtgcagcag agcgtagggc tgttcctgat gcaggagggt gccacccccca gcgccgcgct   9060
ggacatgacc gcgcgcaaca tggaacctag catgtacgcc gccaaccggc cgttcatcaa   9120
taagctgatg gactacttgc accgcgcggc ggccatgaac acggactact ttaccaacgc   9180
catcctgaac ccgcactggc tcccgccgcc ggggttctac acgggcgagt acgacatgcc   9240
cgaccccaac gacgggttcc tgtgggacga cgtggacagc gcggtgttct cgccgacctt   9300
tcaaaagcgc caggaggcgc cgccgagcga gggcgcggtg ggaggagcc ccctttcctag   9360
cttagggagt ttgcatagct tgccgggctc ggtgaacagc ggcagggtga gccggccgcg   9420
cttgctgggc gaggacgagt acctgaacga ctcgctgctg cagccgccgc gggccaagaa   9480
cgccatggcc aataacggga tagagagtct ggtggacaaa ctgaaccgct ggaagaccta   9540
cgctcaggac catagggacg cgcccgcgcc gcggcgacag cgccacgacc ggcagcgggg   9600
cctggtgtgg gacgacgagg actcggccga cgatagcagc gtgttggact tgggcgggag   9660
cggtggggtc aacccgttcg cgcatctgca gcccaaactg ggcgacgga tgttttgaat   9720
```

-continued

```
gaaataaaac tcaccaaggc catagcgtgc gttctcttcc ttgttagaga tgaggcgcgc   9780
ggtggtgtct tcctctcctc ctccctcgta cgagagcgtg atggcgcagg cgaccctgga   9840
ggttccgttt gtgcctccgc ggtatatggc tcctacggag ggcagaaaca gcattcgtta   9900
ctcggagctg gctccgcagt acgacaccac tcgcgtgtac ttggtggaca acaagtcggc   9960
ggacatcgct tccctgaact accaaaacga ccacagcaac ttcctgacca cggtggtgca  10020
gaacaacgat ttcacccccg ccgaggccag cacgcagacg ataaattttg acgagcggtc  10080
gcggtggggc ggtgatctga agaccattct gcacactaac atgcccaatg tgaacgagta  10140
catgttcacc agcaagttta aggcgcgggt gatggtgtct aggaagcatc cagagggggt  10200
agttgaaaca gatttgagtc aggataagct tgaatatgag tggtttgagt ttaccctgcc  10260
cgagggaaac ttttccgaga ccatgaccat agacctgatg aacaacgcca tcttggaaaa  10320
ctacttgcaa gtggggcggc agaatggcgt gctggagagc gatatcggag tcaagtttga  10380
cagcagaaat ttcaagctgg gctgggaccc ggtgaccaag ctggtgatgc caggggtcta  10440
cacctacgag gccttccacc cggacgtggt gctgctgccg ggctgcgggg tggacttcac  10500
cgagagccgc ctgagcaacc tcctgggcat tcgcaagaag caacctttcc aagagggctt  10560
cagaatcatg tatgaggatc tagaaggtgg caacatcccc gccctccttg atgtgcccaa  10620
gtacttggaa agcaagaaga aagttgaaga cgaaactaaa aatgcagctg cggccacagc  10680
cgatacaacc actaggggtg atacatttgc aactccagcg caagagacag cagctgataa  10740
gaaggtagaa gtcttgccca ttgaaaagga tgagagtggt agaagttaca acctgatcca  10800
ggggacccac gacacgctgt accgcagttg gtacctgtcc tatacctacg gggaccccga  10860
gaagggggtg cagtcgtgga cgctgctcac caccccggac gttacctgcg gcgcggagca  10920
agtctactgg tcactgccgg acctcatgca agaccccgtc accttccgct ccacccagca  10980
agtcagcaac taccccgtgg tcggcgccga gctcatgccc ttccgcgcca agagctttta  11040
caacgacctc gccgtctact cccagctcat ccgcagctac acctccctca cccacgtctt  11100
caaccgcttc cccgacaacc agatcctctg ccgcccgccc gcgcccacca tcaccaccgt  11160
cagtgaaaac gtgcctgctc tcacagatca cgggacgcta ccgctgcgca gcagtatccg  11220
cggagtccag cgagtgaccg tcactgacgc ccgtcgccgc acctgtccct acgtctacaa  11280
ggccctgggc atagtcgcgc cgcgcgtgct ttccagtcgc accttctaaa aaaatgtcta  11340
ttctcatctc gcccagcaat aacaccggct ggggtcttac tagacccagc accatgtacg  11400
gaggagccaa gaagcgctcc cagcagcacc ccgtccgcgt ccgcggccac ttccgcgctc  11460
cctggggcgc atacaagcgc gggcggactt ccaccgccgc cgtgcgcacc accgtcgacg  11520
acgtcatcga ctcggtggtc gccgacgcgc gcaactatac ccccgccccc tccaccgtgg  11580
acgcggtcat cgacagcgtg gtggccgacg cgcgcgacta tgccagacgc aagagccggc  11640
ggcgacggat cgccaggcgc caccggagca cgcccgccat gcgcgccgcc cgggctctgc  11700
tgcgccgcgc cagacgcacg ggccgccggg ccatgatgcg agccgcgcgc cgcgctgcca  11760
ctgcacccac ccccgcaggc aggactcgca gacgagcggc cgccgccgcc gctgcggcca  11820
tctctagcat gaccagaccc aggcgcggaa acgtgtactg ggtgcgcgac tccgtcacgg  11880
gcgtgcgcgt gcccgtgcgc acccgtcctc ctcgtccctg atctaatgct tgtgtcctcc  11940
cccgcaagcg acgatgtcaa agcgcaaaat caaggaggag atgctccagg tcgtcgcccc  12000
ggagatttac ggaccacccc aggcggacca gaaaccccgc aaaatcaagc gggttaaaaa  12060
aaaggatgag gtggacgagg gggcagtaga gtttgtgcgc gagttcgctc cgcggcggcg  12120
```

-continued

```
cgtaaattgg aaggggcgca gggtgcagcg cgtgttgcgg cccggcacgg cggtggtgtt  12180
cacgcccggc gagcggtcct cggtcaggag caagcgtagc tatgacgagg tgtacggcga  12240
cgacgacatc ctggaccagg cggcggagcg ggcgggcgag ttcgcctacg ggaagcggtc  12300
gcgcgaagag gagctgatct cgctgccgct ggacgaaagc aaccccacgc cgagcctgaa  12360
gcccgtgacc ctgcagcagg tgctgcccca ggcggtgctg ctgccgagcc gcggggtcaa  12420
gcgcgagggc gagagcatgt acccgaccat gcagatcatg gtgcccaagc gccggcgcgt  12480
ggaggacgtg ctggacaccg tgaaaatgga tgtggagccc gaggtcaagg tgcgccccat  12540
caagcaggtg gcgccgggcc tgggcgtgca aaccgtggac attcagatcc ccaccgacat  12600
ggatgtcgac aaaaaaccct cgaccagcat cgaggtgcaa accgacccct ggctcccagc  12660
ctccaccgct accgtctcca cttctaccgc cgccacggct accgagcctc ccaggaggcg  12720
aagatggggc gccgccagcc ggctgatgcc caactacgtg ttgcatcctt ccatcatccc  12780
gacgccgggc taccgcggca cccggtacta cgccagccgc cggcgcccag ccagcaaacg  12840
ccgccgccgc accgccaccc gccgccgtct ggcccccgcc cgcgtgcgcc gcgtgaccac  12900
gcgccggggc cgctcgctcg ttctgcccac cgtgcgctac caccccagca tcctttaatc  12960
cgtgtgctgt gatactgttg cagagagatg gctctcactt gccgcctgcg catccccgtc  13020
ccgaattacc gaggaagatc ccgccgcagg agaggcatgg caggcagcgg cctgaaccgc  13080
cgccggcggc gggccatgcg caggcgcctg agtggcggct ttctgcccgc gctcatcccc  13140
ataatcgccg cggccattgg cacgatcccg ggcatagctt ccgttgcgct gcaggcgtcg  13200
cagcgccgtt gatgtgcgaa taaagcctct ttagactctg acacacctgg tcctgtatat  13260
ttttagaatg gaagacatca attttgcgtc cctggctccg cggcacggca cgcggccgtt  13320
catgggcacc tggaacgaga tcggcaccag ccagctgaac gggggcgcct tcaattggag  13380
cagtgtctgg agcgggctta aaaatttcgg ctcgacgctc cggacctatg ggaacaaggc  13440
ctggaatagt agcacggggc agttgttgag ggaaaagctc aaagaccaga acttccagca  13500
gaaggtggtg gacgggctgg cctcgggcat taacggggtg gtggacatcg cgaaccaggc  13560
cgtgcagcgc gagataaaca gccgcctgga cccgcgaccg cccacggtgg tggagatgga  13620
agatgcaact cttccgccgc ccaagggcga gaagcggccg cggcccgacg cggaggagac  13680
gatcctgcag gtggacgagc cgccctcgta cgaggaggcc gtcaaggccg gcatgcccac  13740
cacgcgcatc atcgcgccgc tggccacggg tgtaatgaaa cccgccaccc ttgacctgcc  13800
tccaccaccc gcgcccgctc caccgaaggc aactccggtt gtgcaggccc ccccggtggc  13860
gaccgccgtg cgccgcgtcc ccgcccgccg ccaggcccag aactggcaga gcacgctgca  13920
cagtatcgtg ggcctgggag tgaaaagtct gaagcgccgc cgatgctatt gagagagagg  13980
aaagaggaca ctaaagggag agcttaactt gtatgtgcct taccgccaga gaacgcgcga  14040
agatggccac cccctcgatg atgccgcagt gggcgtacat gcacatcgcc gggcaggacg  14100
cctcggagta cctgagcccg ggtctggtgc agtttgcccg cgccaccgac acgtacttca  14160
gcctgggcaa caagtttagg aaccccacgg tggccccgac ccacgatgtg accacggacc  14220
ggtcccagcg tctgacgctg cgcttcgtgc ccgtggatcg cgaggacacc acgtactcgt  14280
acaaggcgcg cttcactctg gccgtgggcg acaaccgggt gctagacatg gccagcactt  14340
actttgacat ccgcggcgtc ctggaccgcg gtcccagctt caaaccctac tcgggcacgg  14400
cctacaacag cctggctccc aagggtgccc ccaatcccag tcagtgggaa acaaaagaaa  14460
```

-continued

```
agcaaggaac tactggagga gtgcagcaag aaaaagatgt cacaaaaaca tttggtgtgg  14520
ctgccaccgg cggaattaat ataacaaacc agggtctgtt actaggaact gacgaaaccg  14580
ctgagaatgg caaaaaagac atttatgcag acaagacttt ccagccagaa cctcaagttg  14640
gagaagaaaa ctggcaggaa aatgaagcct tctatggagg aagggctctt aaaaaggaca  14700
ctaaaatgaa accatgctat ggatcttttg ctagacctac taatgagaaa ggaggtcagg  14760
caaagttcaa accagttaat gaaggagaac aacctaaaga tctggatata gattttgctt  14820
actttgacgt ccctggcgga agtcctccag caggtggtag tggggaagaa tacaaagcag  14880
atataatttt gtacactgaa aatgttaatc ttgaaacacc agacactcat gtggtttaca  14940
agccaggaac ttcagataac agttcagaaa tcaatctggt tcagcagtcc atgccaaaca  15000
gacccaacta cattggcttt agggacaact ttgtaggtct catgtattac aacagcaccg  15060
gaaatatggg tgtgctggct ggtcaggctt ctcagttgaa cgctgtggtc gacttgcaag  15120
acagaaacac cgagttatct taccagctat tgctagattc tctgggtgac agaaccagat  15180
actttagcat gtggaactct gcggtggaca gttacgatcc agatgtcagg atcattgaaa  15240
atcacggtgt ggaagatgaa cttccaaact attgcttccc attgaatggc actggaacca  15300
attccactta tcaaggtgta aagattacaa atggtaatga tggtgctgaa gaaagtgagt  15360
gggagaaaga cgatgcaatt tctagacaaa accaaatctg caagggcaat gtctacgcca  15420
tggagatcaa cctgcaggcc aacctgtgga agagttttct gtactcgaac gtggccctgt  15480
acctgcccga ctcctacaag tacacgccgg ccaacgtcaa gctgcccgcc aacaccaaca  15540
cctacgagta catgaacggc cgcgtggtag ccccctcgct ggtggacgcc tacatcaaca  15600
tcggcgcccg ctggtcgttg gaccccatgg acaacgtcaa ccccttcaac caccaccgca  15660
atgcgggcct gcgctaccgc tccatgctgc tgggcaacgg ccgctacgtg cccttccaca  15720
tccaagtgcc ccaaaagttc tttgccatca agaacctgct cctgctcccg ggctcctaca  15780
cctacgagtg gaacttccgc aaggacgtca acatgatcct gcagagttcc ctcggcaacg  15840
acctgcgcgt cgacggcgcc tccgtccgct tcgacagcgt caacctatac gccactttct  15900
tccccatggc gcacaacacc gcttcaacct tggaagccat gctgcgcaac gacaccaacg  15960
accagtcctt caacgactac ctctcggccg ccaacatgct ctaccccatc ccggccaagg  16020
ccaccaacgt gcccatctcc atcccatcgc gcaactgggc cgccttccgc ggctggagtt  16080
tcacccggct caagaccaag gaaactcctt ccctcggctc gggtttcgac ccctactttg  16140
tctactcggg ctccatcccc tacctcgacg ggaccttcta cctcaaccac accttcaaga  16200
aggtctccat catgttcgac tcctcggtca gctggcccgg caacgaccgg ctgctcacgc  16260
cgaacgagtt cgagatcaag cgcagcgtcg acggggaggg ctacaacgtg gcccaatgca  16320
acatgaccaa ggactggttc ctcgtccaga tgctctccca ctacaacatc ggctaccagg  16380
gcttccacgt gcccgagggc tacaaggacc gcatgtactc cttcttccgc aacttccagc  16440
ccatgagcag gcaggtggtc gatgagatca actacaagga ctacaaggcc gtcaccctgc  16500
ccttccagca caataactcg ggcttcaccg gctacctcgc acccaccatg cgccaggggc  16560
agccctaccc cgccaacttc ccctacccgc tcatcggtca gacagccgtg ccctccgtca  16620
cccagaaaaa gttcctctgc gacagggtca tgtggcgcat ccccttctcc agcaacttca  16680
tgtccatggg cgccctcacc gacctgggtc agaacatgct ctacgccaac tcggcccacg  16740
cgctcgacat gaccttcgag gtggacccca tggatgagcc caccctcctc tatcttctct  16800
tcgaagtttt cgacgtggtc agagtacacc agccgcaccg cggcgtcatc gaggccgtct  16860
```

-continued

```
acctgcgcac gcccttctcc gccggcaacg ccaccaccta agcatgagcg gctccagcga  16920
acgagagctc gcggccatcg tgcgcgacct gggctgcggg ccctactttt tgggcaccca  16980
cgacaagcgc ttcccgggct ttctcgccgg cgacaagctg gcctgcgcca tcgtcaacac  17040
ggccggccgc gagaccggag gcgtgcactg gctcgccttc ggctggaacc cgcgctcgcg  17100
cacctgctac atgttcgacc cctttgggtt ctcggaccgc cggctcaagc agatttacag  17160
cttcgagtac gaggccatgc tgcgccgcag cgccctggcc tcctcgcccg accgctgtct  17220
cagcctcgag cagtccactc agaccgtgca ggggcccgac tccgccgcct gcggactctt  17280
ctgttgcatg ttcttgcatg ccttcgtgca ctggcccgac cgacccatgg acggaaaccc  17340
caccatgaac ttgctgacgg gggtgcccaa cggcatgcta caatcgccac aggtgctgcc  17400
caccctcagg cgcaaccagg aggaactcta ccgcttcctc gcgcgccact ccccttactt  17460
tcgctcccac cgcgccgcca tcgaacacgc caccgctttt gacaaaatga aacaactgcg  17520
tgtatctcaa taaacagcac ttttatttta catgcactgg agtatatgca agttatttaa  17580
aagtcgaagg ggttctcgcg ctcgtcgttg tgcgccgcgc tggggagggc cacgttgcgg  17640
tactggtact tgggctgcca cttgaactcg gggatcacca gtttgggcac tggggtctcg  17700
gggaaggtct cgctccacat gcgccggctc atctgcaggg cgcccagcat gtccggggcg  17760
gagatcttga aatcgcagtt ggggccggtg ctctgcgcgc gcgagttgcg gtacacgggg  17820
ttgcagcact ggaacaccat cagactgggg tacttcacac tagccagcac gctcttgtcg  17880
ctgatctgat ccttgtccag atcctcggcg ttgctcaggc cgaacggggt catcttgcac  17940
agctggcgtc ccaggaaggg cacgctctga ggcttgtggt tacactcgca gtgcacgggc  18000
atcagcatca tccccgcgcc gcgctgcata ttcgggtaga gggccttgac aaaggccgcg  18060
atctgcttga aagcttgctg ggccttggcc ccctcgctga aaaacaggcc gcagctcttc  18120
ccgctgaact ggttattccc acacccggca tcctgcacgc agcagcgcgc gtcatggctg  18180
gtcagttgca ccacgctccg tccccagcgg ttctgggtca ccttagcctt gctgggctgc  18240
tccttcaacg cgcgctgccc gttctcgctg gtcacatcca tctccaccac gtggtccttg  18300
tggatcatca tcgtcccgtg cagacacttg agctggcctt ccacctcggt gcagccgtga  18360
tcccacaggg cgcaaccggt gcactcccag ttcttgtgcg caatcccgct gtggctgaag  18420
atgtaacctt gcaacatgcg gcccatgatg gtgctaaatg ctttctgggt ggtgaaggtc  18480
agttgcatcc cgcgggcctc ctcgttcatc caggtctggc acatcttctg gaagatctcg  18540
gtctgctcgg gcatgagctt gtaagcatcg cgcaggccgc tgtcgacgcg gtagcgttcc  18600
atcagcacgt tcatggtatc catgcccttc tcccaggacg agaccagagg cagactcaga  18660
gggttgcgta cgttcaggac accgggggtc gcgggctcga cgatgcgttt tccgtccttg  18720
ccttccttca atagaaccgg cggctggctg aatcccactc ccacgatcac ggcatcttcc  18780
tggggcatct cttcgtcggg gtctaccttg gtcacatgct tggtctttct ggcttgcttc  18840
tttttggag ggctgtccac ggggagcacg tcctcctcgg aagacccgga gcccacccgc  18900
tgatactttc ggcgcttggt gggcagagga ggtggcggcg aggggctcct ctcctgctcc  18960
ggcggatagc gcgccgaccc gtggccccgg ggcggagtgg cctctcggcc catgaaccgg  19020
cgcacgtcct gactgccgcc ggccattgtt tcctagggga agatggagga gcagccgcgt  19080
aagcaggagc aggaggagga cttaaccacc cacgagcaac ccaaaatcga gcaggacctg  19140
ggcttcgaag agccggctcg tctagaaccc ccacaggatg aacaggagca cgagcaagac  19200
```

-continued

```
gcaggccagg aggagaccga cgctgggctc gagcatggct acctgggagg agaggaggat  19260
gtgctgctga aacacctgca gcgccagtcc ctcatcctcc gggacgccct ggccgaccgg  19320
agcgaaaccc ccctcagcgt cgaggagctg tgtcgggcct acgagctcaa cctcttctcg  19380
ccgcgcgtac cccccaaacg ccagcccaac ggcacctgcg agcccaaccc gcgtctcaac  19440
ttctatcccg tctttgcggt ccccgaagcc ctcgccacct atcacatctt tttcaagaac  19500
caaaagatcc ccgtctcctg ccgcgccaac cgcaccagcg ccgacgcgct cctcgctttg  19560
gggcccggcg cgcgcatacc tgatatcgct tccctggaag aggtgcccaa gatcttcgaa  19620
gggctcggtc gggacgagac gcgcgcggcg aacgctctga aagaaacagc agaggaagag  19680
ggtcacacta gcgccctggt agagttggaa ggcgacaacg ccaggctggc cgtgctcaag  19740
cgcagcgtcg agcttaccca cttcgcctac cccgccgtca acctcccgcc caaggtcatg  19800
cgtcgcatca tggatcagct catcatgccc cacatcgagg ccctcgatga aagtcaggag  19860
cagcgccccg aggacgcccg gcccgtggtc agcgacgaga tgctcgcgcg ctggctcggg  19920
acccgcgacc cccaggcttt ggaacagcgg cgcaaactca tgctggccgt ggtcctggtc  19980
acccttgagc tcgaatgcat gcgccgcttt ttcagcgacc ccgagaccct gcgcaaggtc  20040
gaggagaccc tgcactacac tttcaggcac ggtttcgtca ggcaggcctg caagatctcc  20100
aacgtggagc tgaccaacct ggtctcctgc ctggggatcc tgcacgagaa ccgcctgggc  20160
cagaccgtgc tccactctac cctgaagggc gaggcgcggc gggactatgt ccgcgactgc  20220
gtctttctct ttctctgcca cacatggcaa gcggccatgg gcgtgtggca gcagtgtctc  20280
gaggacgaga acctaaagga gctggacaag cttcttgcta gaaaccttaa aaagctgtgg  20340
acgggcttcg acgagcgcac cgtcgcctcg gacctggccg agatcgtctt ccccgagcgc  20400
ctgagacaga cgctgaaagg cgggctgccc gacttcatga gccagagcat gttgcaaaac  20460
taccgcactt tcattcttga gcgatcaggc atcctgcccg ccacctgcaa cgccttcccc  20520
tccgactttg taccgctgag ctaccgcgag tgtcccccgc cgctgtggag ccactgctac  20580
ctcttgcagc tggccaacta catcgcctac cactcggacg tgatcgagga cgtgagcggc  20640
gaggggctgc tcgagtgcca ctgtcgctgc aacctgtgct ccccgcatcg ctccctggtc  20700
tgcaaccccc agctcctgag cgagacccag gtcatcggta ccttcgagct gcaaggtccg  20760
caggagtcca ccgctccgct gaaactcacg ccggggttgt ggacttccgc gtacctgcgc  20820
aaatttgtac ccgaagacta ccacgcccat gagataaagt tctttgagga ccaatcgcgt  20880
ccgcagcacg cggatctcac ggcctgcgtc atcacccagg gcgcgatcct cgcccaattg  20940
cacgccatcc aaaaatcccg ccaagagttt cttctgaaaa agggtagagg ggtctacctg  21000
gacccccaga cgggcgaggt gctcaacccg ggtctccccc agcatgccga ggaagaagca  21060
ggagccgcta gtggaggaga tggaagaaga atgggacagc caggcagagg aggacgaatg  21120
ggaggaggag acagaggagg aagaattgga agaggtggaa gaggagcagg caacagagca  21180
gcccgtcgcc gcaccatccg cgccggcagc cccgccggtc acggatacaa cctccgctcc  21240
ggtcaagcct cctcgtagat gggatcaagt gaagggtgac ggtaagcacg agcggcaggg  21300
ctaccgatca tggagggccc acaaagccgc gatcatcgcc tgcttgcaag actgcggggg  21360
gaacatcgct ttcgcccgcc gctacctgct cttccaccgc ggggtgaaca tcccccgcaa  21420
cgtgttgcat tactaccgtc accttcacag ctaagaaaaa gcaagtcaaa ggagtcgccg  21480
gaggaggagg aggaggcctg aggatcgcgg cgaacgagcc cttgaccacc agggagctga  21540
ggaaccggat cttccccact ctttatgcca tttttcagca gagtcgaggt cagcagcaag  21600
```

-continued

```
agctcaaagt aaaaaaccgg tctctgcgct cgctcacccg cagttgcttg taccacaaaa  21660
acgaagatca gctgcagcgc actctcgaag acgccgaggc tctgttccac aagtactgcg  21720
cgctcactct taaagactaa ggcgcgccca cccggaaaaa aggcgggaat tacctcatcg  21780
ccaccatgag caaggagatt cccacccctt acatgtggag ctatcagccc caaatgggcc  21840
tggccgcggg cgcctcccag gactactcca cccgcatgaa ctggctcagt gccggcccct  21900
cgatgatctc acgggtcaac ggggtccgca gtcatcgaaa ccagatattg ttggagcagg  21960
cggcggtcac ctccacgccc agggcaaagc tcaacccgcg taattggccc tccaccctgg  22020
tgtatcagga aatccccggg ccgactaccg tactacttcc gcgtgacgca ctggccgaag  22080
tccgcatgac taactcaggt gtccagctgg ccggcggcgc ttcccggtgc ccgctccgcc  22140
cacaatcggg tataaaaacc ctggtgatcc gaggcagagg cacacagctc aacgacgagt  22200
tggtgagctc ttcgatcggt ctgcgaccgg acggagtgtt ccaactagcc ggagccggga  22260
gatcctcctt cactcccaac caggcctacc tgaccttgca gagcagctct tcggagcctc  22320
gctccggagg catcggaacc ctccagtttg tggaggagtt tgtgccctcg gtctacttca  22380
accccttctc gggatcgcca ggcctctacc cggacgagtt cataccgaac ttcgacgcag  22440
tgagagaagc ggtggacggc tacgactgaa tgtcccatgg tgactcggct gagctcgctc  22500
ggttgaggca tctggaccac tgccgccgcc tgcgctgctt cgcccgggag agctgcggac  22560
tcatctactt tgagtttccc gaggagcacc ccaacggccc tgcacacgga gtgcggatca  22620
ccgtagaggg caccaccgag tctcacctgg tcaggttctt cacccagcaa cccttcctgg  22680
tcgagcggga ccggggcgcc accacctaca ccgtctactg catctgtcca accccgaagt  22740
tgcatgagaa tttttgttgt actctttgtg gtgagtttaa taaaagctaa actcttgcaa  22800
tactctggac cttgtcgtcg tcaactcaac gagaccgtct acctcaccaa ccagactgag  22860
gtaaaactca cctgcagacc acacaagacc tatatcatct ggttcttcga gaacacctca  22920
tttgcagtct ccaacactca ctgcactagt ccatgaactg atgttgatta aaagcccaaa  22980
aaccaatcag ccccttcccc catttcccca tcccccaatt actcataaaa aataaatcat  23040
tggaattaat cattcaataa agatcactta cttgaaatct gaaagtatgt ctctggtgta  23100
gttgttcagc agcacctcgg taccctcctc ccagctctgg tactccagtc cccggcgggc  23160
ggcgaacttc ctccacacct tgaaagggat gtcaaattcc tggtccacaa ttttcattgt  23220
cttccctctc agatggcaaa gaggctccgg gtggaagatg acttcaaccc cgtctacccc  23280
tatggctacg cgcggaatca gaatatcccc ttcctcactc cccccttgt ctcctccgat  23340
ggattcaaaa acttcccccc tggggtcctg tcacttaaac tggctgatcc aatcaccatc  23400
aacaatgggg atgtctcact taaggtggga gggggacttg ctgtagagca acagactggt  23460
aacctaagcg taaaccctga tgcacccttg caagttgcaa gtgataagct acagcttgct  23520
ctggctcctc cattcgaggt cagagatgga aagcttgctt taaaggcagg taatggatta  23580
aaagtactag ataattccat tactggattg actggattat tgaatacact tgtggtatta  23640
actggaaggg gaataggaac ggaggaatta aaaaatgacg atggtgtaac aaacaaagga  23700
gtcggcttgc gtgtaagact tggagatgac ggcgggctga catttgataa aaagggtgat  23760
ttagtagcct ggaataaaaa agatgacagg cgcaccctgt ggacaacccc tgacacatct  23820
ccaaattgca aaatgagtac agaaaaggat tctaaactta cgttgacact tacaaagtgt  23880
ggaagtcagg ttctgggaaa tgtatcttta cttgcagtta caggtgaata tcatcaaatg  23940
```

```
actgctacta caaagaagga tgtaaaaata tctttactat ttgatgagaa tggaattcta  24000
ttaccatctt cgtcccttag caaagattat tggaattaca gaagtgatga ttctattgta  24060
tctcaaaaat ataataatgc agttccattc atgccaaacc tgacagctta tccaaaacca  24120
agcgctcaaa atgcaaaaaa ctattcaaga actaaaatca taagtaatgt ctacttaggt  24180
gctcttacct accaacctgt aattatcact attgcattta atcaggaaac tgaaaatgga  24240
tgtgcttatt ctataacatt taccttcact tggcaaaaag actattctgc ccaacagttt  24300
gatgttacat cttttacctt ctcatatctt acccaagaga acaaagacaa agactaataa  24360
aatgttttga actgaattta tgaatcttta tttattttta caccagcacg ggtagtcagt  24420
ttcccaccac cagcccattt cacagtgtaa acagtccttt ctccccggct ggccttaaaa  24480
agcatcatat catgggtaac agacatattc ttaggtgtta tattccacac ggtttcctgt  24540
cgagccaaac gctcatcagt gatattaata aactccccgg gcagctcact taagttcatg  24600
tcgctgtcca gctgctgagc cacaggctgc tgtccaactt gcggttgctt aacgggcggc  24660
gaaggagaag tccacgccta catgggggta gagtcataat cgtgcatcag gatagggcgg  24720
tggtgctgca gcagcgcgcg aataaactgc tgccgccgcc gctccgtcct gcaggaatac  24780
aacatggcag tggtctcctc agcgatgatt cgcaccgccc gcagcataag gcgccttgtc  24840
ctccgggcac agcagcgcac cctgatctca cttaaatcag cacagtaact gcagcacagc  24900
accacaatat tgttcaaaat cccacagtgc aaggcgctgt atccaaagct catggcgggg  24960
accacagaac ccacgtggcc atcataccac aagcgcaggt agattaagtg gcgacccctc  25020
ataaacacgc tggacataaa cattacctct tttggcatgt tgtaattcac cacctcccgg  25080
taccatataa acctctgatt aaacatggcg ccatccacca ccatcctaaa ccagctggcc  25140
aaaacctgcc cgccggctat acactgcagg gaaccgggac tggaacaatg acagtggaga  25200
gcccaggact cgtaaccatg gatcatcatg ctcgtcatga tatcaatgtt ggcacaacac  25260
aggcacacgt gcatacactt cctcaggatt acaagctcct cccgcgttag aaccatatcc  25320
cagggaacaa cccattcctg aatcagcgta aatcccacac tgcagggaag acctcgcacg  25380
taactcacgt tgtgcattgt caaagtgtta cattcgggca gcagcggatg atcctccagt  25440
atggtagcgc gggtttctgt ctcaaaagga ggtagacgat ccctactgta cggagtgcgc  25500
cgagacaacc gagatcgtgt tggtcgtagt gtcatgccaa atggaacgcc ggacgtagtc  25560
attgaaatgg attctcttgc gtaccttgtc gtacttctgc cagcagaaag tggctcggga  25620
acagcagata cctttcctcc tgctgtcctt ccgctgctga cgctcagtca tccaactgaa  25680
gtacagccat tcccgcaggt tctccagcag ctcctgtgca tctgatgaaa caaaagtccc  25740
gtcgatgcgg attcccctta aacatcagc caggacattg taggccatcc caatccagtt  25800
aatgcatcct gatctatcat gaagaggagg tgggggaaga actggaagaa ccatttttat  25860
tccaagcggt ctcgaaggac gataaagtgc aagtcacgca ggtgacagcg ttccccgccg  25920
ctgtgctggt ggaaacagac agccaggtca aaacccactc tattttcaag gtgctcgact  25980
gtggcttcga gcagtggctc tacgcgtaca tccagcataa gaatcacatt aaaggctgga  26040
cctccatcga tttcatcaat catcaggtta cactcattca ccatccccag gtaattctca  26100
tttttccagc cttggattat ttctacaaat tgttggtgta agtccactcc gcacatgtgg  26160
aaaagttccc acagcgcccc ctccactttc ataatcaggc agaccttcat attagaaaca  26220
gatcctgctg ctccaccacc tgcagcgtgt tcaaaacaac aagattcaat gaggttctgc  26280
cctctgccct cagctcacgt ctcagcgtca gctgcaaaaa gtcactcaag tcctcagcca  26340
```

```
ctacagctga caattcagag ccagggctaa gcgtgggact ggcaagcgtg agtgagtact  26400
ttaatgctcc aaagctagca cccaaaaact gcatgctgga ataagctctc tttgtgtcac  26460
cggtgatgcc ttccaatagg tgagtgataa agcgaggtag tttttcttta atcatttgag  26520
taatagaaaa gtcctctaaa taagtcacta ggaccccagg aaccacaatg tggtagctga  26580
cagcgtgtcg ctcaagcatg gttagtagag atgagagtct gaaaaacaga aagcatgcac  26640
taaaccagag ttgccagtct cactgaagga aaaatcactc tctccagcag caaagtgccc  26700
actgggtggc cctctcggac atacaaaaat cgatccgtgt ggttaaagag cagcacagtt  26760
agctcctgtc ttctcccagc aaagatcaca tcggactggg ttagtatgcc cctggaatgg  26820
tagtcattca aggccataaa tctgccttgg tagccattag gaatcagcac gctcactctc  26880
aagtgaacca aaaccacccc atgcggagga atgtggaaag attctgggca aaaaaaggta  26940
tatctattgc tagtcccttc ctggacggga gcaatccctc cagggctatc tatgaaagca  27000
tacagagatt cagccatagc tcagcccgct taccagtaga cagagagcac agcagtacaa  27060
gcgccaacag cagcgactga ctacccactg acccagctcc ctatttaaag gcaccttaca  27120
ctgacgtaat gaccaaaggt ctaaaaaccc cgccaaaaaa acacacacgc cctgggtgtt  27180
tttcgcgaaa acacttccgc gttctcactt cctcgtatcg atttcgtgac tcaacttccg  27240
ggttcccacg ttacgtcact tctgcccctta catgtaactc agccgtaggg cgccatcttg  27300
cccacgtcca aaatggcttc catgtccggc cacgcctccg cggcgaccgt tagccgtgcg  27360
tcgtgacgtc atttgcatca ccgtttctcg tccaatcagc gttggctccg ccccaaaacc  27420
gttaaaattc aaaagctcat ttgcatatta acttttgttt actttgtggg gtatattatt  27480
gatgatgtta attaagacaa ttcttgaaga cgaaagggcc tcgtgatacg cctattttta  27540
taggttaatg tcatgataat aatggtttct tagacgtcag gtggcacttt tcggggaaat  27600
gtgcgcggaa cccctatttg tttatttttc taaatacatt caaatatgta tccgctcatg  27660
agacaataac cctgataaat gcttcaataa tattgaaaaa ggaagagtat gagtattcaa  27720
catttccgtg tcgcccttat tccctttttt gcggcatttt gccttcctgt ttttgctcac  27780
ccagaaacgc tggtgaaagt aaaagatgct gaagatcagt tgggtgcacg agtgggttac  27840
atcgaactgg atctcaacag cggtaagatc cttgagagtt ttcgccccga agaacgtttt  27900
ccaatgatga gcacttttaa agttctgcta tgtggcgcgg tattatcccg tgttgacgcc  27960
gggcaagagc aactcggtcg ccgcatacac tattctcaga atgacttggt tgagtactca  28020
ccagtcacag aaaagcatct tacggatggc atgacagtaa gagaattatg cagtgctgcc  28080
ataaccatga gtgataacac tgcggccaac ttacttctga caacgatcgg aggaccgaag  28140
gagctaaccg cttttttgca caacatgggg gatcatgtaa ctcgccttga tcgttgggaa  28200
ccggagctga atgaagccat accaaacgac gagcgtgaca ccacgatgcc tgcagcaatg  28260
gcaacaacgt tgcgcaaact attaactggc gaactactta ctctagcttc ccggcaacaa  28320
ttaatagact ggatggaggc ggataaagtt gcaggaccac ttctgcgctc ggcccttccg  28380
gctggctggt ttattgctga taaatctgga gccggtgagc gtgggtctcg cggtatcatt  28440
gcagcactgg ggccagatgg taagccctcc cgtatcgtag ttatctacac gacggggagt  28500
caggcaacta tggatgaacg aaatagacag atcgctgaga taggtgcctc actgattaag  28560
cattggtaac tgtcagacca agtttactca tatatacttt agattgattt aaaacttcat  28620
ttttaattta aaaggatcta ggtgaagatc ctttttgata atctcatgac caaaatccct  28680
```

taacgtgagt tttcgttcca ctgagcgtca gaccccgtag aaaagatcaa aggatcttct 28740
tgagatcctt tttttctgcg cgtaatctgc tgcttgcaaa caaaaaaacc accgctacca 28800
gcggtggttt gtttgccgga tcaagagcta ccaactcttt ttccgaaggt aactggcttc 28860
agcagagcgc agataccaaa tactgtcctt ctagtgtagc cgtagttagg ccaccacttc 28920
aagaactctg tagcaccgcc tacatacctc gctctgctaa tcctgttacc agtggctgct 28980
gccagtggcg ataagtcgtg tcttaccggg ttggactcaa gacgatagtt accggataag 29040
gcgcagcggt cgggctgaac ggggggttcg tgcacacagc ccagcttgga gcgaacgacc 29100
tacaccgaac tgagatacct acagcgtgag ctatgagaaa gcgccacgct tcccgaaggg 29160
agaaaggcgg acaggtatcc ggtaagcggc agggtcggaa caggagagcg cacgagggag 29220
cttccagggg gaaacgcctg gtatctttat agtcctgtcg ggtttcgcca cctctgactt 29280
gagcgtcgat ttttgtgatg ctcgtcaggg gggcggagcc tatggaaaaa cgccagcaac 29340
gcggcctttt tacggttcct ggccttttgc tggccttttg ctggcctttt gctcacatgt 29400
tctttcctgc gttatcccct gattctgtgg ataaccgtat taccgccttt gagtgagctg 29460
ataccgctcg ccgcagccga acgaccgagc gcagcgagtc agtgagcgag gaagcggaag 29520
agcgctgact tccgcgtttc cagactttac gaaacacgga aaccgaagac cattcatgtt 29580
gttgctcagg tcgcagacgt tttgcagcag cagtcgcttc acgttcgctc gcgtatcggt 29640
gattcattct gctaaccagt aaggcaaccc cgccagccta gccgggtcct caacgacagg 29700
agcacgatca tgcgcacccg tcagatccag acatgataag atacattgat gagtttggac 29760
aaaccacaac tagaatgcag tgaaaaaaat gctttatttg tgaaatttgt gatgctattg 29820
ctttatttgt aaccattata agctgcaata aacaagttaa caacaacaat tgcattcatt 29880
ttatgtttca ggttcagggg gaggtgtggg aggtttttta aagcaagtaa aacctctaca 29940
aatgtggtat ggctgattat gatctctagt caaggcacta tacatcaaat attccttatt 30000
aaccccttta caaattaaaa agctaaaggt acacaatttt tgagcatagt tattaatagc 30060
agacactcta tgcctgtgtg gagtaagaaa aaacagtatg ttatgattat aactgttatg 30120
cctacttata aaggttacag aatatttttc cataattttc ttgtatagca gtgcagcttt 30180
ttcctttgtg gtgtaaatag caaagcaagc aagagttcta ttactaaaca cagcatgact 30240
caaaaaactt agcaattctg aaggaaagtc cttggggtct tctacctttc tcttcttttt 30300
tggaggagta gaatgttgag agtcagcagt agcctcatca tcactagatg gcatttcttc 30360
tgagcaaaac aggttttcct cattaaaggc attccaccac tgctcccatt catcagttcc 30420
ataggttgga atctaaaata cacaaacaat tagaatcagt agtttaacac attatacact 30480
taaaaatttt atatttacct tagagcttta aatctctgta ggtagtttgt ccaattatgt 30540
cacaccacag aagtaaggtt ccttcacaaa gatccggacc aaagcggcca tcgtgcctcc 30600
ccactcctgc agttcggggg catggatgcg cggatagccg ctgctggttt cctggatgcc 30660
gacggatttg cactgccggt agaactccgc gaggtcgtcc agcctcaggc agcagctgaa 30720
ccaactcgcg aggggatcga gcccggggtg ggcgaagaac tccagcatga gatccccgcg 30780
ctggaggatc atccagccgg cgtcccggaa aacgattccg aagcccaacc tttcatagaa 30840
ggcggcggtg gaatcgaaat ctcgtgatgg caggttgggc gtcgcttggt cggtcatttc 30900
gaaccccaga gtcccgctca gaagaactcg tcaagaaggc gatagaaggc gatgcgctgc 30960
gaatcgggag cggcgatacc gtaaagcacg aggaagcggt cagcccattc gccgccaagc 31020
tcttcagcaa tatcacgggt agccaacgct atgtcctgat agcggtccgc cacacccagc 31080

-continued

```
cggccacagt cgatgaatcc agaaaagcgg ccattttcca ccatgatatt cggcaagcag  31140
gcatcgccat gggtcacgac gagatcctcg ccgtcgggca tgcgcgcctt gagcctggcg  31200
aacagttcgg ctggcgcgag cccctgatgc tcttcgtcca gatcatcctg atcgacaaga  31260
ccggcttcca tccgagtacg tgctcgctcg atgcgatgtt tcgcttggtg gtcgaatggg  31320
caggtagccg gatcaagcgt atgcagccgc cgcattgcat cagccatgat ggatactttc  31380
tcggcaggag caaggtgaga tgacaggaga tcctgccccg gcacttcgcc caatagcagc  31440
cagtcccttc ccgcttcagt gacaacgtcg agcacagctg cgcaaggaac gcccgtcgtg  31500
gccagccacg atagccgcgc tgcctcgtcc tgcagttcat tcagggcacc ggacaggtcg  31560
gtcttgacaa aaagaaccgg gcgcccctgc gctgacagcc ggaacacggc ggcatcagag  31620
cagccgattg tctgttgtgc ccagtcatag ccgaatagcc tctccaccca agcggccgga  31680
gaacctgcgt gcaatccatc ttgttcaatc atgcgaaacg atcctcatcc tgtctcttga  31740
tcagatcttg atcccctgcg ccatcagatc cttggcggca agaaagccat ccagtttact  31800
ttgcagggct tcccaacctt accagagggc gccccagctg gcaattccgg ttcgcttgct  31860
gtccataaaa ccgcccagtc tagctatcgc catgtaagcc cactgcaagc tacctgcttt  31920
ctctttgcgc ttgcgttttc ccttgtccag atagcccagt agctgacatt catccggggt  31980
cagcaccgtt tctgcggact ggctttctac gtgttccgct tcctttagca gcccttgcgc  32040
cctgagtgct tgcggcagcg tgaagctttt tgcaaaagcc taggcctcca aaaaagcctc  32100
ctcactactt ctggaatagc tcagaggccg aggcggcctc ggcctctgca taaataaaaa  32160
aaattagtca gccatggggc ggagaatggg cggaactggg cggagttagg ggcgggatgg  32220
gcggagttag gggcgggact atggttgctg actaattgag atgcatgctt tgcatacttc  32280
tgcctgctgg ggagcctggg gactttccac acctggttgc tgactaattg agatgcatgc  32340
tttgcatact tctgcctgct ggggagcctg gggactttcc acaccctaac tgacacacat  32400
tccacagccg gatctgcagg acccaacgct gcccgagatg cgccgcgtgc ggctgctgga  32460
gatggcggac gcgatggata tgttctgcca agggttggtt tgcgcattca cagttctccg  32520
caagaattga ttggctccaa ttcttggagt ggtgaatccg ttagcgaggt gccgccggct  32580
tccattcagg tcgaggtggc ccggctccat gcaccgcgac gcaacgcggg gaggcagaca  32640
aggtataggg cggcgcctac aatccatgcc aacccgttcc atgtgctcgc cgaggcggca  32700
taaatcgccg tgacgatcag cggtccaatg atcgaagtta ggctggtaag agccgcgagc  32760
gatccttgaa gctgtccctg atggtcgtca tctacctgcc tggacagcat ggcctgcaac  32820
gcgggcatcc cgatgccgcc ggaagcgaga agaatcataa tggggaaggc catccagcct  32880
cgcgtcgcga acgccagcaa gacgtagccc agcgcgtcgg ccgccatgcc ggcgataatg  32940
gcctgcttct cgccgaaacg tttggtggcg ggaccagtga cgaaggcttg agcgagggcg  33000
tgcaagattc cgaataccgc aagcgacagg ccgatcatcg tcgcgctcca gcgaaagcgg  33060
tcctcgccga aaatgaccca gagcgctgcc ggcacctgtc ctacgagttg catgataaag  33120
aagacagtca taagtgcggc gacgatagtc atgccccgcg cccaccggaa ggagctgact  33180
gggttgaagg ctctcaaggg catcggtcga cgctctccct tatgcgactc ctgcattagg  33240
aagcagccca gtagtaggtt gaggccgttg agcaccgccg ccgcaaggaa tggtgcatgc  33300
aaggagatgg cgcccaacag tcccccggcc acggggcctg ccaccatacc cacgccgaaa  33360
caagcgctca tgagcccgaa gtggcgagcc cgatcttccc catcggtgat gtcggcgata  33420
```

-continued taggcgccag caaccgcacc tgtggcgccg gtgatgccgg ccacgatgcg tccggcgtag 33480
aggatcttgg cagtcacagc atgcgcatat ccatgcttcg accatgcgct cacaaagtag 33540
gtgaatgcgc aatgtagtac ccacatcgtc atcgctttcc actgctctcg cgaataaaga 33600
tggaaaatca atctcatggt aatagtccat gaaaatcctt gtattcataa atcctccagg 33660
tagctatatg caaattgaaa caaaagagat ggtgatcttt ctaagagatg atggaatctc 33720
ccttcagtat cccgatggtc aatgcgctgg atatgggata gatgggaata tgctgatttt 33780
tatgggacag agttgcgaac tgttcccaac taaaatcatt ttgcacgatc agcgcactac 33840
gaactttacc cacaaatagt caggtaatga atcctgatat aaagacaggt tgataaatca 33900
gtcttctacg cgcatcgcac gcgcacaccg tagaaagtct ttcagttgtg agcctgggca 33960
aaccgttaac tttcggcggc tttgctgtgc gacaggctca cgtctaaaag gaaataaatc 34020
atgggtcata aaattatcac gttgtccggc gcggcgacgg atgttctgta tgcgctgttt 34080
ttccgtggcg cgttgctgtc tggtgatctg ccttctaaat ctggcacagc cgaattgcgc 34140
gagcttggtt ttgctgaaac cagacacaca gcaactgaat accagaaaga aaatcacttt 34200
acctttctga catcagaagg gcagaaattt gccgttgaac acctggtcaa tacgcgtttt 34260
ggtgagcagc aatattgcgc ttcgatgacg cttggcgttg agattgatac ctctgctgca 34320
caaaaggcaa tcgacgagct ggaccagcgc attcgtgaca ccgtctcctt cgaacttatt 34380
cgcaatggag tgtcattcat caaggacgcc gctatcgcaa atggtgctat ccacgcagcg 34440
gcaatcgaaa cacctcagcc ggtgaccaat atctacaaca tcagccttgg tatccagcgt 34500
gatgagccag cgcagaacaa ggtaaccgtc agtgccgata agttcaaagt taaacctggt 34560
gttgatacca acattgaaac gttgatcgaa aacgcgctga aaaacgctgc tgaatgtgcg 34620
gcgctggatg tcacaaagca aatggcagca gacaagaaag cgatggatga actggcttcc 34680
tatgtccgca cggccatcat gatggaatgt ttccccggtg gtgttatctg gcagcagtgc 34740
cgtcgatagt atgcaattga taattattat catttgcggg tcctttccgg cgatccgcct 34800
tgttacgggg cggcgacctc gcgggttttc gctatttatg aaaattttcc ggtttaaggc 34860
gtttccgttc ttcttcgtca taacttaatg tttttattta aaataccctc tgaaaagaaa 34920
ggaaacgaca ggtgctgaaa gcgagctttt tggcctctgt cgtttccttt ctctgttttt 34980
gtccgtggaa tgaacaatgg aagtcaacaa aaagcagctg gctgacattt tcggtgcgag 35040
tatccgtacc attcagaact ggcaggaaca gggaatgccc gttctgcgag gcggtggcaa 35100
gggtaatgag gtgctttatg actctgccgc cgtcataaaa tggtatgccg aaagggatgc 35160
tgaaattgag aacgaaaagc tgcgccggga ggttgaagaa ctgcggcagg ccagcgaggc 35220
agatccacag gacgggtgtg gtcgccatga tcgcgtagtc gatagtggct ccaagtagcg 35280
aagcgagcag gactgggcgg cggccaaagc ggtcggacag tgctccgaga acgggtgcgc 35340
atagaaattg catcaacgca tatagcgcta gcagcacgcc atagtgactg gcgatgctgt 35400
cggaatggac gatatcccgc aagaggcccg gcagtaccgg cataaccaag cctatgccta 35460
cagcatccag ggtgacggtg ccgaggatga cgatgagcgc attgttagat ttcatacacg 35520
gtgcctgact gcgttagcaa tttaactgtg ataaactacc gcattaaagc ttatcgatga 35580
taagcggtca aacatgagaa ttgcgg 35606

<210> SEQ ID NO 20
<211> LENGTH: 19
<212> TYPE: DNA
<213> ORGANISM: Artificial Sequence -continued

```
<220> FEATURE:
<223> OTHER INFORMATION: TetO sequence

<400> SEQUENCE: 20

tccctatcag tgatagaga                                                    19
```

RECOMBINANT ADENOVIRAL VECTOR EXPRESSING ZIKA ANTIGEN WITH IMPROVED PRODUCTIVITY

CROSS-REFERENCE TO RELATED APPLICATION

This application is a Section 371 of International Application No. PCT/EP2019/069461, filed Jul. 19, 20019, that was published in the English language on Jan. 23, 2020, under International Publication No. WO 2020/016394 A1, and claims priority under 35 U.S.C. § 119(b) to U.S. Provisional Patent Application No. 62/701,403, filed Jul. 20, 2018, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "CRU6001USPCT1 Sequence Listing" and a creation date of Jan. 19, 2021 and having a size of about 150 kb. The sequence listing submitted via EFS-Web is part of the specification and is herein incorporated by reference in its entirety.

FIELD OF THE INVENTION

This invention relates to biotechnology. More particularly, to the field and use of adenoviral vectors comprising a nucleotide sequence encoding a Zika virus (ZIKV) M and Env antigen operably linked to a nucleotide sequence comprising a cytomegalovirus (CMV) promoter comprising at least one tetracycline operator. Methods of administering pharmaceutical compositions comprising the adenovirus vectors or adenoviral particles comprising the ZIKV M and Env antigens to prevent or reduce the progression of a ZIKV infection and/or symptoms caused by a ZIKV infection are also provided.

BACKGROUND OF THE INVENTION

Zika virus (ZIKV) is a flavivirus that is responsible for an unprecedented current epidemic in Brazil and the Americas. ZIKV has been causally associated with microcephaly, intrauterine growth restriction, and other birth defects in humans and in murine models. ZIKV is believed to cause neuropathology in developing fetuses by crossing the placenta and targeting cortical neural progenitor cells, leading to impaired neurogenesis and resulting in microcephaly and other congenital malformations.

The World Health Organization declared the clusters of microcephaly and neurological disorders and their association with ZIKV infection to be a global public health emergency on Feb. 1, 2016. ZIKV also has been associated with neurologic conditions such as Guillain-Barré syndrome. While the rapid development of a safe and effective ZIKV vaccine is a global health priority, very little is currently known about ZIKV immunology and mechanisms of immune protection.

Accordingly, there is an unmet need in the field of ZIKV vaccines.

The foregoing discussion is presented solely to provide a better understanding of the nature of the problems confronting the art and should not be construed in any way as an admission that such reference constitutes "prior art" to the instant application.

BRIEF SUMMARY OF THE INVENTION

Provided herein are adenoviral vectors comprising a nucleotide sequence encoding a Zika virus M and Env antigen, wherein the nucleotide sequence encoding the Zika virus M and Env antigen is operably linked to a cytomegalovirus (CMV) promoter comprising at least one tetracycline operator (TetO) motif. In certain embodiments, the Zika virus M and Env antigen comprises the amino acid sequence of SEQ ID NO:1. In certain embodiments, the CMV promoter comprising at least one TetO motif comprises a nucleotide sequence selected from the group consisting of SEQ ID NOs:3-5.

In certain embodiments, the adenoviral vector is selected from the group consisting of ChAd3, SAdV, rhAd51, rhAd52, rhAd53, hAd4, hAd5, hAd26, and hAd35. In certain embodiments, the adenoviral vector comprises a nucleotide sequence selected from the group consisting of SEQ ID NOs:9-11 and SEQ ID NO:15.

Also provided are host cells producing the adenoviral vector of the invention. In certain embodiments, the host cell further comprises a nucleotide sequence encoding a tetracycline repressor (TetR) protein. The nucleotide sequence encoding the TetR protein can, for example, be integrated in the genome of the host cell. The nucleotide sequence encoding the TetR protein can be integrated in chromosome 1. In certain embodiments, the host cell is a PER.C6® host cell.

Also provided are pharmaceutical compositions comprising an adenoviral vector of the invention and a pharmaceutically acceptable carrier.

Also provided are methods of producing an adenoviral particle comprising a Zika virus M and Env antigen. The methods comprise (a) contacting a host cell of the invention with an adenoviral vector of the invention; and (b) growing the host cell under conditions wherein the adenoviral particle of the invention is produced.

Also provided are pharmaceutical compositions comprising an adenoviral particle of the invention and a pharmaceutically acceptable carrier.

Also provided are methods for preventing a Zika virus infection or the progression of a Zika virus invention in a human subject in need thereof, the methods comprising administering to the subject the pharmaceutical compositions of the invention. The pharmaceutical compositions of the invention can, for example, be administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion, by catheter, by lavage, or by gavage.

Also provided are kits comprising (a) an adenoviral vector of the invention; and (b) a host cell of the invention.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

DETAILED DESCRIPTION OF THE INVENTION

Figure 1:
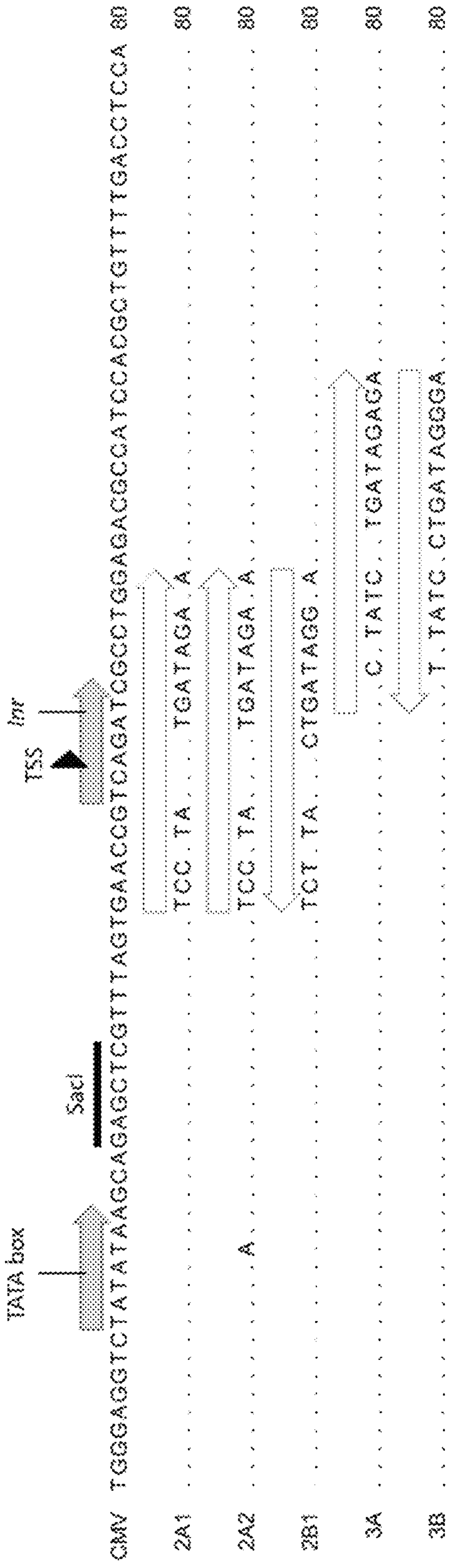
FIG. 1 shows a nucleotide sequence comparison of positions −40 to +40 of the human Cytomegalovirus promoter (CMV) with the corresponding positions of the 1× tetO-bearing CMV promoters described herein (2A1, 2A2, 2B1, 3A, and 3B). For each of these 1× tetO-bearing promoters only the nucleotides that differ from CMV are shown; nucleotides matching with those of CMV are shown as dots. Per 1× tetO-bearing promoter, the open arrow indicates location and orientation of the single tetO sequence (TCCCTATCAGTGATAGAGA) (SEQ ID NO:20). Inr, initiator element; TSS, transcription start site (i.e. position +1); SacI, location of the 54 bp-long, "2× tetO"-bearing sequence insertion present in CMVtetO v1.

This disclosure is based upon, at least in part, the identification of an adenoviral vector comprising a nucleotide sequence encoding a Zika virus M and Env antigens operably linked to a nucleotide sequence comprising a cytomegalovirus (CMV) promoter comprising at least one tetracycline operator (TetO) motifs, which allows for the cost-effective, large-scale manufacturing of adenoviral particles comprising the Zika virus M and Env antigens. Without intending to be limited by theory, it is believed that the expression of the Zika virus M and Env antigens leads to low levels of adenoviral particle production. The addition of the TetO motif to the CMV promoter allowed for higher levels of adenoviral particle production.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" or "patient" means any animal, preferably a mammal, most preferably a human, to whom will be or has been administered a pharmaceutical composition and/or vaccine comprising an adenoviral vector/adenoviral particle of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

As used herein, "a method of providing safe administration" means a method of administration that is effective in generating an immune response against a Zika virus without causing unacceptable adverse events, when administered to a subject.

As used herein, the phrases "unacceptable adverse events" and "unacceptable adverse reaction" shall mean all harm or undesired outcomes associated with or caused by administration of a pharmaceutical composition or therapeutic, and the harm or undesired outcome reaches such a level of severity that a regulatory agency deems the pharmaceutical composition or therapeutic unacceptable for the proposed use. Examples of unacceptable adverse events or reactions when used in the context of administration of adenoviral particles comprising a nucleic acid molecule encoding a Zika virus antigen can include, but is not limited to, swelling, injection side pain, headache, malaise, muscle ache, nausea, and fever.

In certain embodiments, "safe treatment" and "safe administration" when used with respect to administration of adenoviral vectors comprising a nucleic acid molecule encoding a Zika virus antigen means reduced adverse events including, but not limited to, swelling, injection side pain, headache, malaise, muscle ache, nausea, and fever.

The words "right", "left", "lower" and "upper" designate directions in the drawings to which reference is made.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., adenoviral vectors, Zika virus M and Env polypeptide and nucleotide sequences that encode the M and Env polypeptides, cytomegalovirus promotor nucleotide sequences, and tetracycline operator (TetO) sequences), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1997) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the term "immune response" or "protective immune response" means that the vaccinated subject is able to control an infection (e.g., a Zika virus (ZIKV) infection) with the pathogenic agent against which the vaccination was done (e.g., a ZIKV M and Env antigen). The pathogenic agent can, for example, be an antigenic gene product or antigenic protein, or a fragment thereof. Usually, the subject having developed an "immune response" or a "protective immune response" develops only mild to moderate clinical symptoms or no symptoms at all. Usually, a subject in which an "immune response" or "protective immune response" against a Zika virus has been generated, will not develop disease manifestations or those disease manifestations will be milder, and ultimately the subject will not die as a result of the infection with said virus. In addition, a subject in which an "immune response" or "protective immune response" against a Zika virus has been generated, will have a reduced chance of brain abnormalities in her infants exposed to the virus in utero.

By "generating an immune response" or "promoting an immune response" or "provoking an immune response" is meant eliciting a humoral response (e.g., the production of antibodies) or a cellular response (e.g., the activation of T cells, macrophages, neutrophils, and/or natural killer cells) directed against, for example, one or more infective agents (e.g., a virus (e.g., a ZIKV)) or protein targets in a subject to which the pharmaceutical composition (e.g., an immunogenic composition or vaccine) has been administered.

By "immunogen" or "antigen" is meant any polypeptide that can induce an immune response in a subject upon administration. In some embodiments, the immunogen or antigen is encoded by a nucleic acid molecule that may be incorporated into, for example, an adenoviral vector of the invention, for subsequent expression of the immunogen or antigen (e.g., a gene product of interest, or fragment thereof (e.g., a polypeptide)). In some embodiments, the antigen is derived from a ZIKV (e.g., a ZIKV from the Asian and/or African lineage (e.g., ZIKV strain BeH815744 (accession number KU365780)). In some embodiments, the antigen is administered in the context of a nucleic acid molecule expressing a polypeptide that is derived from a ZIKV (e.g., the ZIKV M and Env antigens from a ZIKV from the Asian and/or African lineage (e.g., ZIKV strain BeH815744 (accession number KU365780)).

The term "immunogenic composition" or "pharmaceutical composition" as used herein, is defined as material used to generate an immune response and may confer immunity after administration of the immunogenic composition to a subject.

By "isolated" is meant separated, recovered, or purified from a component of its natural environment. For example, a nucleic acid molecule or polypeptide of the invention may be isolated from a component of its natural environment by 1% (2%, 3%, 4%, 5%, 6%, 7%, 8% 9% 10%, 20%, 30%, 40%, 50%, 60% 70%, 80%, or 90%) or more.

Adenoviruses, Nucleic Acid Molecules, and Polypeptides of the Invention

In WO2017/214596, entitled "Compositions and Methods for Preventing and Treating Zika Virus Infection," disclosed are Zika virus (ZIKV) polypeptides that can be used to elicit protective immune responses against a ZIKV infection when administered to a subject (e.g., a mouse or monkey) infected with or likely to be exposed to a ZIKV infection. The ZIKV polypeptides for use in pharmaceutical compositions prepared for administration can include a M-Env, prM-Env, prM-Env.dTM, prM-Env.dStem, Env, Env.dTM, and/or Env.dStem or a portion thereof. Alternatively, the ZIKV polypeptides can be encoded for by a nucleic acid molecule comprised within a vector (e.g., an adenoviral vector).

Provided herein are adenoviral vectors comprising a nucleotide sequence encoding a Zika virus M and Env antigens. The nucleotide sequences encoding the Zika virus M and Env antigens can, for example, be operably linked to a cytomegalovirus (CMV) promoter comprising at least one tetracycline operator (TetO) motif. In certain embodiments, the CMV promoter comprises one, two, three, four, or five TetO motifs. The CMV promoter can, for example, be selected from the group consisting of SEQ ID NOs:3-5, which are provided below in Table 1.

TABLE 1

TetO-containing CMV promoters that can be used to control the expression of Zika virus M and Env antigens in an adenoviral vector.

| Promoter | SEQ ID NO: |
|---|---|
| 2A1 | 3 |
| 2A2 | 4 |
| 2B1 | 5 |

In certain embodiments, the Zika virus M and Env antigens comprise the amino acid sequence of SEQ ID NO:1.

The nucleotide sequence encoding the Zika virus M and Env antigens comprises SEQ ID NO:2.

The nucleic acid molecules have a nucleotide sequence with at least 85% (e.g., at least 86%, 87%, 88%, 89%, 90%, 91%, 92%, 93%, 94%, 95%, 96%, 97%, 98%, 99%, or 100%) sequence identity to, all or a portion of any one of SEQ ID NOs:2, 3, 4, 5, 6, 7, 8, 9, 10, 11, 12, 13, 14, or 15 or a complementary sequence thereof. Alternatively, an isolated nucleic acid molecule has a nucleotide sequence that encodes a ZIKV M and Env antigen with at least 85% (e.g., at least 86%, 87%, 88%, 89%, 90%, 91%, 92%, 93%, 94%, 95%, 96%, 97%, 98%, 99%, or 100%) sequence identity to, all or a portion of SEQ ID NO:1.

The nucleic acid molecules of the invention may be further optimized, such as by codon optimization, for expression in a targeted mammalian subject (e.g., human).

The nucleic acid molecules may also be inserted into expression vectors, such as an adenovirus vector and incorporated into compositions of the invention. The terms "adenovirus vector" and "adenoviral vector" and "adenoviral particles" are used interchangeably and refer to a genetically-engineered adenovirus that is designed to insert a polynucleotide of interest (e.g., a polynucleotide encoding the ZIKV M and Env antigen) into a eukaryotic cell, such that the polynucleotide is subsequently expressed. Examples of adenoviruses that can be used as a viral vector of the invention include those having, or derived from, the serotypes Ad2, Ad 4, Ad5, Ad11, Ad12, Ad24, Ad26, Ad34, Ad35, Ad40, Ad48, Ad49, Ad50, Ad52 (e.g., RhAd52), and Pan9 (also known as AdC68); these vectors can be derived from, for example, human, chimpanzee (e.g., ChAd1, ChAd3, ChAd7, ChAd8, ChAd21, ChAd22, ChAd23, ChAd24, ChAd25, ChAd26, ChAd27.1, ChAd28.1, ChAd29, ChAd30, ChAd31.1, ChAd32, ChAd33, ChAd34, ChAd35.1, ChAd36, ChAd37.2, ChAd39, ChAd40.1, ChAd41.1, ChAd42.1, ChAd43, ChAd44, ChAd45, ChAd46, ChAd48, ChAd49, ChAd49, ChAd50, ChAd67, or SA7P), or rhesus adenoviruses (e.g., rhAd51, rhAd52, or rhAd53).

"Nucleic acid molecule" or "polynucleotide," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after synthesis, such as by conjugation with a label.

By "heterologous nucleic acid molecule" is meant a nucleotide sequence that can encode proteins derived or obtained from pathogenic organisms, such as viruses, which can be incorporated into a polynucleotide or vector of the invention. Heterologous nucleic acids can also encode synthetic or artificial proteins, such as immunogenic epitopes, constructed to induce immunity. An example of a heterologous nucleic acid molecule is one that encodes one or more immunogenic peptides or polypeptides derived from a Zika virus (e.g., the ZIKV M and Env antigen). The heterologous nucleic acid molecule is one that is not normally associated with the other nucleic acid molecules found in the polynucleotide or vector into which the heterologous nucleic acid molecule is incorporated.

A "nucleic acid vaccine" or "DNA vaccine" refers to a vaccine that includes a heterologous nucleic acid molecule under the control of a promoter for expression in a subject. The heterologous nucleic acid molecule can be incorporated into an expression vector, such as an adenoviral vector.

The term "vaccine" as used herein, is defined as material used to provoke an immune response and that confers immunity for a period of time after administration of the vaccine to a subject.

A "promoter" is a nucleic acid sequence enabling the initiation of the transcription of a gene sequence in a messenger RNA, such transcription being initiated with the binding of an RNA polymerase on or nearby the promoter.

As provided herein, in certain embodiments, the promoter is a cytomegalovirus promoter comprising at least one tetracycline operator (TetO) motif. The TetO motif can be referred to a "regulatory sequence" or "regulatory element," which as used herein refers to a segment of nucleic acid, typically, but not limited to DNA, that modulates the transcription of the nucleic acid sequence to which it is operatively linked, and, thus, acts as a transcriptional modulator. A regulatory sequence often comprises nucleic acid sequences that are transcription binding domains that are recognized by the nucleic acid-binding domains of transcriptional proteins and/or transcription factors, enhancers, or repressors, etc. For example, it is possible to operably couple a repressor sequence to the promoter, which repressor sequence can be bound by a repressor protein that can decrease or prevent the expression of the transgene in a production cell line that expresses the repressor protein. This can improve genetic stability and/or expression levels of the nucleic acid molecule upon passaging and/or when this is produced at high quantities in the production cell line. Such systems have been described in the art. A regulatory sequence can include one or more tetracycline operator (TetO) motifs/sequences, such that expression is inhibited in the presence of the tetracycline repressor protein (TetR). In the absence of tetracycline, the TetR protein is able to bind to the TetO sites and repress transcription of a transgene (e.g., the ZIKV M and Env antigen) operably linked to the TetO motifs/sequences. In the presence of tetracycline, however, a conformational change in the TetR protein prevents it from binding to the TetO sequences, allowing transcription of operably linked transgenes to occur. In certain embodiments, the nucleic acid encoding the ZIKV M and Env antigen, when present in the adenoviral vector, is operably linked to a cytomegalovirus (CMV) promoter comprising at least one tetracycline operator (TetO) motif, such that the expression of the ZIKV M and Env antigen is inhibited in recombinant adenoviruses that are produced in the producer cell line in which the TetR protein is expressed. Subsequently, expression would not be inhibited in the recombinant adenoviral vector is introduced into a subject or into cells that do not express the TetR protein.

As used herein, the term "repressor" refers to molecules (e.g., proteins) having the capability to inhibit, interfere, retard, and/or repress the production of a heterologous protein product of a recombinant expression vector (e.g., an adenoviral vector). The repressor can inhibit expression by interfering with a binding site at an appropriate location along the expression vector, such as in an expression cassette (e.g., a TetR can bind the TetO motif in the CMV promoter). Repression of vector transgene expression during vector propagation can prevent transgene instability and can increase yields of vectors having the transgene during production.

A nucleic acid is "operably linked" when it is placed into a structural or functional relationship with another nucleic acid sequence. For example, one segment of DNA can be operably linked to another segment of DNA if they are positioned relative to one another on the same contiguous DNA molecule and have a structural or functional relationship, such as a promoter or enhancer that is positioned relative to a coding sequence so as to facilitate transcription of the coding sequence; a ribosome binding site that is positioned relative to a coding sequence so as to facilitate translation; or a pre-sequence or secretory leader that is positioned relative to a coding sequence so as to facilitate expression of a pre-protein (e.g., a pre-protein that participates in the secretion of the encoded polypeptide). In other examples, the operably linked nucleic acid sequences are not contiguous, but are positioned in such a way that they have a functional relationship with each other as nucleic acids or as proteins that are expressed by them. Enhancers, for example, do not have to be contiguous. Linking may be accomplished by ligation at convenient restriction sites or by using synthetic oligonucleotide adaptors or linkers.

An adenovirus according to the invention belongs to the family of the Adenoviridae and preferably is one that belongs to the genus *Mastadenovirus*. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu; in the invention a human adenovirus is meant if referred to Ad without indication of species, e.g. the brief notation "Ad5" means the same as HAdV5, which is human adenovirus serotype 5), or a simian adenovirus such as chimpanzee or gorilla adenovirus (ChAd, AdCh, or SAdV).

Most advanced studies have been performed using human adenoviruses, and human adenoviruses are preferred according to certain aspects of the invention. In certain preferred embodiments, the recombinant adenovirus according to the invention is based upon a human adenovirus. In preferred embodiments, the recombinant adenovirus is based upon a human adenovirus serotype 4, 5, 11, 26, 34, 35, 48, 49 or 50. According to a particularly preferred embodiment of the invention, an adenovirus is a human adenovirus of one of the serotypes 26 or 35.

An advantage of these serotypes is a low seroprevalence and/or low pre-existing neutralizing antibody titers in the human population. Preparation of rAd26 vectors is described, for example, in WO 2007/104792 and in Abbink et al., (2007) Virol 81(9):4654-63, both of which are incorporated by reference herein in their entirety. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811, in WO 00/70071, and in Vogels et al., (2003) J Virol 77(15): 8263-71, all of which are incorporated by reference herein in their entirety. Exemplary genome sequences of Ad35 are found in GenBank Accession AC_000019 and in FIG. 6 of WO 00/70071.

Simian adenoviruses generally also have a low seroprevalence and/or low pre-existing neutralizing antibody titers in the human population, and a significant amount of work has been reported using chimpanzee adenovirus vectors (e.g. U.S. Pat. No. 6,083,716; WO 2005/071093; WO 2010/086189; WO 2010085984; Farina et al, 2001, J Virol 75: 11603-13; Cohen et al, 2002, J Gen Virol 83: 151-55; Kobinger et al, 2006, Virology 346: 394-401; Tatsis et al., 2007, Molecular Therapy 15: 608-17; see also review by Bangari and Mittal, 2006, Vaccine 24: 849-62; and review by Lasaro and Ertl, 2009, Mol Ther 17: 1333-39). Hence, in other preferred embodiments, the recombinant adenovirus according to the invention is based upon a simian adenovirus, e.g. a chimpanzee adenovirus. In certain embodiments, the recombinant adenovirus is based upon simian adenovirus type 1, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P.

Adenoviral Vector rAd26

In a preferred embodiment according to the invention the adenoviral vectors comprise capsid proteins from two rare serotypes: Ad26 or Ad35. In the typical embodiment, the vector is an rAd26 virus.

One of skill will recognize that elements derived from multiple serotypes can be combined in a single recombinant adenovirus vector. Thus, a chimeric adenovirus that combines desirable properties from different serotypes can be produced. Thus, in some embodiments, a chimeric adenovirus of the invention could combine the absence of pre-existing immunity of the Ad26 serotypes with characteristics such as temperature stability, assembly, anchoring, production yield, redirected or improved infection, stability of the DNA in the target cell, and the like.

In certain embodiments the recombinant adenovirus vector useful in the invention is derived mainly or entirely from Ad26 (i.e., the vector is rAd26). In some embodiments, the adenovirus is replication deficient, e.g. because it contains a deletion in the E1 region of the genome. For the adenoviruses of the invention, being derived from Ad26, it is typical to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as for example HEK293 cells, PER.C6® cells, and the like (see, e.g. Havenga et al, 2006, J Gen Virol 87: 2135-43; WO 03/104467). In certain embodiments, the adenovirus is a human adenovirus of serotype 35, with a deletion in the E1 region into which the nucleic acid encoding the antigen has been cloned, and with an E4 orf6 region of Ad5. In certain embodiments, the adenovirus is a human adenovirus of serotype 26, with a deletion in the E1 region into which the nucleic acid encoding the antigen has been cloned, and with an E4 orf6 region of Ad5. For the Ad35 adenovirus, it is typical to retain the 3' end of the E1B 55K open reading frame in the adenovirus, for instance the 166 bp directly upstream of the pIX open reading frame or a fragment comprising this such as a 243 bp fragment directly upstream of the pIX start codon, marked at the 5' end by a Bsu36I restriction site, since this increases the stability of the adenovirus because the promoter of the pIX gene is partly residing in this area (see, e.g. Havenga et al, 2006, supra; WO 2004/001032). The preparation of recombinant adenoviral vectors is well known in the art.

Preparation of rAd26 vectors is described, for example, in WO 2007/104792 and in Abbink et al., (2007) Virol 81(9): 4654-63. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811 and in Vogels et al., (2003) J Virol 77(15): 8263-71. An exemplary genome sequence of Ad35 is found in GenBank Accession AC_000019.

In an embodiment of the invention, the vectors useful for the invention include those described in WO2012/082918, the disclosure of which is incorporated herein by reference in its entirety.

Typically, a vector useful in the invention is produced using a nucleic acid comprising the entire recombinant adenoviral genome (e.g., a plasmid, cosmid, or baculovirus vector). Thus, the invention also provides isolated nucleic acid molecules that encode the adenoviral vectors of the invention. The nucleic acid molecules of the invention can be in the form of RNA or in the form of DNA obtained by cloning or produced synthetically. The DNA can be double-stranded or single-stranded.

The adenovirus vectors useful in the invention are typically replication defective. In these embodiments, the virus is rendered replication-defective by deletion or inactivation of regions critical to replication of the virus, such as the E1 region. The regions can be substantially deleted or inactivated by, for example, inserting the gene of interest (usually linked to a promoter). In some embodiments, the vectors of the invention may contain deletions in other regions, such as the E2, E3 or E4 regions or insertions of heterologous genes linked to a promoter. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amount of adenovirus vectors of the invention. A packaging cell is a cell that comprises those genes that have been deleted or inactivated in a replication-defective vector, thus allowing the virus to replicate in the cell. Suitable cell lines include, for example, PER.C6®, 911, 293, and E1 A549.

In certain embodiments, the packaging cell line or host cell line further comprises a nucleotide sequence encoding a tetracycline repressor (TetR) protein. The nucleotide sequence encoding the TetR protein can, for example, be integrated in the genome of the packaging cell line or host cell line. By way of an example, the nucleotide sequence encoding the TetR protein can be integrated in chromosome 1. The packaging cell line/host cell line can, for example, be a PER.C6® packaging cell line/host cell line.

In certain embodiments, provided herein are methods of producing an adenoviral particle comprising a Zika virus M and Env antigen. The methods comprise (a) contacting a host cell of the invention with an adenoviral vector of the invention and (b) growing the host cell under conditions wherein the adenoviral particle comprising the Zika M and Env antigen is produced.

In certain embodiments, the adenoviral vector comprises a transgene. A "transgene" refers to a heterologous nucleic acid, which is a nucleic acid that is not naturally present in the vector, and according to the present invention the transgene can encode an antigenic gene product or antigenic protein (e.g., a ZIKV M and Env antigen) that elicits an immune response in the subject. The transgene can, for example, be introduced into the vector by standard molecular biology techniques. The transgene can, for example, be cloned into a deleted E1 or E3 region of an adenoviral vector, or in the region between the E4 region and the rITR. A transgene is generally operably linked to expression control sequences. In preferred embodiments, the transgene is inserted at a transgene insertion site.

Pharmaceutical Compositions

In another general aspect, the invention relates to pharmaceutical compositions comprising adenoviral vectors (or adenoviral particles) of the invention (i.e., adenoviral vectors or adenoviral particles comprising nucleic acid molecule encoding Zika virus M and Env antigens) and a pharmaceutically acceptable carrier. Adenoviral vectors (or particles) of the invention and compositions comprising them are also useful in the manufacture of a medicament for therapeutic applications mentioned herein.

By "pharmaceutical composition" is meant any composition that contains a therapeutically or biologically active agent, such as an immunogenic composition or vaccine of the invention (e.g., an adenoviral particle comprising a ZIKV nucleic acid molecule and/or polypeptide/antigen of the invention), preferably including a nucleotide sequence encoding an antigenic gene product of interest, or fragment thereof, that is suitable for administration to a subject and that treats or prevents a disease (e.g., ZIKV infection) or reduces or ameliorates one or more symptoms of the disease (e.g., ZIKV viral titer, viral spread, infection, and/or cell fusion)). For the purposes of this invention, pharmaceutical compositions include vaccines, and pharmaceutical compositions suitable for delivering a therapeutic or biologically active agent can include, for example, tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of these formulations can be prepared by well-known and accepted methods of art. See, for example, *Remington: The Science and Practice of Pharmacy* ($21^{st}$ ed.), ed. A. R. Gennaro, Lippincott Williams & Wilkins, 2005, and *Encyclopedia of Pharmaceutical Technology*, ed. J. Swarbrick, Informa Healthcare, 2006, each of which is hereby incorporated by reference.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in a pharmaceutical composition can be used in the invention.

Pharmaceutically acceptable acidic/anionic salts for use in the invention include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, chloroprocaine, choline, cyclohexylamine, diethanolamine, ethylenediamine, lithium, L-lysine, magnesium, meglumine, N-methyl-D-glucamine, piperidine, potassium, procaine, quinine, sodium, triethanolamine, or zinc.

In some embodiments of the invention, pharmaceutical compositions are provided comprising the adenoviral particles of the invention in an amount from about $1\times10^{10}$, about $2\times10^{10}$, about $3\times10^{10}$, about $4\times10^{10}$, about $5\times10^{10}$, about $6\times10^{10}$, about $7\times10^{10}$, about $8\times10^{10}$, about $9\times10^{10}$, about $1\times10^{11}$, about $2\times10^{11}$, about $3\times10^{11}$, about $4\times10^{11}$, or about $5\times10^{11}$ viral particles per dose. In certain embodiments of the invention, the pharmaceutical composition comprises about $1\times10^{10}$ adenoviral particles to about $5\times10^{11}$ adenoviral particles per dose. In certain embodiments of the invention, the pharmaceutical composition comprises about $1\times10^{10}$ adenoviral particles to about $1\times10^{12}$ adenoviral particles per dose. In certain embodiments of the invention, the pharmaceutical composition comprises about $5\times10^{10}$ adenoviral particles to about $1\times10^{11}$ adenoviral particles per dose. In certain embodiments of the invention, the pharmaceutical composition comprises about $5\times10^{10}$ adenoviral particles per dose. In certain embodiments of the invention, the pharmaceutical composition comprises about $1\times10^{11}$ adenoviral particles per dose.

The pharmaceutical composition can have a pH from about 3.0 to about 10, for example from about 3 to about 7, or from about 5 to about 9. The formulation can further comprise at least one ingredient selected from the group consisting of a buffer system, preservative(s), tonicity agent(s), chelating agent(s), stabilizer(s) and surfactant(s).

In certain embodiments, the subject is administered a single dose of the pharmaceutical composition. In certain embodiments, the subject is administered a double dose of the pharmaceutical composition. When administering a double dose, the first and second dose of the pharmaceutical composition can be administered to the subject about four weeks, about eight weeks, about twelve weeks, about three months, about six months, about nine months, about one year, about two years, about three years, about four years, about five years, or about ten years apart.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carriers can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via a syringe or an infusion pump. The injection can be delivered subcutaneously, intramuscularly, intraperitoneally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/mL to about 50 mg/mL, for example from about 0.1 mg/mL to about 20 mg/mL. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/mL to about 50 mg/mL, for example from about 0.1 mg/mL to about 20 mg/mL. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars can be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/mL to about 50 mg/mL, for example from about 0.1 mg/mL to about 20 mg/mL. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/mL to about 50 mg/mL, for example from about 0.1 mg/mL to about 20 mg/mL. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivatives thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/mL to about 50 mg/mL, for example from about 0.1 mg/mL to about 20 mg/mL. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/mL to about 20 mg/mL. Pharmaceutical compositions comprising each one of these specific surfactants constitute alternative embodiments of the invention.

In a further embodiment of the invention, the pharmaceutical composition comprises one or more protease inhibitors, such as, e.g., EDTA (ethylenediamine tetraacetic acid), and/or benzamidine hydrochloric acid (HCl). The protease inhibitor can be present individually or in the aggregate, in a concentration from about 0.1 mg/mL to about 20 mg/mL. Pharmaceutical compositions comprising each one of these specific protease inhibitors constitute alternative embodiments of the invention.

The pharmaceutical composition of the invention can comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid can be present either in its free base form or in its salt form. Any stereoisomer (i.e., L, D, or a mixture thereof) of the amino acid base can be present. The amino acid base can be present individually or in the combination with other amino acid bases, in a concentration from about 0.01 mg/mL to about 50 mg/mL, for example from about 0.1 mg/mL to about 20 mg/mL. Pharmaceutical compositions comprising each one of these specific amino acid bases constitute alternative embodiments of the invention.

It is also apparent to one skilled in the art that the therapeutically effective dose for adenoviral particles comprising a nucleic acid molecule encoding a Zika virus M and Env antigen of the present invention or a pharmaceutical composition thereof will vary according to the desired effect. Therefore, optimal dosages to be administered can be readily determined by one skilled in the art and will vary with the particular adenoviral particle used, the mode of administration, the strength of the preparation, and the advancement of the disease condition (e.g., Zika virus infection). In addition, factors associated with the particular subject being treated, including subject age, weight, diet and time of administration, will result in the need to adjust the dose to an appropriate therapeutic level.

The pharmaceutically-acceptable salts of the adenoviral particles of the invention include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups can be quaternized with, for example, alkyl halides.

The pharmaceutical compositions of the invention can be administered by any means that accomplish their intended purpose. As used herein, by "administering" is meant a method of giving a dosage of a pharmaceutical composition (e.g., an immunogenic composition (e.g., a vaccine (e.g., a Zika virus (ZIKV) vaccine))) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions. The preferred method of administration can vary depending on various factors (e.g., the components of the composition being administered and the severity of the condition being treated).

Methods of Use

The present invention provides methods for generating an immune response against a Zika virus in a human subject in need thereof. The methods comprise administering to the subject a pharmaceutical composition comprising adenoviral vectors comprising a nucleic acid sequence encoding a Zika virus M and Env antigen and a pharmaceutically acceptable carrier. The methods are for preventing, treating, delaying the onset of, or ameliorating a Zika virus infection or any one or more symptoms of said Zika virus infection, the method comprising administering to the subject in need thereof an effective amount of a pharmaceutical composition of the invention.

According to particular embodiments, an immunogenic or effective or protective amount refers to the amount of an immunogen which is sufficient to achieve one, two, three, four, or more of the following effects: (i) reduce or ameliorate the severity of the Zika virus infection to be treated or a symptom associated therewith; (ii) reduce the duration of the Zika virus infection to be treated, or a symptom associated therewith; (iii) prevent the progression of the Zika virus infection to be treated, or a symptom associated therewith; (iv) cause regression of the Zika virus infection to be treated, or a symptom associated therewith; (v) prevent the development or onset of the Zika virus infection to be treated, or a symptom associated therewith; (vi) prevent the recurrence of the Zika virus infection to be treated, or a symptom associated therewith; (vii) reduce hospitalization of a subject having the Zika virus infection or condition to be treated, or a symptom associated therewith; (viii) reduce hospitalization length of a subject having the Zika virus infection to be treated, or a symptom associated therewith; (ix) increase the survival of a subject with the Zika virus infection to be treated, or a symptom associated therewith; (xi) inhibit or reduce the Zika virus infection to be treated, or a symptom associated therewith in a subject; and/or (xii) enhance or improve the prophylactic or therapeutic effect(s) of another therapy; (xiii) prevent transmission of Zika virus through sexual and maternal to fetal routes; (xiv) prevent and/or reduces the severity of fetal brain abnormalities associated with Zika virus.

Examples of symptoms of diseases caused by a viral infection, such as ZIKV, that can be prevented using the compositions of the invention include, for example, fever, joint pain, rash, conjunctivitis, muscle pain, headache, retro-orbital pain, edema, lymphadenopathy, malaise, asthenia, sore throat, cough, nausea, vomiting, diarrhea, and hematospermia. These symptoms, and their resolution during treatment, can be measured by, for example, a physician during a physical examination or by other tests and methods known in the art.

The immunogenic or effective amount or dosage can vary according to various factors, such as the Zika virus infection to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

As used herein, the terms "treat," "treating," and "treatment" are all intended to refer to an amelioration or reversal of at least one measurable physical parameter related to the Zika virus infection, which is not necessarily discernible in the subject, but can be discernible in the subject. The terms "treat," "treating," and "treatment," can also refer to causing regression, preventing the progression, or at least slowing down the progression of the Zika virus infection. In a particular embodiment, "treat," "treating," and "treatment" refer to an alleviation, prevention of the development or onset, or reduction in the duration of one or more symptoms associated with the Zika virus infection. In a particular embodiment, "treat," "treating," and "treatment" refer to prevention of the recurrence of the Zika virus infection. In a particular embodiment, "treat," "treating," and "treatment" refer to an increase in the survival of a subject having the Zika virus infection. In a particular embodiment, "treat," "treating," and "treatment" refer to elimination of the Zika virus infection in the subject.

In certain embodiments, administration of an immunogenic or effective amount of a pharmaceutical composition of the invention reduces ZIKV serum viral loads determined from a subject having a ZIKV infection by at least about 5%, 10%, 20%, 30%, 40%, 50%, 60%, 70%, 80%, 90%, or more compared to viral loads determined from the subject prior to administration of an effective amount of a composition of the invention. In some instances, administration of an effective amount of a composition of the invention reduces serum viral loads to an undetectable level compared to viral loads determined from the subject prior to administration of an effective amount of a composition of the invention. In some instances, administration of an effective amount of a composition of the invention results in a reduced and/or undetectable serum viral load that can be maintained for at least about 1, 2, 3, 4, 5, 6, 7 days; 1, 2, 3, 4, weeks; 1, 2, 3, 4, 5, 6, 7, 8, 9, 10, 11, or 12 months; or 1 year or more.

In addition, single or multiple administrations of the compositions of the present invention can be given (pre- or post-exposure and/or pre- or post-diagnosis) to a subject (e.g., one administration or administration two or more times). For example, subjects who are particularly susceptible to, for example, viral infection (e.g., a ZIKV infection) can require multiple administrations of the compositions of the present invention to establish and/or maintain protection against the virus. Levels of induced immunity provided by the pharmaceutical compositions described herein can be monitored by, for example, measuring amounts of neutralizing secretory and serum antibodies. The dosages can then be adjusted or repeated as necessary to trigger the desired level of immune response. For example, the immune response triggered by a single administration (prime) of a composition of the invention may not be sufficiently potent and/or persistent to provide effective protection. Accordingly, in some embodiments, repeated administration (boost), such that a prime boost regimen is established, can significantly enhance humoral and cellular responses to the antigen of the composition.

Alternatively, the efficacy of treatment can be determined by monitoring the level of the antigenic or therapeutic gene product, or fragment thereof, expressed in a subject (e.g., a human) following administration of the pharmaceutical compositions of the invention. For example, the blood or lymph of a subject can be tested for antigenic or therapeutic gene product, or fragment thereof, using, for example, standard assays known in the art.

In some instances, efficacy of treatment can be determined by monitoring a change in the serum viral load from a sample from the subject obtained prior to and after administration of an effective amount of a pharmaceutical composition of the invention. A reduction in serum viral load of at least about 5%, 10%, 20%, 30%, 40%, 50%, 60%, 70%, 80%, 90%, or more compared to viral load determined from the subject prior to administration of an effective amount of a composition of the invention can indicate that the subject is receiving benefit from the treatment. If a viral load does not decrease by at least about 10%, 20%, 30%, or more after administration of a composition of the invention, the dosage of the composition to be administered can be increased. For example, by increasing the number of viral particles (VP) of an adenovirus vector-based vaccine.

Immunogenicity of the pharmaceutical compositions of the invention can be improved if it is co-administered with an immunostimulatory agent and/or adjuvant. Suitable adjuvants well-known to those skilled in the art include, for example, aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, and other adjuvants and derivatives thereof.

The term "immunostimulatory agent" refers to substances (e.g., drugs and nutrients) that stimulate the immune system by inducing activation or increasing activity of any of its components. An immunostimulatory agent includes a cytokine (e.g., the granulocyte macrophage colony-stimulating factor) and interferon (e.g., IFN-α and/or IFN-γ).

The term "adjuvant" is defined as a pharmacological or immunological agent that modifies the effect of other agents (e.g., a ZIKV antigen) while having few if any direct effects when administered alone. An adjuvant can be one or more substances that cause stimulation of the immune system. In this context, an adjuvant is used to enhance an immune response to the adenoviral particles of the invention.

Kits

Also provided herein are kits comprising (a) an adenoviral vector of the invention and (b) a host cell of the invention. In certain embodiments, the adenoviral vector comprises a nucleotide sequence encoding a Zika virus M and Env antigen, wherein the nucleotide sequence encoding the Zika virus M and Env antigen is operably linked to a cytomegalovirus (CMV) promoter comprising at least one tetracycline operator (TetO) motif. The adenoviral vector can comprise a nucleotide sequence selected from the group consisting of SEQ ID NOs:9-11 and SEQ ID NO:15.

In certain embodiments, the host cell comprises a nucleotide sequence encoding a tetracycline repressor (TetR) protein. The nucleotide sequence encoding the TetR protein can, for example, be integrated in the genome of the host cell. The nucleotide sequence encoding the TetR protein can be integrated in chromosome 1. In certain embodiments the host cell is a PER.C6® host cell.

EMBODIMENTS

The invention provides also the following non-limiting embodiments.

Embodiment 1 is an adenoviral vector comprising a nucleotide sequence encoding a Zika virus M and Env antigen, wherein the nucleotide sequence encoding the Zika virus M and Env antigen is operably linked to a cytomegalovirus (CMV) promoter comprising at least one tetracycline operator (TetO) motif.

Embodiment 2 is the adenoviral vector of embodiment 1, wherein the Zika virus M and Env antigen comprises the amino acid sequence of SEQ ID NO:1.

Embodiment 3 is the adenoviral vector of embodiment 1 or 2, wherein the CMV promoter comprising at least one TetO motif comprises a nucleotide sequence selected from the group consisting of SEQ ID NOs:3-5.

Embodiment 4 is the adenoviral vector of any one of embodiments 1 to 3, wherein the adenoviral vector is selected from the group consisting of ChAd3, SAdV, rhAd51, rhAd52, rhAd53, hAd4, hAd5, hAd26, and hAd35.

Embodiment 5 is the adenoviral vector of embodiment 4, wherein the adenoviral vector is Ad26.

Embodiment 6 is the adenoviral vector of any one of embodiments 1 to 5, wherein the adenoviral vector comprises a nucleotide sequence selected from the group consisting of SEQ ID NOs:9-11 and SEQ ID NO:15.

Embodiment 7 is a host cell comprising the adenoviral vector of any one of embodiments 1 to 6.

Embodiment 8 is the host cell of embodiment 7, wherein the host cell further comprises a nucleotide sequence encoding a tetracycline repressor (TetR) protein.

Embodiment 9 is the host cell of embodiment 8, wherein the nucleotide sequence encoding the TetR protein is integrated in the genome of the host cell.

Embodiment 10 is the host cell of embodiment 9, wherein the nucleotide sequence encoding the TetR protein is integrated in chromosome 1.

Embodiment 11 is the host cell of any one of embodiments 7 to 10, wherein the host cell is a PER.C6® host cell.

Embodiment 12 is a pharmaceutical composition comprising the adenoviral vector of any one of embodiments 1 to 6 and a pharmaceutically acceptable carrier.

Embodiment 13 is a method of producing an adenoviral particle comprising a Zika virus M and Env antigen, wherein the method comprises:

a. contacting a host cell with an adenoviral vector comprising a nucleotide sequence encoding a Zika virus M and Env antigen, wherein the nucleotide sequence encoding the Zika virus M and Env antigen is operably linked to a cytomegalovirus (CMV) promoter comprising at least one tetracycline operator (TetO) motif; and
b. growing the host cell under conditions wherein the adenoviral particle comprising the Zika M and Env antigen is produced.

Embodiment 14 is the method of embodiment 13, wherein the Zika virus M and Env antigen comprises the amino acid sequence of SEQ ID NO:1.

Embodiment 15 is the method of embodiment 13 or 14, wherein the CMV promoter comprising at least one TetO motif comprises a nucleotide sequence selected from the group consisting of SEQ ID NOs:3-5.

Embodiment 16 is the method of any one of embodiments 13 to 15, wherein the adenoviral vector is selected from the group consisting of ChAd3, SAdV, rhAd51, rhAd52, rhAd53, hAd4, hAd5, hAd26, and hAd35.

Embodiment 17 is the method of embodiment 16, wherein the adenoviral vector is hAd26.

Embodiment 18 is the method of any one of embodiments 13 to 17, wherein the adenoviral vector comprises a nucleotide sequence selected from the group consisting of SEQ ID NOs:9-11 and SEQ ID NO:15.

Embodiment 19 is the method of embodiment 13, wherein the host cell further comprises a nucleotide sequence encoding a tetracycline repressor (TetR) protein.

Embodiment 20 is the method of embodiment 19, wherein the nucleotide sequence encoding the TetR protein is integrated in the genome of the host cell.

Embodiment 21 is the method of embodiment 20, wherein the nucleotide sequence encoding the TetR protein is integrated in chromosome 1.

Embodiment 22 is the method of any one of embodiments 19 to 21, wherein the host cell is a PER.C6® host cell.

Embodiment 23 is a pharmaceutical composition comprising an adenoviral particle produced by the method of any one of embodiments 13 to 22 and a pharmaceutically acceptable carrier.

Embodiment 24 is a method for preventing a Zika virus infection or the progression of a Zika virus infection in a human subject in need thereof, the method comprising administering to the subject in need thereof the pharmaceutical composition of embodiment 23.

Embodiment 25 is the method of embodiment 24, wherein the pharmaceutical composition is administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion, by catheter, by lavage, or by gavage.

Embodiment 26 is a kit comprising:

a. an adenoviral vector comprising a nucleotide sequence encoding a Zika virus M and Env antigen, wherein the nucleotide sequence encoding the Zika virus M and Env antigen is operably linked to a cytomegalovirus (CMV) promoter comprising at least one tetracycline operator (TetO) motif; and b. a host cell comprising a nucleotide sequence encoding a tetracycline repressor (TetR) protein.

Embodiment 27 is the kit of embodiment 26, wherein the Zika virus M and Env antigen comprises the amino acid sequence of SEQ ID NO:1.

Embodiment 28 is the kit of embodiment 26 or 27, wherein the CMV promoter comprising at least one TetO motif comprises a nucleotide sequence selected from the group consisting of SEQ ID NOs:3-5.

Embodiment 29 is the kit of any one of embodiments 26 to 28, wherein the adenoviral vector is selected from the group consisting of ChAd3, SAdV, rhAd51, rhAd52, rhAd53, hAd4, hAd5, hAd26, and hAd35.

Embodiment 30 is the kit of embodiment 29, wherein the adenoviral vector is hAd26.

Embodiment 31 is the kit of any one of embodiments 26 to 30, wherein the adenoviral vector comprises a nucleotide sequence selected from the group consisting of SEQ ID NOs:9-11 and SEQ ID NO:15.

Embodiment 32 is the kit of any one of embodiments 26 to 31, wherein the nucleotide sequence encoding the TetR protein is integrated in the genome of the host cell.

Embodiment 33 is the kit of embodiment 32, wherein the nucleotide sequence encoding the TetR protein is integrated in chromosome 1.

Embodiment 34 is the kit of any one of embodiments 26 to 33, wherein the host cell is a PER.C6® host cell

EXAMPLES

Example 1: Novel and Potent Single TetO Motif-Bearing CMV Promoter Variants that are Strongly Repressible by TetR An E1- and E3-deleted Ad26-based adenoviral vector comprising a nucleotide sequence encoding a Zika virus M and Env antigen, was generated according to methods described previously by Abbink et al. (J Virol. 2007 May; 81(9):4654-63). In this vector, designated herein as Ad26.ZIKV.001, expression of the Zika virus antigen is driven by the strong and constitutively active cytomegalovirus (CMV) promoter that was employed previously to drive the expression of antigens encoded by other adenovirus vaccine vectors (Abbink et al. J Virol. 2007 May; 81(9):4654-63). Unfortunately, while it was possible to generate Ad26.ZIKV.001 and produce batches for preclinical immunogenicity testing, it was found that this vector displayed compromised growth on E1-complementing producer cells like PER.C6® compared to other adenovirus vaccine vectors, yielding for example viral particle production titers that were about 10-fold lower than that of a good-producing benchmark Ad26-based vector.

To address the productivity issue seen for Ad26.ZIKV.001, a new version of this vector was generated in which the expression of the Zika virus antigen is controlled by a CMV promoter that is repressible by TetR. In producer cells expressing TetR, such a vector would express lower levels of the Zika virus antigen and can, consequently, exhibit improved productivity due to avoidance of any inhibitory effect that high-level Zika virus antigen expression can have on vector production. Preferably, a TetR-repressible CMV promoter to be used in a the new Zika virus antigen-encoding vector would carry only a minimal modification compared to the CMV promoter used in Ad26.ZIKV.001 such that overall properties and potency of the final vector would remain the same as Ad26.ZIKV.001. Therefore, to achieve this, a panel of new promoters were designed and constructed to be TetR-repressible due to the introduction of a single tetO sequence close to the CMV promoter transcription start site. These promoters were subsequently tested for TetR-repressibility and promoter strength, comparing them to the known TetR-repressible promoter "CMVtetO" (SEQ ID NO:8), which is also referred herein as CMVtetO version 1 (CMVtetO v1). This promoter is derived from the human CMV promoter but is modified to carry, just downstream of its TATA box, a 54-bp sequence insertion comprising two copies of the 19-bp TetO motif (TCCCTATCAGTGATAGAGA) (SEQ ID NO:20).

A panel of CMV promoter variants that were designed to be TetR-repressible by modifications in the CMV promoter core region were tested and several of these were found to be TetR-repressible. FIG. 1 shows the design of the promoter core region of the TetR-repressible CMV promoter variants 2A1, 2A2, 2B1, 3A, and 3B. These variants differ from the parental CMV promoter by the substitutions displayed in FIG. 1. Each of these variants carries a single TetO sequence that was introduced by a set of substitutions that retained the native relative positioning between conserved CMV promoter elements like for instance the TATA box and the initiator element (Inr). In variants 2A1, 2A2, and 2B1, this single TetO sequence was introduced by substitution of nucleotide residues surrounding the native transcription start site (TSS), while in variants 3A and 3B, this was done by substitution of residues downstream of said TSS. The Inr motif, with consensus sequence YYANWYY, was left partially (2A1, 2A2, 2B1) or fully (3A, 3B) intact. The length of these single TetO-bearing CMV promoters remained the same as that of the parental, non-TetO-bearing CMV promoter present in Ad26.ZIK.001. The complete sequences of the TetO-bearing CMV promoter variants 2A1, 2A2, 2B1, 3A, and 3B are set forth in, respectively SEQ ID NOs:3-7.

If to be used to drive transgene (TG) expression in an Ad vaccine vector, then it is considered advantageous that achieved TG expression levels (potency) is not compromised compared to the standard, non-tetO-bearing CMV promoter that have previously been extensively used and tested in the context of Adenoviral vectors to drive antigen expression, and that is present in Ad26.ZIK.001. Furthermore, it is important that TetR-repressibility of the new TetO-bearing CMV promoters is sufficiently high in order to avoid any inhibitory effects of the antigen on vector production in TetR expressing producer cells.

Figure 2:
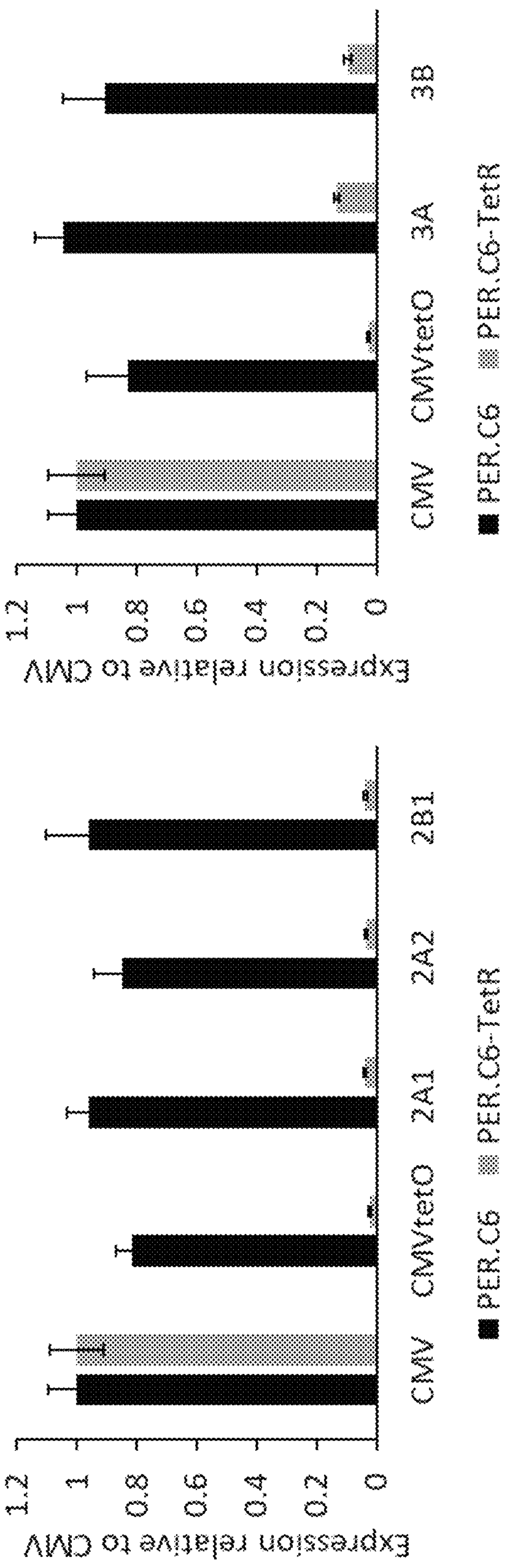
FIG. 2 shows graphs demonstrating the expression, relative to CMV, of the 1× tetO-bearing CMV promoters 2A1, 2A2, 2B1, 3A, and 3B as well as that of the 2× tetO-bearing promoter CMVtetO v1 (CMVtetO) in sPER.C6® cells and sPER.C6®-TetR cells.

Therefore, to investigate whether the new TetO promoters might have utility as antigen expression-driving promoters in Ad vaccine vectors, they were subjected to promoter potency and TetR-repressibility testing using a transient transfection-based dual reporter assay. Briefly, the promoter sequences were synthesized (by GeneArt) and introduced by standard molecular techniques into pDualLuc, described previously in PCT/EP2018/053201, to drive the expression of Gaussia luciferase (GL). Next to the Gaussia Luciferase cassette this plasmid carries a red firefly Luciferase (RFL)-expression cassette to be used for Gaussia Luciferase signal normalization. To test the new promoters, PER.C6® cells and the TetR-expressing cell line PER.C6-hCMV.TetR (described previously in PCT/EP2018/053201) were transfected with the new reporter constructs or with control constructs in which GL is controlled by CMV or CMVtetO v1. GLuc and red firefly Luciferase (RFL) activities were subsequently determined as described previously in PCT/EP2018/053201. For each of the tested promoter variants, FIG. 2 shows the level of (RFL-normalized) GLuc expression obtained relative to that obtained by CMV, in both PER.C6® and PER.C6®-hCMV.TetR cells. The data show that in PER.C6® all five single tetO-bearing promoters exhibited expression levels close to that of the standard CMV, with promoters 2A1, 2B1, and 3A giving the highest values. These three variants showed slightly higher expression levels than the original CMVtetO promoter (CMVtetO v1), which has consistently displayed slightly lower expression levels than CMV (in FIG. 2 and data not shown). In the TetR-expressing cells, expression levels obtained by all five new TetO-containing promoters is reduced, with the level of reduction seen for 2A1, 2A2, and 2B1 being close to what is seen for the 2× TetO-bearing promoter CMVtetO version 1, indicating potent TetR-repressibility. By contrast, variants 3A and 3B displayed a markedly lower level of TetR-repressibility than these three promoters (FIG. 2).

In conclusion, the single TetO motif-bearing promoters 2A1, 2A2, and 2B1 were identified as potent promoters exhibiting high levels of TetR-repressibility. The limited set of nucleotide residue substitutions introduced in the CMV promoter to generate these promoters appear not to have affected promoter potency, while yet they were successful in rendering the CMV promoter strongly repressible by TetR. For these reasons, 2A1, 2A2, and 2B1 are considered to represent useful potent alternative TetR-repressible promoters employable for driving transgenes in adenoviral vectors. In combination with TetR-expressing producer cells, like PER.C6-TetR, these new promoters should allow for efficient production of adenoviral vectors encoding inhibitory transgenes. In particular, these promoters could be employed to solve the productivity issue seen for Ad26.ZIKV.001 by replacing the CMV promoter in this vector by one of these and producing the resulting vector on TetR-expressing cell line.

Example 2: Generation of Adenoviral Vectors

Production of pAdApt26.CMVTO2A1.prM-Env Vector

To generate adapter plasmid pAdApt26.CMVTO2A1.prM-Env (SEQ ID NO:16) encoding the M and Env proteins under the control of a TetO-containing CMV promoter, the CMV promoter of the pAdApt26.ZIK.001 (SEQ ID NO:17) was replaced by the TetO-containing CMV promoter (SEQ ID NO:3) of plasmid pMK-RQ.CMVTO2A1_GL_Ao_RFL (SEQ ID NO:18). For that purpose, the relevant CMVTO2A1 fragment of pMK-RQ.CMVTO2A1_GL_Ao_RFL was amplified by PCR and the resulting DNA fragment and pAdApt26.ZIK.001 were digested using the restriction enzymes HindIII-HF and AvrII. A subsequent ligation step resulted in the generation of pAdApt26.CMVTO2A1.prM-Env (SEQ ID NO:16).

Production of the Ad26.ZIKV.002 Vector, which Comprises the ME Zika Transgene Expression Cassette with the 2A1 TetO Containing CMV Promoter (SEQ ID NO:9)

The pAdapt26.CMVTO2A1.prM-Env plasmid DNA, in which the E1 gene of the adenovirus has been replaced by the ZIKV M and Env expression cassette, was subjected to DNA cleaning and DNA sequence analysis prior to Ad26 vector generation in PER.C6®-TetR (described previously in PCT/EP2018/053201 as PER.C6-hCMV.TetR).

To generate the Ad26.ZIKV.002 vector (SEQ ID NO:15), the adapter plasmid was co-transfected together with a cosmid containing the remaining sections of the Ad26 genome in which the Ad26 E3 gene has been partially deleted (pWe.Ad26.dE3.5orf6.cosmid (SEQ ID NO:19)). In the same cosmid, the Ad26 E4 open reading frame 6 (E4orf6) and part of E4orf6/7 has been exchanged for those of adenovirus serotype 5 (Ad5) to allow production of replication-incompetent Ad26 vectors in Ad5 E1-complementing cell lines like HEK293, PER.C6®, PER.C6®-TetR or HER96 cells. Homologous recombination between the 2 DNA vectors, pAdapt26 and cosmid, resulted in formation of an adenovirus genome containing all the virus genes required for the formation of intact viral particles.

Single plaques were isolated by plaque purification on monolayers of PER.C6®-TetR cells covered with agarose. Plaques were amplified on PER.C6®-TetR cells and tested for integrity and identity of the adenovirus genome and correct expression of the transgene. Adenoviruses from plaque #1 were further expanded on PER.C6®-TetR cells and subsequently CsCl-purified.

Example 3: Assessment of Manufacturability of Ad26.ZIKV.002 Vector

Productivity, as defined by titers of virus particles per mL (vp/mL), is critical for upscaling of vector production in bioreactors to provide sufficient material for the different down-stream process steps. Therefore, productivity in suspension PER.C6® cells (sPER.C6®) and suspension PER.C6®-TetR cells (sPER.C6®-TetR) was assessed in small-scale experiments by comparing the Ad26.ZIKV.002 vector (SEQ ID NO:15) to several internal benchmark Ad26 vectors encoding different transgenes. sPER.C6®-TetR was described previously in PCT/EP2018/053201 as PER.C6-AoHV.TetR.

Figure 3:
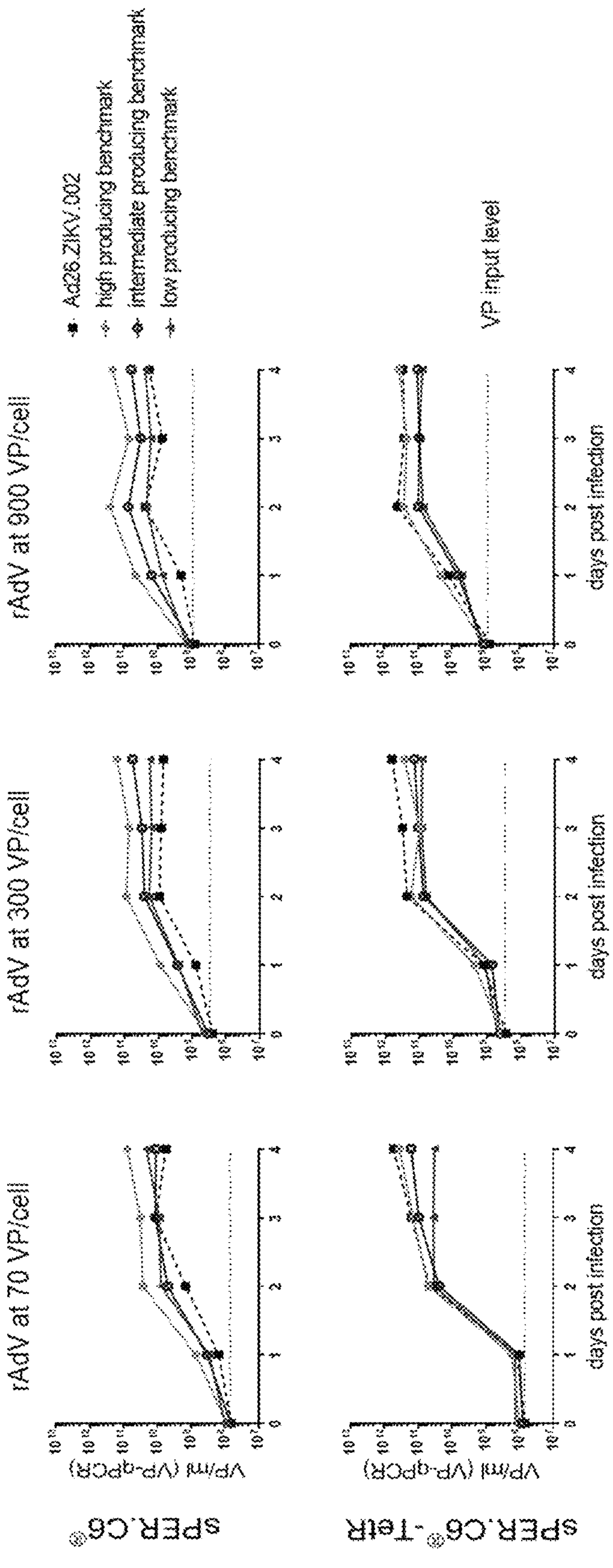
FIG. 3 shows the relative productivity of Ad26.ZIKV.002 in suspension PER.C6® cells (sPER.C6®) and suspension PER.C6®-TetR cells (sPER.C6®-TetR). sPER.C6® cells and sPER.C6®-TetR cells were transduced in shaker flasks with CsCl purified research batches of the Ad26 vectors indicated. Samples were taken at 0, 1, 2, 3, and 4 days post infection and vector particle concentration was measured by VP-qPCR. The dotted line indicates the input material level. In both cell lines, Ad26.ZIK.002 was benchmarked to a good producer, an intermediate producer, and a low producer.

Ad26.ZIKV.002 was generated and tested for relative productivity in the small scale sPER.C6® cells and sPER.C6®-TetR model (FIG. 3). sPER.C6® cells and sPER.C6®-TetR cell cultures, seeded into shaker flasks at a density of $1\times10^6$ cells/mL in a total volume of 10 mL of PERMEXCIS® medium (Lonza; Basel, Switzerland) supplemented with 4 mM L-Glutamine (Lonza), were infected with the different vectors at different virus particle (VP)-to-cell ratios and then incubated for 4 days. In brief, either sPER.C6® cells or sPER.C6®-TetR cells were transduced with 70, 300 and 900 vp/cell of purified Ad26.ZIKV.002 adenoviral particles or one of three internal Ad26 controls (benchmarks), which are known, from previous studies, to be good, intermediate or low producers. Samples were taken on day 0, 1, 2, 3 and 4 after infection and adenoviral vector titers were determined by VP-qPCR. As shown in FIG. 3, Ad26.ZIKV.002 shows comparable productivity to the low producing control at 70, 300 and 900/cell when produced on sPER.C6® cells. When produced on sPER.C6®-TetR cells, Ad26.ZIKV.002 shows comparable productivity to the good producing control at 70, 300 and 900 vp/cell. While the TetO-containing Ad26.ZIKV.002 vector is comparable to a low producer when manufactured on sPER.C6® cells, the yield is increased such that the Ad26.ZIKV.002 vector is comparable to a good producer when manufactured on sPER.C6®-TetR in the small-scale shaker flask model.

Figure 4:
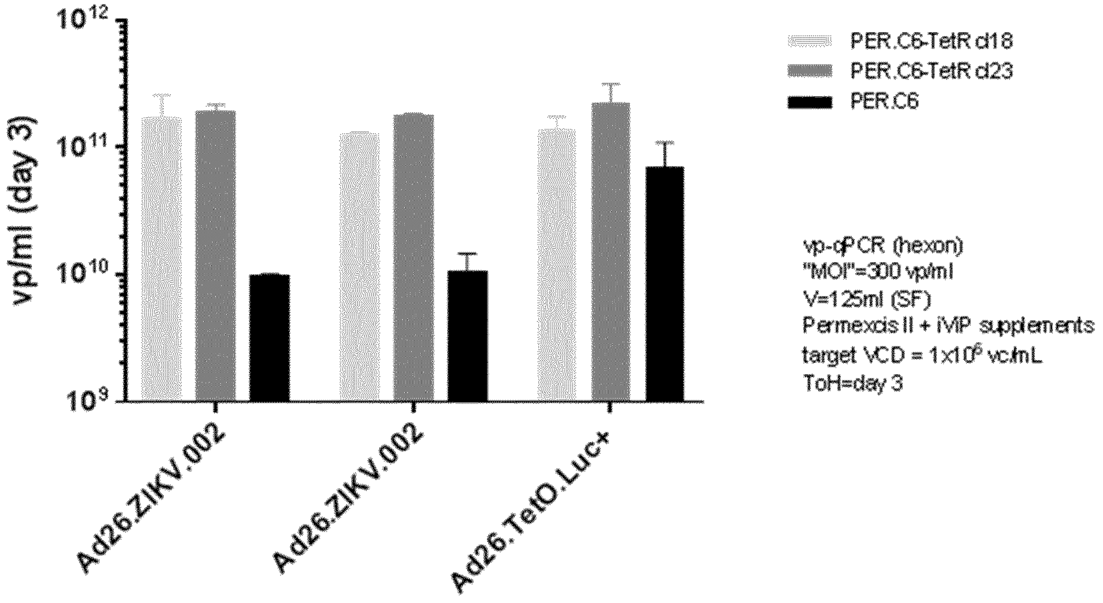
FIG. 4 shows productivity of Ad26.ZIKV.002 in suspension PER.C6® cells and in two different suspension PER.C6®-TetR clones in a small-scale production model.

Ad26.ZIKV.002 was also tested for productivity in sPER.C6® cells and sPER.C6®-TetR using a small-scale model, which is predictive for virus production at larger scale (FIG. 4). In brief, either sPER.C6® cells or sPER.C6®-TetR cells were transduced with 300 vp/cell of purified research batch material of Ad26.ZIKV.002 or Ad26 containing a (non-inhibitory) Luciferase transgene under the control of a TetO-bearing CMV promoter. Virus titers were measured at day 3 post infection by (hexon) vp-qPCR. Productivity of Ad26.ZIKV.002 in sPER.C6®-TetR was ≥1 $Log_{10}$ higher than in PER.C6® cells.

Productivity of Ad26.ZIKV.002 in sPER.C6-TetR at 10/50 Liter Scale

Figure 5A:
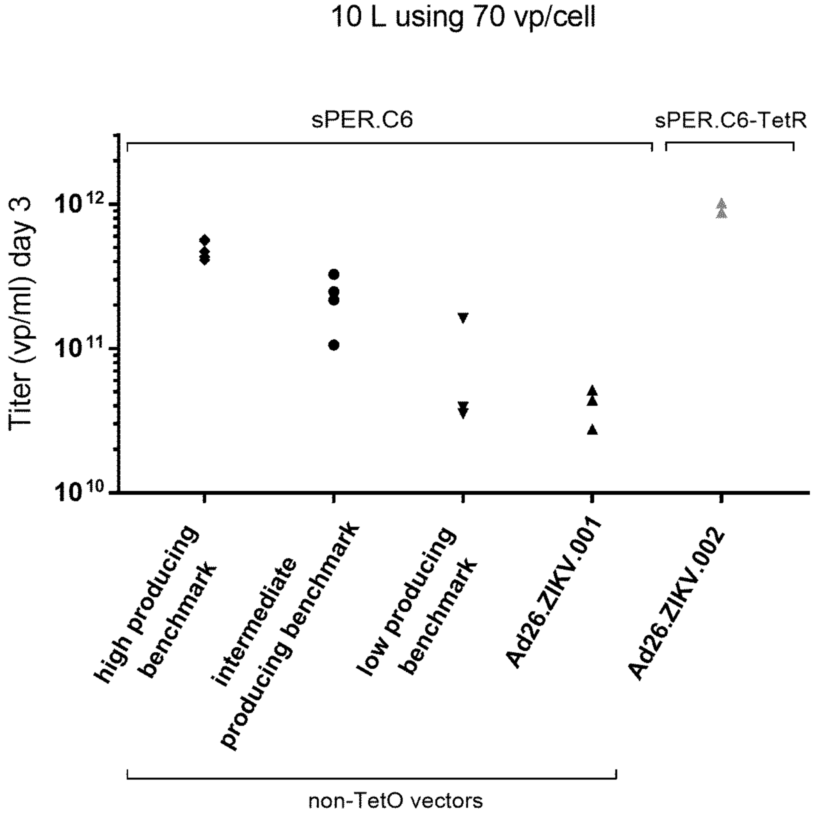
FIGS. 5A-5B show the productivity of Ad26.ZIKV.001 and Ad26.ZIKV.002 in suspension PER.C6® cells and suspension PER.C6®-TetR cells at 70 vp/cell and 10 L scale (A) and 300 vp/cell and 10 L or 50 L scale (B).
Figure 5B:
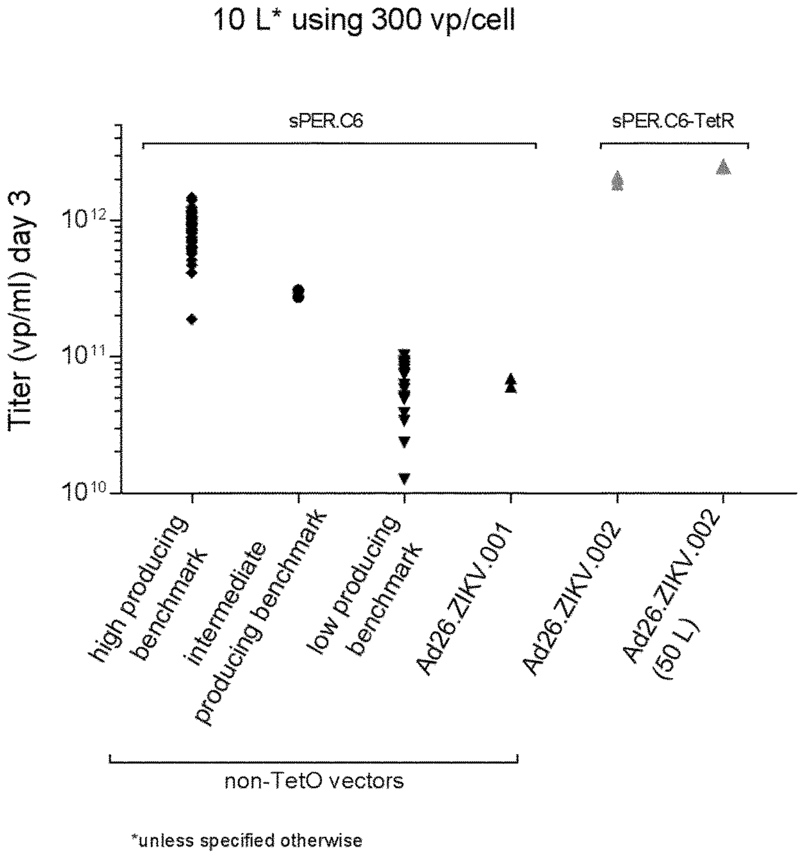

Productivity of Ad26.ZIKV.002 in sPER.C6®-TetR was assessed at high cell density at 10 L and 50 L scale, using 70 vp/cell and 300 vp/cell in 10 L bioreactors and using 300 vp/cell in 50 L bioreactors (FIG. 5). Harvest was performed at day 3 post infection and viral particle (vp) titers were measured by Capillary Electrophoresis. Viral particle titers achieved at day 3 in sPER.C6®-TetR were between 1.5-2 $Log_{10}$ higher than for Ad26.ZIKV.001 in sPER.C6®.

Example 4: Ad26.ZIKV.002 is Immunogenic in Non-Human Primates and Confers Protection Against ZIKV Challenge Non-human primates (NHP, species Rhesus macaques) were immunized once intramuscularly with $10^{11}$ vp Ad26.ZIKV.002, or immunized with formulation buffer (Sham). Four weeks post immunization, animals were bled, and challenged subcutaneously with $10^3$ pfu ZIKV-BR.

Figure 6:
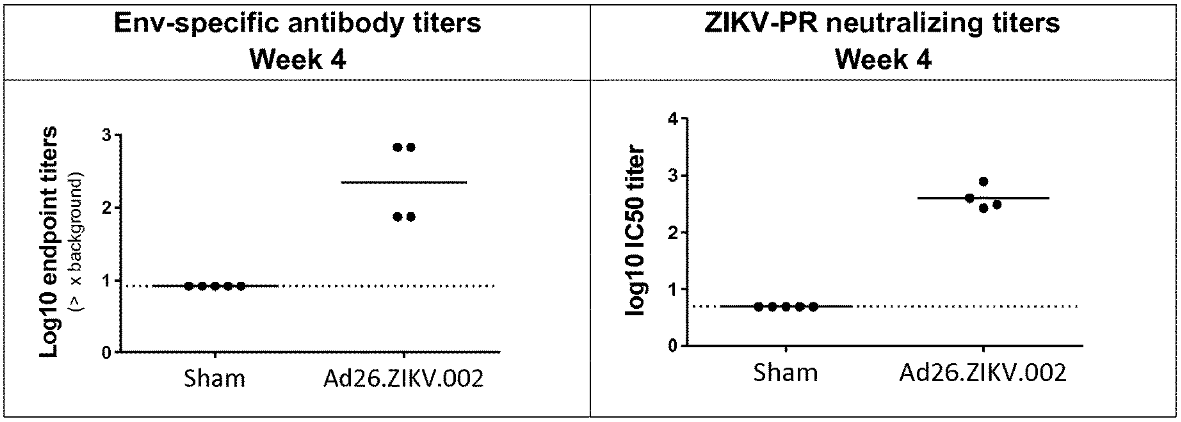
FIG. 6 shows humoral responses in sera of NHP (n=4 or 5 per group) immunized with $10^{11}$ vp Ad26.ZIKV.002, or formulation buffer (Sham), at 4 weeks post-immunization. Left panel: Env-specific binding IgG antibody responses were determined using a commercially available ELISA kit (Alpha Diagnostics; San Antonio, Tex.) and expressed as the $\log_{10}$ of the inverse first dilution above 5× the background value of naïve sera. The mean responses per group are indicated with a horizontal line. The dotted line shows the lower limit of detection that is defined as one dilution below the start dilution of the samples (0.92 $\log_{10}$). Right panel: ZIKV-PR neutralization titers were measured by Focus Reduction Neutralization Tests (Southern Research; Birmingham, Ala.) and are reported as the $\log_{10}$ of the inverse serum dilution that reduces the number of input virus by 50% ($IC_{50}$). The mean responses per group are indicated with a horizontal line. The dotted line shows the lower limit of detection that is defined as one dilution below the start dilution of the samples (0.70 $\log_{10}$).

Ad26.ZIKV.002 induced humoral immune responses in NHP, as shown by the induction of Env binding antibody titers (FIG. 6, left panel), and ZIKV-PR neutralizing antibody titers (FIG. 6, right panel).

Figure 7:
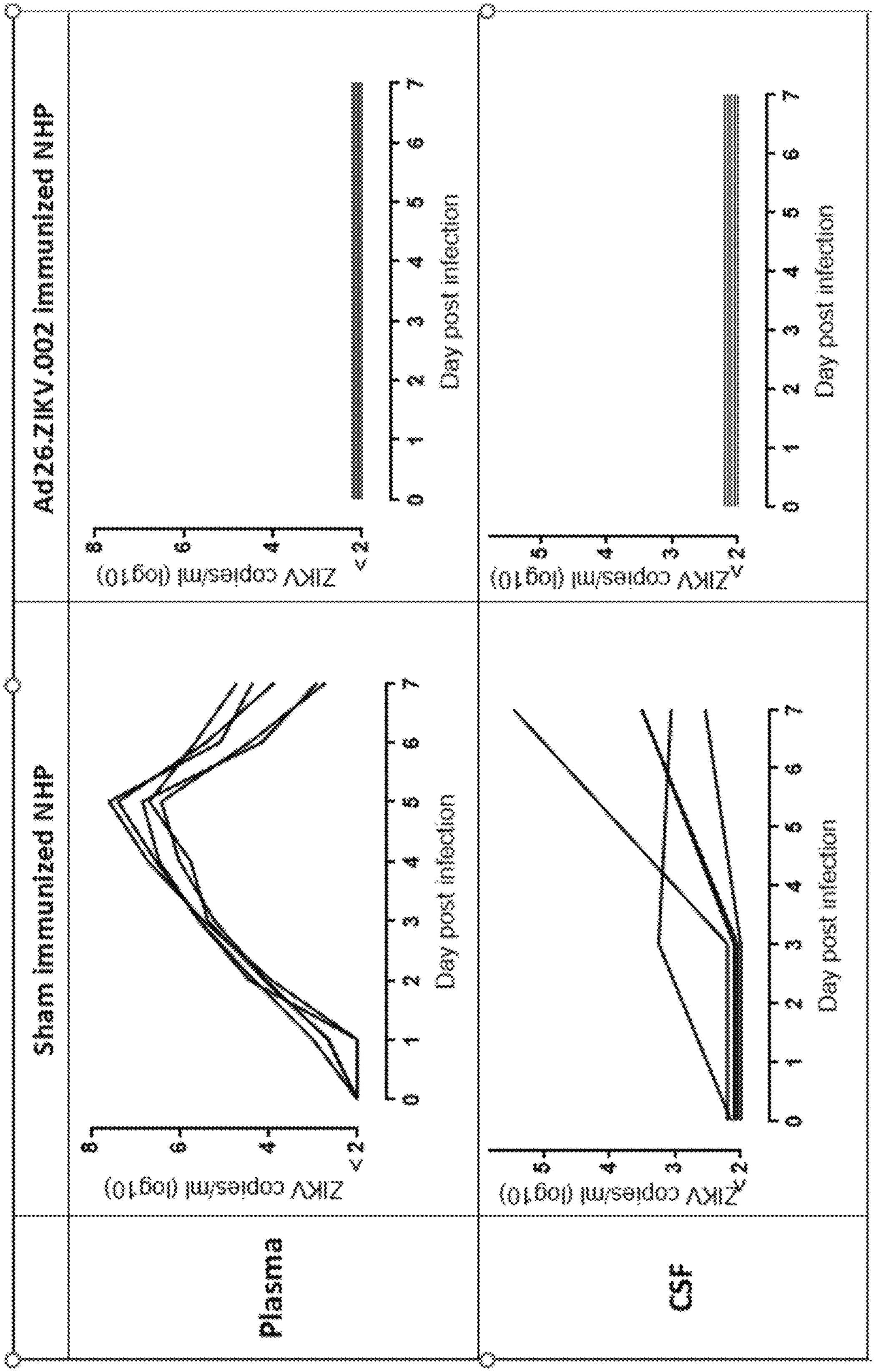
FIG. 7 shows protective efficacy of Ad26.ZIKV.002 against ZIKV-BR challenge in NHP. Animals (n=4 or 5 per group) were immunized with $10^{11}$ vp Ad26.ZIKV.002 (right panels), or formulation buffer (Sham, left panels). Four weeks post-immunization animals were challenged via the subcutaneous route with $10^3$ pfu ZIKV-BR. Plasma and cerebrospinal fluid (CSF) were obtained pre-challenge and at several time points after challenge. Viral load in plasma (upper panels) or CSF (lower panels) was determined by RT-PCR and depicted as $\log_{10}$ ZIKV copies/mL. The limit of detection of this assay was <100 copies/mL.

All Sham-injected NHP showed viral loads in the plasma after challenge. In contrast, NHP immunized with Ad26.ZIKV.002, were all protected against challenge with ZIKV-BR, as evidenced by undetectable viral RNA loads in plasma samples from these animals (FIG. 7, upper panels).

In addition, viral loads in cerebrospinal fluid (CSF) were measured at days 3 and 7 after ZIKV-BR challenge. Whereas ZIKV RNA was detectable in in CSF samples of all sham-immunized animals, no virus was detectable in CSF samples of Ad26.ZIKV.002-immunized animals (FIG. 7, lower panels).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

The invention claimed is:

1. An adenoviral vector comprising a nucleotide sequence encoding a Zika virus M and Env antigen, wherein the nucleotide sequence encoding the Zika virus M and Env antigen is operably linked to a cytomegalovirus (CMV) promoter comprising at least one tetracycline operator (TetO) motif, wherein the CMV promoter comprising at least one TetO motif comprises a nucleotide sequence selected from the group consisting of SEQ ID NOs:3-5.

2. The adenoviral vector of claim 1, wherein the Zika virus M and Env antigen comprises the amino acid sequence of SEQ ID NO: 1.

3. The adenoviral vector of claim 1, wherein the adenoviral vector is selected from the group consisting of ChAd3, SAdV, rhAd51, rhAd52, rhAd53, hAd4, hAd5, hAd26, and hAd35.

4. The adenoviral vector of claim 1, wherein the adenoviral vector comprises a nucleotide sequence selected from the group consisting of SEQ ID NOs:9-11 and SEQ ID NO: 15.

5. An isolated host cell comprising the adenoviral vector of claim 1.

6. The host cell of claim 5, wherein the host cell further comprises a nucleotide sequence encoding a tetracycline repressor (TetR) protein.

7. The host cell of claim 5, wherein the host cell is a PER.C6® host cell.

8. A pharmaceutical composition comprising the adenoviral vector of claim 1 and a pharmaceutically acceptable carrier.

9. A method of producing an adenoviral particle comprising a Zika virus M and Env antigen, wherein the method comprises:

a. contacting a host cell with an adenoviral vector comprising a nucleotide sequence encoding a Zika virus M and Env antigen, wherein the nucleotide sequence encoding the Zika virus M and Env antigen is operably linked to a cytomegalovirus (CMV) promoter comprising at least one tetracycline operator (TetO) motif; and b. growing the host cell under conditions wherein the adenoviral particle comprising the Zika M and Env antigen is produced, wherein the CMV promoter comprising at least one TetO motif comprises a nucleotide sequence selected from the group consisting of SEQ ID NOs:3-5.

10. The method of claim 9, wherein the Zika virus M and Env antigen comprises the amino acid sequence of SEQ ID NO: 1.

11. The method of claim 9, wherein the adenoviral vector is selected from the group consisting of ChAd3, SAdV, rhAd51, rhAd52, rhAd53, hAd4, hAd5, hAd26, and hAd35.

12. The method of claim 9, wherein the adenoviral vector comprises a nucleotide sequence selected from the group consisting of SEQ ID NOs:9-11 and SEQ ID NO: 15.

13. The method of claim 9, wherein the host cell further comprises a nucleotide sequence encoding a tetracycline repressor (TetR) protein.

14. The method of claim 12, wherein the host cell is a PER.C6® host cell.

15. A pharmaceutical composition comprising an adenoviral particle produced by the method of claim 9 and a pharmaceutically acceptable carrier.

16. A method for inducing an immune response against a Zika virus infection in a human subject in need thereof, the method comprising administering to the subject the pharmaceutical composition of claim 15.

17. The method of claim 16, wherein the pharmaceutical composition is administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion, by catheter, by lavage, or by gavage.

18. A kit comprising:

a. an adenoviral vector comprising a nucleotide sequence encoding a Zika virus M and Env antigen, wherein the nucleotide sequence encoding the Zika virus M and Env antigen is operably linked to a cytomegalovirus (CMV) promoter comprising at least one tetracycline operator (TetO) motif; and b. a host cell comprising a nucleotide sequence encoding a tetracycline repressor (TetR) protein, wherein the CMV promoter comprising at least one TetO motif comprises a nucleotide sequence selected from the group consisting of SEQ ID NOs:3-5.

19. The kit of claim 18, wherein the Zika virus M and Env antigen comprises the amino acid sequence of SEQ ID NO: 1.

20. The kit of claim 18, wherein the adenoviral vector is selected from the group consisting of ChAd3, SAdV, rhAd51, rhAd52, rhAd53, hAd4, hAd5, hAd26, and hAd35.

21. The kit of claim 18, wherein the adenoviral vector comprises a nucleotide sequence selected from the group consisting of SEQ ID NOs:9-11 and SEQ ID NO:15.

22. The kit of claim 18, wherein the host cell is a PER.C6® host cell.

* * * * *